(12) United States Patent
Gentry et al.

(10) Patent No.: US 8,407,066 B2
(45) Date of Patent: Mar. 26, 2013

(54) INSURANCE ESTIMATING SYSTEM

(75) Inventors: Travis W. Gentry, Highlands Ranch, CO (US); Timothy R. Estes, Parker, CO (US); David L. Harrison, Denver, CO (US)

(73) Assignee: Financial Healthcare Systems, LLC, Greenwood Village, CO (US)

( * ) Notice: Subject to any disclaimer, the term of this patent is extended or adjusted under 35 U.S.C. 154(b) by 774 days.

(21) Appl. No.: 12/115,446

(22) Filed: May 5, 2008

(65) Prior Publication Data

US 2008/0275737 A1 Nov. 6, 2008

Related U.S. Application Data

(60) Provisional application No. 60/916,043, filed on May 4, 2007, provisional application No. 61/026,635, filed on Feb. 6, 2008.

(51) Int. Cl.
*G06Q 50/00* (2012.01)
*G06Q 40/00* (2012.01)

(52) U.S. Cl. ............................. 705/2; 705/4

(58) Field of Classification Search .................. 705/2, 4
See application file for complete search history.

(56) References Cited

U.S. PATENT DOCUMENTS

| | | | | |
|---|---|---|---|---|
| 4,491,725 A | * | 1/1985 | Pritchard | 705/2 |
| 4,667,292 A | * | 5/1987 | Mohlenbrock et al. | 705/2 |
| 5,018,067 A | | 5/1991 | Mohlenbrock et al. | |
| 5,557,514 A | | 9/1996 | Seare et al. | |
| 6,061,657 A | | 5/2000 | Whiting-O'Keefe | |
| 6,108,641 A | * | 8/2000 | Kenna et al. | 705/35 |
| 6,223,164 B1 | | 4/2001 | Seare et al. | |
| 7,222,079 B1 | | 5/2007 | Seare et al. | |
| 7,467,094 B2 | | 12/2008 | Rosenfeld et al. | |
| 2002/0147617 A1 | | 10/2002 | Schoenbaum et al. | |
| 2003/0050795 A1 | | 3/2003 | Baldwin, Jr. et al. | |
| 2003/0200118 A1 | | 10/2003 | Lee et al. | |
| 2004/0078235 A1 | | 4/2004 | Tallal, Jr. | |
| 2004/0153405 A1 | | 8/2004 | Millary et al. | |
| 2005/0010438 A1 | | 1/2005 | York et al. | |
| 2005/0119918 A1 | | 6/2005 | Berliner | |
| 2005/0177490 A1 | | 8/2005 | Pembroke | |

(Continued)

FOREIGN PATENT DOCUMENTS

CA 2553394 * 1/2007

OTHER PUBLICATIONS

Holley, Why All Prescribed Medications Are Not Taken: Results from a Survey of Chronic Dialysis Patients, 2006, Advances in Peritoneal Dialysis, vol. 22, p. 162-166.*

*Primary Examiner* — Tran Nguyen
(74) *Attorney, Agent, or Firm* — William J. Lenz; Neal, Gerber & Eisenberg LLP

(57) ABSTRACT

Disclosed is a computerized method and system for estimating treatment costs for a health care product and/or service for a health care patient. The estimate of health care costs is calculated before the patient is discharged from the facility providing the health care product or service. The estimate of health care costs may also be performed prior to any treatment or admission to the health care facility of the health care patient. The estimate of treatment costs may include a patient payable amount that estimates the cost of the health care product/service that will be the patient's responsibility. The health care patient may be billed for the health care product or service prior to discharging the health care patient and/or prior to providing the health care product or service to the health care patient. If desired, a loan for the estimated patient payable amount may be arranged and/or provided to the health care patient to pay for the patient's portion of the cost for the health care product and/or service.

18 Claims, 34 Drawing Sheets

1400 PAGE 1 OF LOW LEVEL DETAIL FLOW CHART OF ESTIMATE CALCULATION

U.S. PATENT DOCUMENTS

| | | |
|---|---|---|
| 2005/0187797 A1 | 8/2005 | Johnson |
| 2005/0222922 A1 | 10/2005 | Lynch |
| 2005/0273360 A1 | 12/2005 | Drucker et al. |
| 2006/0080139 A1 | 4/2006 | Mainzer |
| 2007/0005403 A1 | 1/2007 | Kennedy et al. |
| 2007/0011088 A1* | 1/2007 | Cracchiolo et al. ............ 705/39 |
| 2007/0033070 A1 | 2/2007 | Beck et al. |
| 2007/0271119 A1 | 11/2007 | Boerger et al. |

* cited by examiner

400 LOW LEVEL DETAIL FLOW CHART OF ESTIMATION STEP 2 / SELECTING A PROCEDURE FOR ONE EMBODIMENT

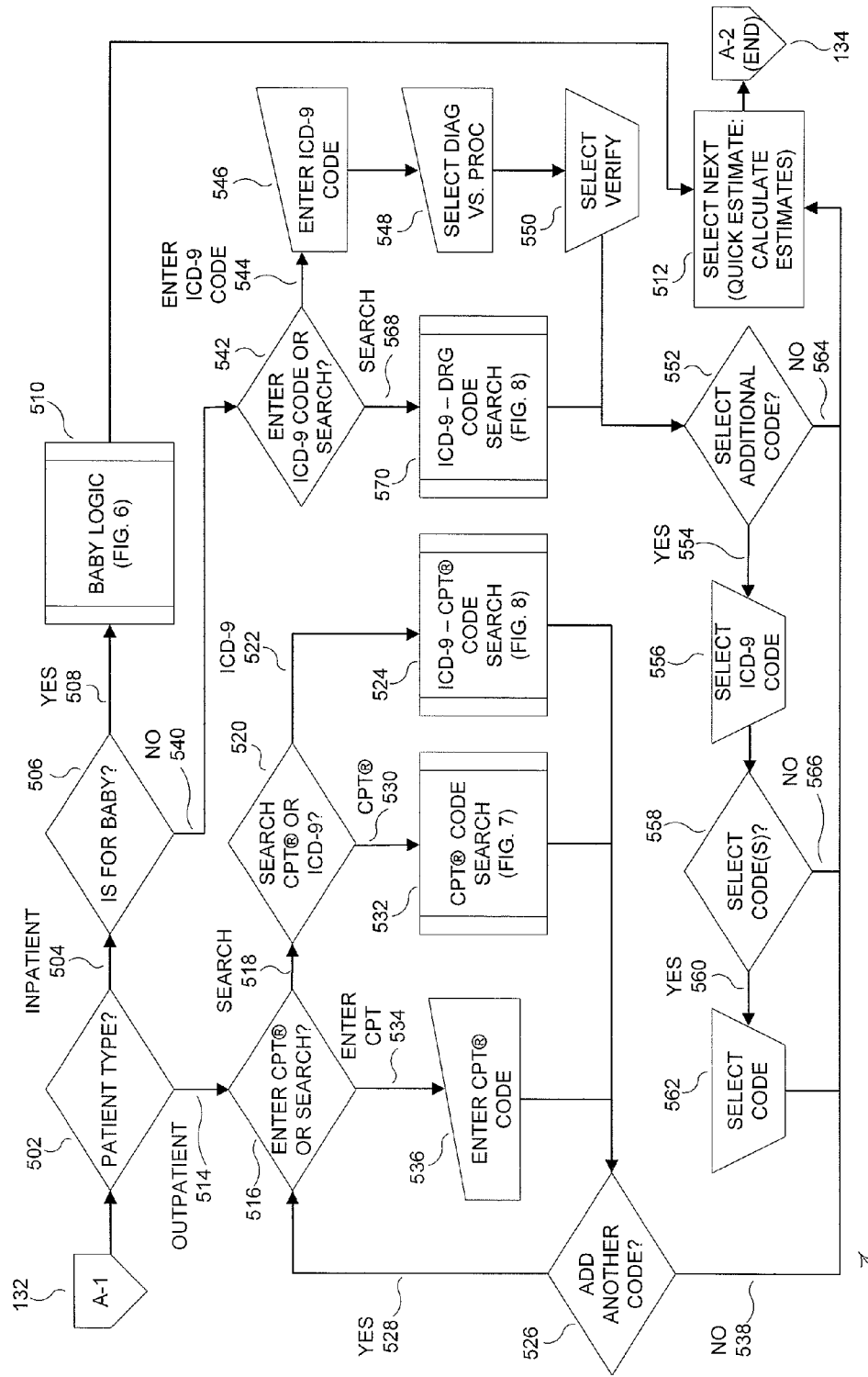

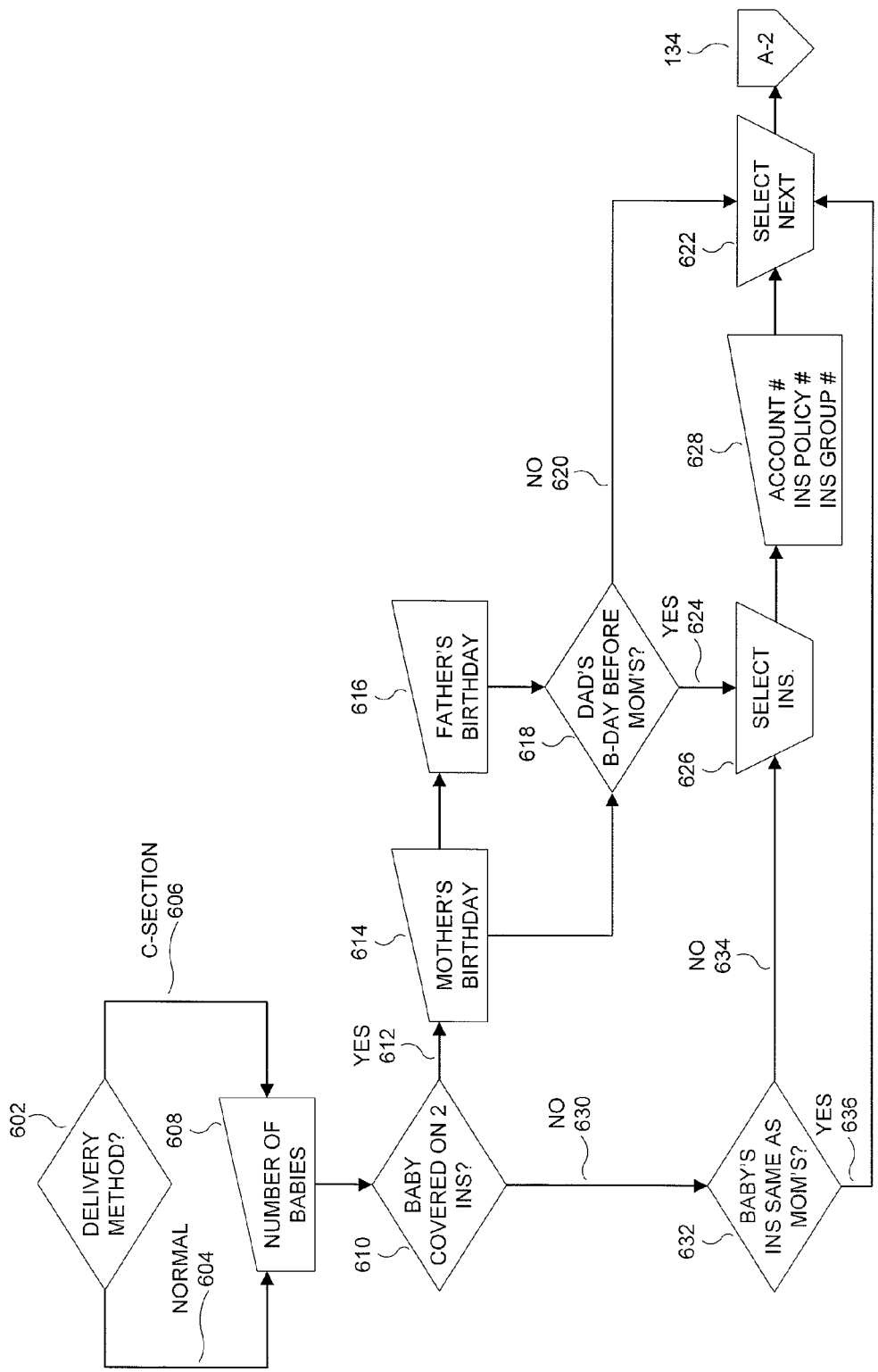

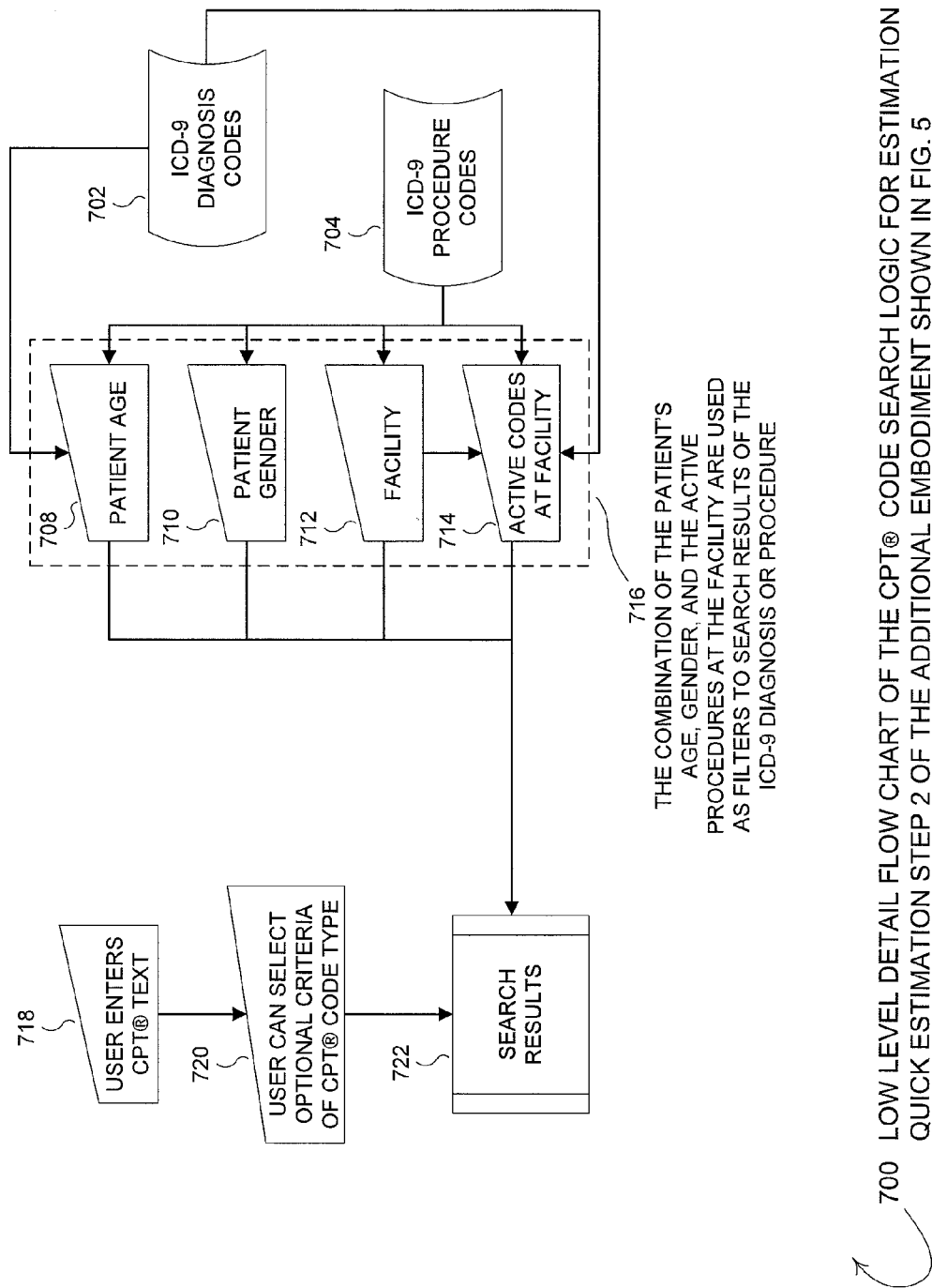

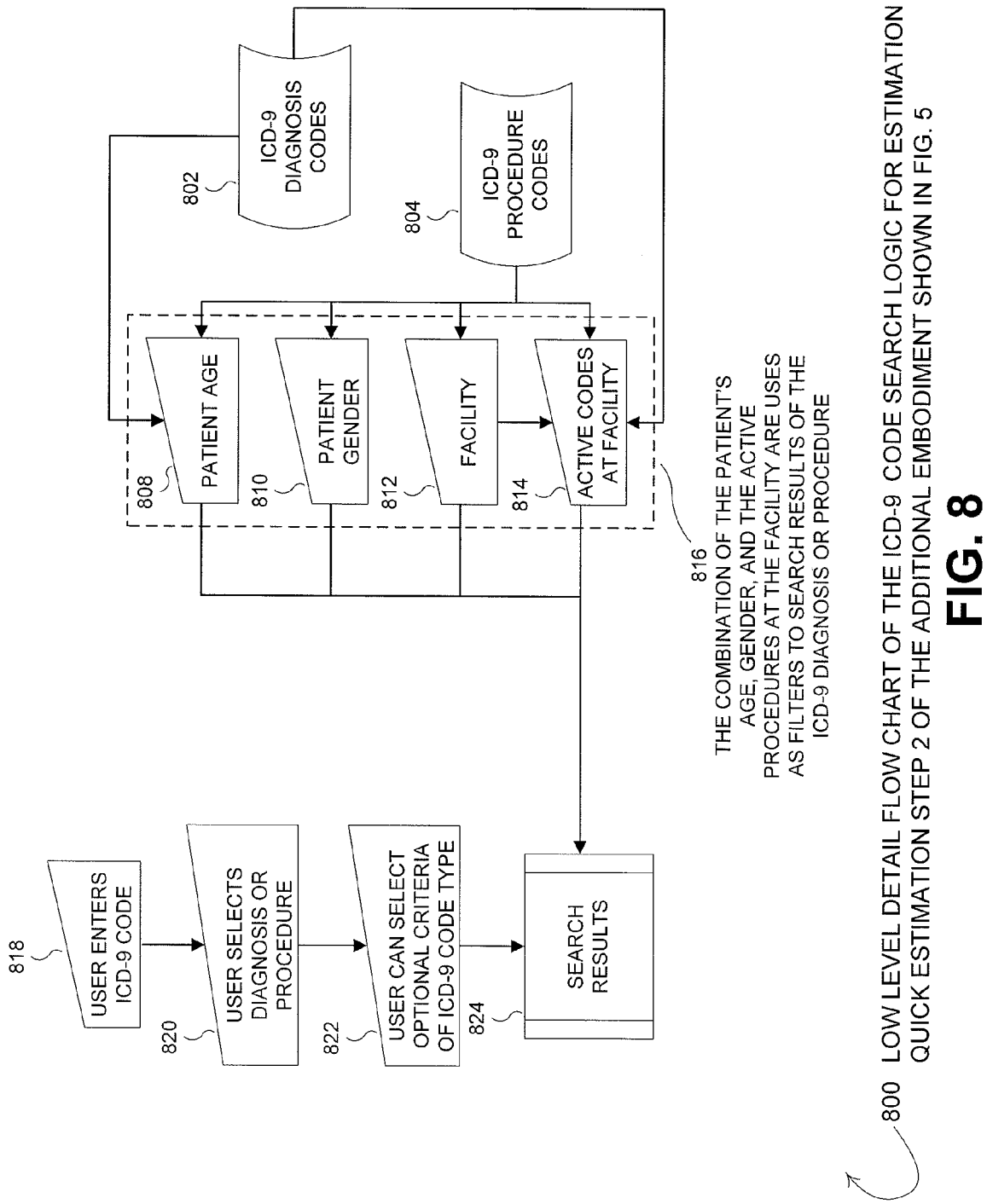

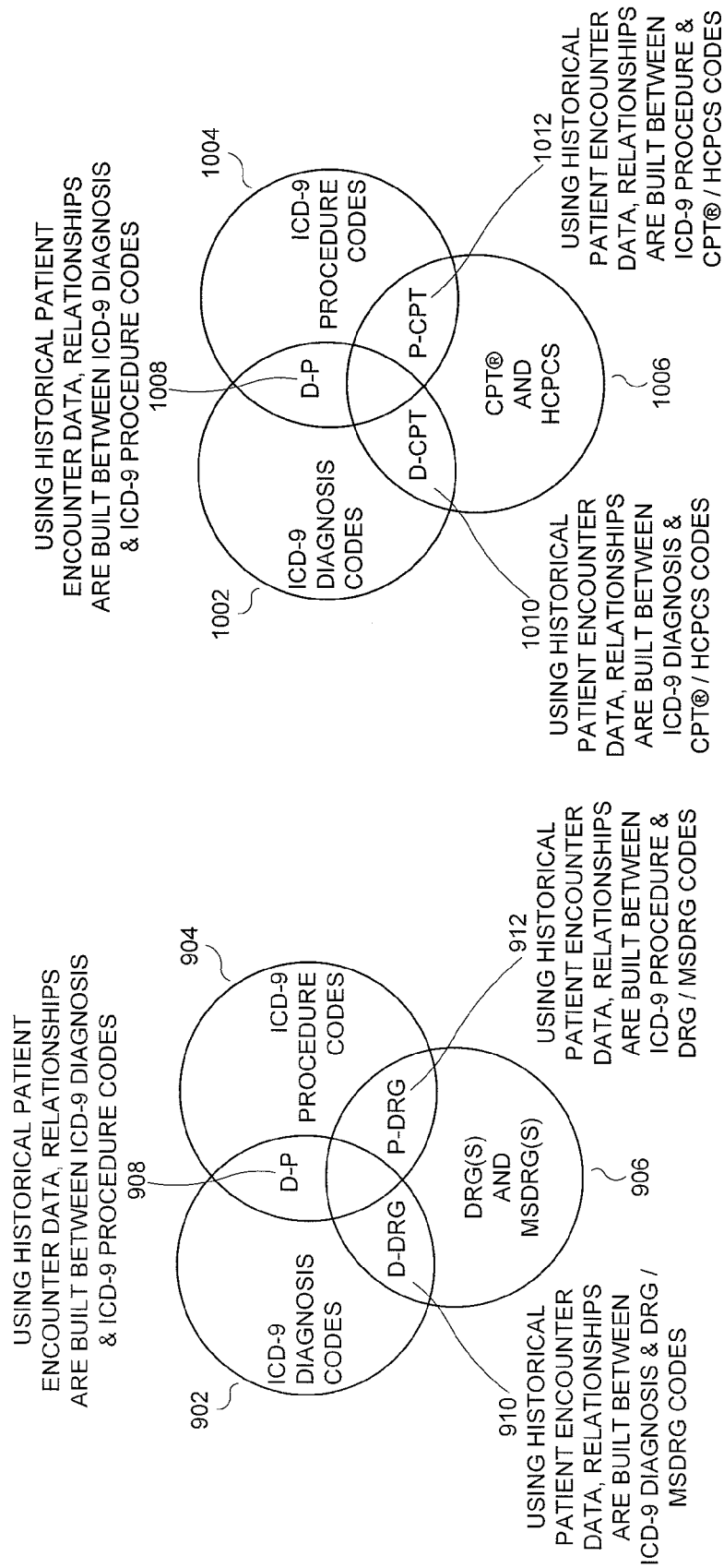

1400 PAGE 1 OF LOW LEVEL DETAIL FLOW CHART OF ESTIMATE CALCULATION

1700 LOW LEVEL DETAIL FLOW CHART OF ESTIMATION HISTORY PATH OF THE OVERALL INSURANCE ESTIMATION SYSTEM

1800 LOW LEVEL DETAIL FLOW CHART OF INSURANCE CONTRACT ADMIN PATH OF THE OVERALL INSURANCE ESTIMATION SYSTEM

2200 LOW LEVEL DETAIL FLOW CHART OF CLINIC LOGIC FOR THE INSURANCE CONTRACT ADMIN PATH SHOWN IN FIG. 18

2500 LOW LEVEL DETAIL FLOW CHART OF REPORTING PATH OF THE OVERALL INSURANCE ESTIMATION SYSTEM

Saint Joseph HealthCare  Saint Joseph Hospital
One Saint Joseph Drive
Lexington, KY 40504
Phone: (859) 313-4344

---
ESTIMATE WORKSHEET
---

3102
- Patient Name: Joe E. Patient  Account Number: 1234567890
- Service Date: 1/23/2007  Insurance Company: Humana
- ICD #1: 759.03 Ab Pain Rt Low Q  Policy Number: 12345
- 3104 — ICD #2: 45.23 Colonoscopy  Group Number: 12345
- DRG: 183 Esophagitis Gastroent Out of Pocket Max: $2,500.00
Out of Pocket Met: $500.00
Deductible: $1,000.00
Deductible Met: $500.00     ~3106
Co-Pay: $75.00
Co-Insurance: 5%

3108

Estimated Patient Amount: $666.55
Estimated Charges: $2,406.00    ~3110

3100 EXAMPLE ESTIMATION WORKSHEET FOR A PRE-INPATIENT
TYPE OF HEALTH CARE PATIENT

FIG. 31

Mercy Medical Center

Mercy Medical Center
1512 12th Avenue Road
Nampa, ID 83686
Phone: (208) 463-5000

ESTIMATE WORKSHEET

3202
| Patient Name: | Jane E. Patient | Account Number: | 1234567890 |
3204 | Service Date: | 1/23/2007 | Insurance Company: | BlueCross HMO |
Diagnosis/Procedure: 373 Pregnancy, Vaginal    Policy Number: 12345
Out of Pocket Max:    $2,500.00    Group Number: 123456
Out of Pocket Met:    $500.00
Deductible:    $1,000.00
Deductible Met:    $500.00    ~3206
Co-Pay:    $260.00
Co-Insurance:    5%

3208

Mother's Estimated Patient Amount:    $817.11
Mother's Estimated Charges:    $2,092.29    ~3210

3212
Baby's Diagnosis: Newborn        Insurance Company: BlueCross HMO
Out of Pocket Max:    $2,500.00
Out of Pocket Met:    $667.11
Deductible:    $1,000.00
Deductible Met:    $1,000.00    ~3214        3216
Co-Pay:    $250.00
Co-Insurance:    5%

Baby's Estimated Patient Amount:    $268.61
Baby's Estimated Charges:    $622.13    ~3218

Total Estimated Patient Amount:    $1,085.72
Total Estimated Charges:    $2,714.42    ~3220

3200 EXAMPLE ESTIMATION WORKSHEET FOR A PRE-INPATIENT
OBSTETRIC TYPE OF HEALTH CARE PATIENT

FIG. 32

Saint Joseph East

Saint Joseph East
150 North Eagle Creek Drive
Lexington, KY 40509
Phone: (859) 957-5293

ESTIMATE WORKSHEET

| | | | |
|---|---|---|---|
| Patient Name: | John Patient | Account Number: | 1234567890 |
| Service Date: | 1/23/2007 | Insurance Company: | Aetna |
| CPT #1: | 73630 X-ray exam of foot | Policy Number: | 123456 |
| CPT #1: | 73630 X-ray exam of foot | Group Number: | 123456 |
| CPT #1: | 73630 X-ray exam of foot | | |
| Out of Pocket Max: | $2,000.00 | | |
| Out of Pocket Met: | $1,000.00 | | |
| Deductible: | $1,500.00 | | |
| Deductible Met: | $1,000.00 | | |
| Co-Pay: | $100.00 | | |
| Co-Insurance: | 10% | | |

Estimated Patient Amount: $120.43
Estimated Charges: $120.43

3300 EXAMPLE ESTIMATION WORKSHEET FOR A PRE-INPATIENT TYPE OF HEALTH CARE PATIENT

FIG. 33

| OFFICE USE ONLY |

Date: _____     Time: _____

Notes: _____
_____

| PATIENT FINANCIAL RESPONSIBILITY |

The information provided in this letter is an estimate and not a guarantee of what you will be charged. Please understand there are variables involved in estimating your charges such as length of time spent in surgery or recovery, number of days spent in the hospital, specific equipment required, and/or additional tests requested. The estimated charges do not include any physician charges (e.g. office visit, surgeon, anesthesiologist, emergency room physician, radiologist, pathologist, consulting physcians, etc.). If you have insurance, your benefits will ultimately determine the amount you owe (including deductibles, co-pay, co-insurance, and out-of-pocket maximums).

Patient Account Number: <u>1234567890</u>

Method of Payment:    ☐ Check    ☐ Money Order    ☐ Credit Card

Credit Card Type:    ☐ Visa    ☐ Mastercard    ☐ American Express    ☐ Discover

Credit Card Number: _____    Exp Date: _____

Amount: _____   Zip Code: _____   Phone: _____

Card Holder Name: _____

Patient Signature: _____

Return a copy of this letter and your deposit in the enclosed envelope to:
Saint Joseph Hospital, Attn: Cashier, One Saint Joseph Drive, Lexington, KY 40504
or you may call our cashier (859) 313-4344 (REF: Patient Account #) with your credit card info

3400 EXAMPLE FINANCIAL RESPONSIBILITY SECTION FOR AN
ESTIMATION WORKSHEET / LETTER

FIG. 34

INSURANCE ESTIMATING SYSTEM

CROSS REFERENCE TO RELATED APPLICATIONS

This application is a based upon and claims priority to: U.S. provisional application Ser. No. 60/916,043, filed May 4, 2007, by Travis W. Gentry and Timothy R. Estes, entitled "Insurance Estimating System" and U.S. provisional application No. 61/026,635, filed Feb. 6, 2008, by Travis W. Gentry and Timothy R. Estes, entitled "Insurance Estimating System," all of which are specifically incorporated herein by reference for all that they disclose and teach.

BACKGROUND OF THE INVENTION

Many times the accounting and billing for medical services rendered, rather than the patient treatment itself, is one the most challenging functions for a doctor's office or other health care provider to perform. Most insurance policies have some form of sharing of the medical costs between the patient and the insurance company utilizing concepts such as deductibles, out of pocket maximums, co-pays, co-insurance, and family versus individual benefits. With the many different concepts and overlapping coverage of the deductibles, co-pays, co-insurance, out of pocket maximums, etc. it can be very difficult for a health care provider to determine the exact amounts owed between the patient and the insurance company. The complexity of calculating the amounts owed is increased due to the contractual relationships between the insurance company and the health care provider. The contractual relationship typically defines the allowable prices that may be charged for different health care products or services.

Due to the complexities of the insurance coverage system as well as the inherent delays in a large, bureaucratic entity such as an insurance company, it may take quite a while to process the insurance and subsequent payments for a health care product or service provided to a health care patient. The patient is normally not billed for their portion of the payment until the final division of payments is determined by the insurance company. Typically, the insurance company does not figure out the final cost divisions until 30 to 90 days after the health care product or service has been provided. Thus, the patient is not billed for up to 30 to 90 days after the health care product or service was provided. Many times, the patient is shocked by the new bill thinking that all of the bills had been paid months earlier. If the patient takes time to protest the charges, the patient may not pay for another 30-180 days, and the health care provider is left waiting for complete payment for 90 to 360 or more days after the health care product or service was provided.

SUMMARY OF THE INVENTION

An embodiment of the present invention may comprise a computerized method for estimating treatment related amounts, including treatment costs, contract allowable amounts, and patient payable amounts, of a health care provider for a health care patient to receive a health care product/service comprising: supplying a computer system that runs computer software, the computer software performing the computerized method for estimating the treatment related amounts of the health care provider for the health care patient to receive the health care product/service, the computer system having computer readable storage media for storing the computer software as well as data entry information, the estimated treatment related amounts including estimated treatment costs, an estimated allowable amount, and an estimated patient payable amount; entering facility information for a facility that is to provide the health care product/service to the health care patient into the computer software; entering patient information about the health care patient into the computer software; entering insurance information about health insurance provided by an insurance company that covers the health care patient into the computer software; entering health care code information about the health care product/service that is to be provided to the health care patient into the computer software; entering insurance benefits information for the health insurance that covers the health care patient into the computer software; performing estimation calculations in the computer software prior to the health care patient being discharged from the facility and prior to final costs for the health care product/service being available from the insurance company such that the estimated treatment related amounts to receive the health care product/service are calculated by taking into account the facility information, the patient information, the insurance information, the insurance benefits information, and the health care code information; creating an estimation report in the computer program that shows the estimated treatment related amounts for the health care patient to receive the health care product/service prior to the health care patient being dismissed from the facility; and delivering the estimation report to an interested party.

An embodiment of the present invention may further comprise an insurance estimation system for estimating treatment related amounts, including treatment costs, contract allowable amounts, and patient payable amounts of a health care provider for a health care patient to receive a health care product/service comprising: a computer system that runs computer software of the insurance estimation system that estimates the treatment related amounts, the computer system having computer readable storage media for storing the computer software as well as data entry information, the estimated treatment related amounts including estimated treatment costs, an estimated allowable amount, and an estimated patient payable amount; a facility input that accepts entry of facility information for a facility that is to provide the health care product/service to the health care patient into the computer software; a patient information input that accepts entry of patient information about the health care patient into the computer software; an insurance information input that accepts entry of insurance information about health insurance provided by an insurance company that covers the health care patient into the computer software; an insurance benefits information input that accepts entry of insurance benefits information for the health insurance that covers the health care patient into the computer software; a health care code information input that accepts entry of health care code information about the health care product/service that is to be provided to the health care patient into the computer software; an estimate calculation process that performs estimation calculations in the computer software prior to the health care patient being discharged from the facility and prior to final costs for the health care product/service being available from the insurance company such that the estimated treatment related amounts to receive the health care product/service are calculated by taking into account the facility information, the patient information, the insurance information, the insurance benefits information, and the health care code information; an estimate report creation process that creates an estimation report in the computer program that shows the estimated treatment related amounts for the health care patient to receive the health care product/service prior to the health care patient being dismissed from the facility; and an estimate delivery process that delivers the estimation report to an interested party.

An embodiment of the present invention may further comprise an insurance estimation system for estimating treatment related amounts, including treatment costs, contract allowable amounts, and patient payable amounts of a health care provider for a health care patient to receive a health care product/service comprising: means for running computer software of the insurance estimation system; means for entering facility information for a facility that is to provide the health care product/service to the health care patient into the computer software; means for entering patient information about the health care patient into the computer software; means for entering insurance information about health insurance provided by an insurance company that covers the health care patient into the computer software; means for entering insurance benefits information for the health insurance that covers the health care patient into the computer software; means for entering health care code information about the health care product/service that is to be provided to the health care patient into the computer software; means for performing estimation calculations in the computer software prior to the health care patient being discharged from the facility and prior to final costs for the health care product/service being available from the insurance company such that the estimated treatment related amounts to receive the health care product/service are calculated by taking into account the facility information, the patient information, the insurance information, the insurance benefits information, and the health care code information; creating an estimation report in the computer program that shows the estimated treatment related amounts for the health care patient to receive the health care product/service prior to the health care patient being dismissed from the facility; and means for delivering the estimation report to an interested party.

BRIEF DESCRIPTION OF THE DRAWINGS

In the drawings,

FIG. 5 is a low level flow chart of the operation of estimation step number two (selecting a procedure/entering treatment information) of the estimation and quick estimation paths of an additional embodiment of the overall insurance estimation system.

FIG. 6 is a low level flow chart of the operation of the baby logic for estimation step number two of the estimation and quick estimation paths of the additional embodiment shown in FIG. 5.

FIG. 7 is a low level flow chart of the operation of the Current Procedural Terminology (CPT®) code search logic for estimation step number two of the estimation and quick estimation paths of the additional embodiment shown in FIG. 5.

FIG. 8 is a low level flow chart of the operation of the International Classification of Diseases (ICD) code search logic for estimation step number two of the estimation and quick estimation paths of the additional embodiment shown in FIG. 5.

FIG. 9 is a Venn diagram of the relationship between Diagnostic Related Groups (DRG)/Medical Severity Diagnostic Related Groups (MSDRG), ICD Diagnosis, and ICD Procedure codes of FIG. 8.

FIG. 10 is a Venn diagram of the relationship between CPT/Healthcare Common Procedure Coding System (HCPCS), ICD Diagnosis, and ICD Procedure codes of FIG. 7.

FIG. 31 is an example estimation worksheet for an embodiment of a pre-inpatient type of health care patient.

FIG. 32 is an example estimation worksheet for an embodiment of a pre-inpatient obstetric type of health care patient.

FIG. 33 is an example estimation worksheet for an embodiment of an outpatient type of health care patient.

FIG. 34 is an example financial responsibility section for an embodiment of an estimation worksheet/letter.

DETAILED DESCRIPTION OF THE INVENTION

Figure 1:
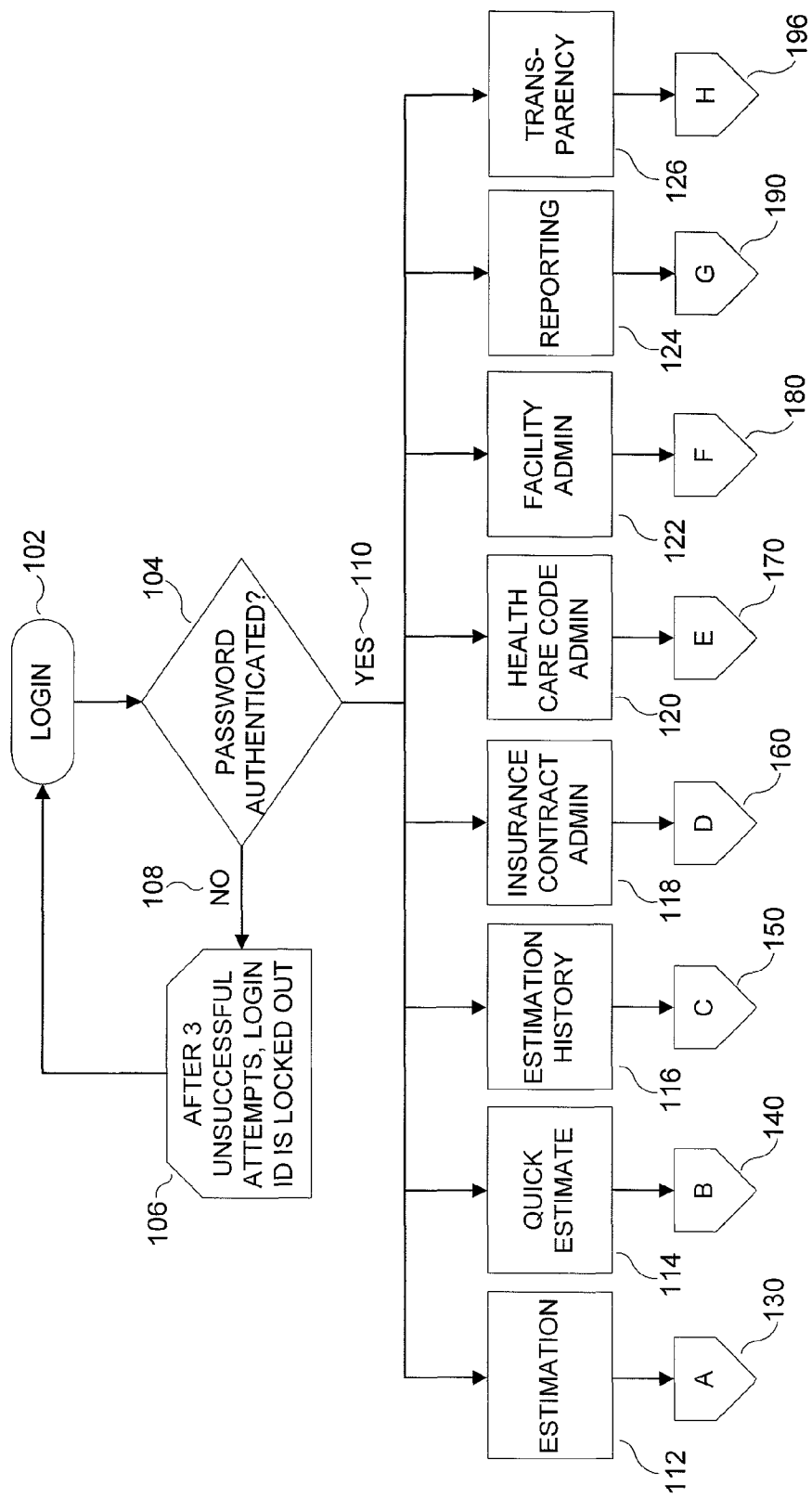
FIG. 1 is an upper level flow chart of the operation of an embodiment of an insurance estimation system.

FIG. 1 is an upper level flow chart 100 of the operation of an embodiment of an insurance estimation system. A user may begin working in the insurance estimation system 100 by logging in 102. After logging in, the system 100 authenticates the password 104. If the password is not authenticated 108, the system 100 returns to the login 102. If a there are three unsuccessful login attempts, the login ID may be locked out 106. A person experienced in the art may decide that security is not necessary and not include any login process in the system 100. A person experienced in the art may also decide that a different number of login attempts before being locked out is appropriate. A person experienced in the art may further vary how long a user ID is locked out, potentially selecting a time frame of only a few seconds all the way up to permanently locking out the user ID that failed to login correctly. Access to all functions (112, 114, 116, 118, 120, 122, 124, 126) of the insurance estimation system 100 may be achieved with role based security assigned to the user's ID. Thus, which areas a user may be permitted to access may be assigned to each individual user, to all users at once, or to groups of different classifications of users. Sometimes, access may be permitted to read data, but not to edit data. A person familiar with the art may also be able to apply other types of role based security features to the estimated insurance system.

Once the user has logged in correctly 110, the user may access one of a number of processes available in the insurance estimation system 100. The user may select to perform an estimation 112, which will take the user to a more detailed flow chart of the estimation process via off page connector A 130 and described further with respect to FIG. 2. The user may select to perform a quick estimate 114, which will take the user to a more detailed flow chart of the estimation process via off page connector B 140 and described further with respect to FIG. 16. The user may select to review the estimation history 116, which will take the user to a more detailed flow chart of the estimation history process via off page connector C 150 and described further with respect to FIG. 17. The user may select to perform insurance contract administration 118, which will take the user to a more detailed flow chart of the insurance contract administration process via off page connector D 160 and described further with respect to FIG. 18. The user may select to perform health care code administration 120, which will take the user to a more detailed flow chart of the health care code administration process via off page connector E 170 and described further with respect to FIG. 23. The user may select to perform facility administration 122, which will take the user to a more detailed flow chart of the facility administration process via off page connector F 180 and described further with respect to FIG. 24. The user may select to configure, display or deliver a report 124, which will take the user to a more detailed flow chart of the reporting process via off page connector G 190 and described further with respect to FIG. 25. The user may select a transparency path 126 to view procedure data, which will take the user to a more detailed flow chart of the transparency path process via off page connector H 196 and described further with respect to FIG. 26.

The insurance estimation system 100 may be implemented on a computer system as computer software using a variety of technologies. For example, an embodiment may implement the insurance estimation system 100 using Internet interfaces, such as Application Server Page (ASP) technology. Other Internet capable technology may be used as well. In another embodiment, the user may own the software license and provide a networked solution using client-server and/or peer-to-peer technology. In some instances, the insurance estimation system 100 may consist of multiple programs, plug-ins, web services and/or scripts. For instance, a client-server model may consist of a program running on the client computer and another program running on the server computer. For access through a web browser, a program may run on the server and send data to the web browser to display. If desired, plug-in software may be used on or with the web browser to enhance the operation of the system as displayed in the web browser. Many times the insurance estimation system 100 will be utilized at the point-of-service for the health care product/service and the technology implementation will need to accommodate use at the health care point of service. Other software and/or software distribution technologies may be used to create, run, and/or deliver the insurance estimation system 100 to the end user.

One skilled in the art may recognize that, as with most computer systems, computer software may run one or more computers within the computer system, such as programs running on the client computer and the server computer for a client-server system. Data entered describing the facility, patient, treatment, insurance, etc. may be stored on computer readable storage media. Likewise, the insurance estimation system 100 software itself may be stored on computer readable storage media. One skilled in the art may recognize that computer readable storage media may be comprised of one or more technologies, depending on the desires of the software developer. For instance, computer readable storage media may include, but is not limited to: hard disk drives, network connected data storage systems, flash drives, memory circuitry, and other computer readable data storage. Even within the various categories of computer readable storage media, there may be a wide variety of sub-categories. For instance, memory circuitry may include, but is not limited to: RAM, ROM, EPROM, flash, and many other types of memory circuitry technologies. Multiple types of computer readable storage media may be utilized to implement the insurance estimation system. For example, a software developer may first put data entered into RAM and later write the same data to a hard disk for more permanent storage.

Figure 2:
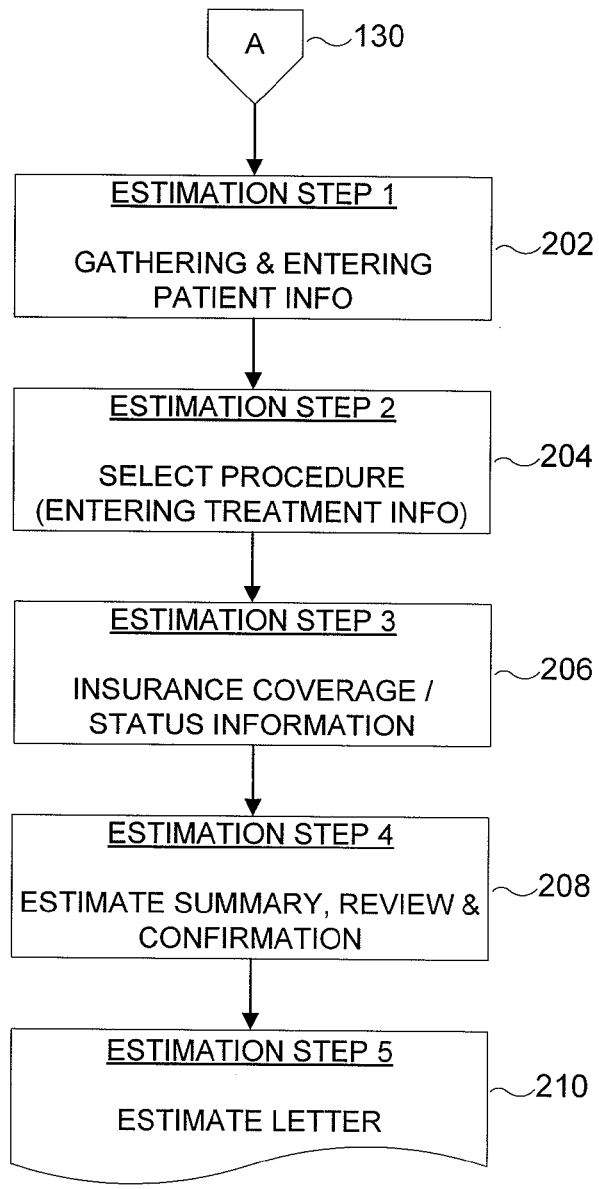
FIG. 2 is a middle level flow chart of the operation of the estimation path of an embodiment of the overall insurance estimation system.

FIG. 2 is a middle level flow chart 200 of the operation of the estimation path 112 of an embodiment of the overall insurance estimation system 100. Access to the steps (202, 204, 206, 208, 210) of the estimation path 112 may be restricted via role based security. After the user has selected the process of creating an estimate 112, the estimation process 112 moves to the first estimation step 202 via off page connector A 130. At estimation step number one (202), the user collects and enters information about the health care patient. At estimation step number two (204), the user selects a healthcare procedure and enters treatment information for the health care patient. At estimation step number three (206), the user collects and enters information about the benefits, coverage and status of the health care patient's health insurance. At estimation step number four (208), the user receives an estimate summary and reviews/confirms the validity of the estimate calculation. At estimation step number five (210), the user causes an estimate letter to be created. The estimate letter may be created and viewed in a variety of formats. Notable formats for the estimate letter include: a hard copy printed out and available to the user, a screen display of the estimate letter, and/or an e-mail version of the estimate letter. The estimate letter may be used by the system user for internal purposes, or the estimation letter may be given to the health care patient and/or the insurance company/companies involved in the health care transaction. The letter may be given to the health care patient to facilitate payment of the estimated patient payable portion of the costs for the health care procedure prior to the time the insurance company performs the final calculations for the health care procedure. The estimate letter 210 and/or estimate summary 208 may include results for treatment related amounts, including but not limited to: the overall total estimated treatment costs, an estimated patient payable portion of the treatment costs/allowable amount due directly from the health care patient, and an estimated insurance company portion of the treatment costs/allowable amount due from the insurance company.

The health care provider may use the estimate letter to request payment of the estimated portion of treatment costs/allowable amount due to the health care provider from the health care patient prior to receiving final calculations of the division of payment from the insurance company. The health care provider may also work with loan companies to provide a loan to the health care patient for the portion of the treatment costs/allowable amount due from the health care patient. To provide the loan through a third party, the insurance estimation system may provide access to at least one third party loan company for the health care patient. The third party loan company or companies may be provided the estimation letter/report to determine the principal amount for the loan based on the patient payable portion of the treatment costs/allowable amount. Privacy laws in lending may require that the estimation letter contain only a patient payable amount and not a description of the treatment in order to avoid any potential improper use of the patient's diagnosis when qualifying the loan. The loan company may collect other information about the health care patient as necessary to perform a loan qualification process for the health care patient. The proceeds of the loan from the third party may be given directly to the health care provider as payment for the health care product/service. If desired, the health care provider may also provide the loan for the patient payable portion of the treatment costs/allowable amount directly to the health care patient and not use a loan company. The loan process for a loan directly from the health care provider may go through the same steps of obtaining the loan amount from a third party lender including obtaining the estimation letter, qualifying the health care patient for the loan, and utilizing the proceeds of the loan to pay the health care provider the estimated patient payable portion of the estimated treatment costs/allowable amount. Loans, either from a third party or from the health care provider, may be automated such that the interaction necessary to go through qualification and gain approval for the loan is performed via a computerized system that permits the loan to be approved without manual evaluation of the loan application data.

Actual payment of the estimated patient payable portion of the estimated treatment costs/allowable amount may be requested at a time substantially prior to the time the insurance company makes the final calculations to determine the final treatment costs/allowable amount and the final division of payments due from the health care patient and the insurance company, including a time prior to rendering the health care product/service to the patient. For instance, the health care provider may bill the health care patient for the estimated patient payable portion of the estimated treatment costs/allowable amount prior to providing the desired health care product/service to the health care patient. Asking for payment prior to providing the product or service is especially useful in non-emergency situations when a delay in the receipt of the health care product/service does not present serious risks to the health of the patient. In order to improve customer relations, providing the estimation letter to the patient prior to providing the health care product/service may be done as a courtesy to the patient in order to give the patient early notification of the patient payable amount that will be due from the patient. In other situations, the patient may be billed for the estimated patient payable portion of the estimated treatment costs/allowable amount prior to the time the health care product/service is rendered to the health care patient, prior to the health care patient being discharged from the health care facility that provided the health care product/service, and/or at a time prior to the final calculations of the division of treatment costs/allowable amount is made available by the insurance company. If the final treatment costs/allowable amount and/or portions of treatment costs/allowable amount are either over or under the estimated treatment costs/allowable amount, the health care provider may refund excess payments or bill for additional payments due, as needed. In another embodiment, the patient may be requested to sign a contract stating that the patient will pay for the estimated patient portion of the treatment costs/allowable amount within a specified period of time. This may be particularly helpful for emergency and/or critical health care situations where it is not prudent to wait for pre-payment prior to providing the health care product/service to the patient since waiting to provide the health care product/service may be substantially detrimental to the health of the patient. The current law titled the "Emergency Medical Treatment and Active Labor Act" (EMTALA) addresses many issues regarding providing emergency medical treatment and the EMTALA and/or other laws may define how and when payments may be requested and received for rendering emergency medical services.

Figure 3:
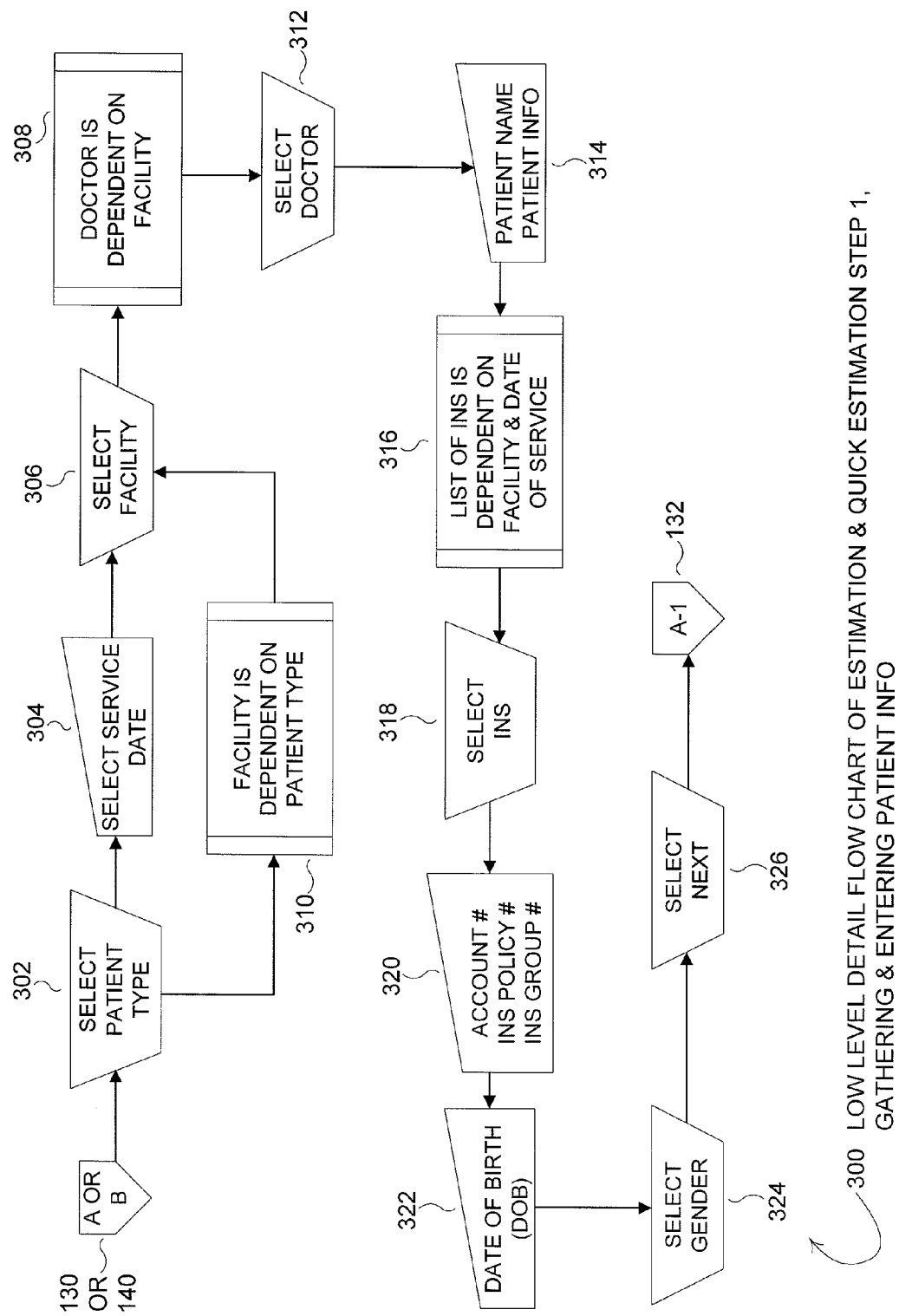
FIG. 3 is a low level flow chart of the operation of estimation step number one (gathering and entering patient information) of the estimation and quick estimation paths of an embodiment of the overall insurance estimation system.

FIG. 3 is a low level flow chart of the operation of estimation step number one (202, 1602) (gathering and entering patient information) of the estimation 112 and quick estimation 114 paths of an embodiment of the overall insurance estimation system 100. FIG. 3 discloses, in greater detail than is given in FIG. 2, the intricacies of estimation step one (202) of gathering and entering patient information. After the user has selected the process of creating an estimate 112, the estimation process 112 continues via off page connector A 130. At step 302, the user is asked to select a patient type for the health care patient. The patient type may be selected from a predefined list of patient types. Some potential patient types include, but are not limited to: pre-inpatient, pre-inpatient obstetric, in-house, and outpatient. An embodiment may further provide independently addressable role based security access to the patient type selection 318. At step 304 the user selects the service date for when the health care patient will begin to receive the health care product/service. In parallel with selecting the service date 304, logic to determine if the list of facilities is dependent on the patient type 310 is run with the selected patient type. If the list of facilities is dependent on the patient type 310, only the available facilities for the selected patient type will be available for selection in step 306. At step 306, the user is asked to select a facility from a predefined list of facilities. The predefined list of facility selections may be maintained using the facility administration 122 portion of the insurance estimation system 100 disclosed in further detail with respect to FIG. 24. Each facility may have unique estimation calculations based on historical treatment costs at the facility as well as other cost factors that may affect a particular facility. An embodiment may further provide independently addressable role based security access to the facility selection at step 306. At step 308, logic to determine if a list of available doctors 308 is dependent on the selected facility is run with the selected facility. If the list of doctors is dependent on the selected facility 308, only the available doctors for the selected facility will be available for selection in step 312. At step 312, the user is asked to select a doctor from a predefined list of doctors. In some embodiments, the doctor providing the service operates the insurance estimation system 100 so the providing doctor is pre-selected and the steps of selecting a doctor 308, 312 are unnecessary.

At step 314, the user enters the patient's name and other patient information. Patient information may include, but is not limited to: patient name, patient age, and the patient account number with the health care provider. At step 316, the insurance estimation system 100 may limit the list of acceptable insurance companies based on the selected facility and date of service. Based on the available insurance list from the logic of step 316, at step 318, the user is asked to select an insurance company. In various embodiments, if the patient does not have insurance that is accepted at the facility for the specified service date, the system may default to a self-insured status such that the patient interacts with the insurance company directly. Limiting the list of insurance companies may be necessary for the health care provider to ensure that the health care patient is using insurance accepted by the health care provider and/or facility. Health care providers may have contracts with insurance companies that expire or come into effect at various dates, so only currently valid insurance companies may be listed as well, which may be determined by the date of service. For some embodiments, the date of service may not be necessary if contract validity dates are not taken into account. Further, different facilities may have relationships with different insurance companies and/or different contractual rates for the same insurance company. Thus, limiting the insurance company selection to only those insurance companies that have an active contract on the date of service with the health care provider and/or the facility where the health care product/service is to be provided ensures that the estimation of treatment costs may properly take into account contractual details with the insurance company, including restrictions as to allowable amounts that may be charged for a procedure. If an insurance company is not available, it may be necessary for the health care patient to pay the entire cost for the health care product/service and to independently work with the insurance company to be reimbursed for the portion of costs that should be covered by the insurance company.

At step 320, the user enters the insurance policy information. Various embodiments may ask the user to enter portions of the patient information, such as the account number with the health care provider, at step 320 as well. Insurance policy information may include, but is not limited to: policy number and group number. At step 322, the user enters the date of birth for the health care patient. At step 324, the user selects the gender of the health care patient. At step 326, the user is asked to select "Next" to move on to additional data entry displays. From step 326 the flow chart 300 connects to FIG. 4 (a first embodiment) or FIG. 5 (an additional embodiment) using off page connector A-1 (132).

The process described with respect to FIG. 3 also applies to the quick estimate path 114 of an embodiment of the overall insurance estimation system 100. As for the estimation path 112, FIG. 3 discloses, in greater detail than is given in FIG. 16, the intricacies of quick estimate step one (1602) of gathering and entering patient information. After the user has selected the process of obtaining a quick estimate 114, the quick estimate process 114 continues via off page connector B 140. The quick estimate path 114 may be substantially the same as the normal estimation path 112 except that the quick estimate path 114 may skip estimation path 112 steps three (206), four (208), and five (210). Thus, the quick estimate path is less detailed, but able to provide a fast estimate when a quick, "ball park" estimate is desired. For some embodiments, the first two steps (202, 204) of the estimation path 112 and the quick estimate path 114 may be substantially the same for both normal 112 and quick 114 estimation paths.

Figure 4:
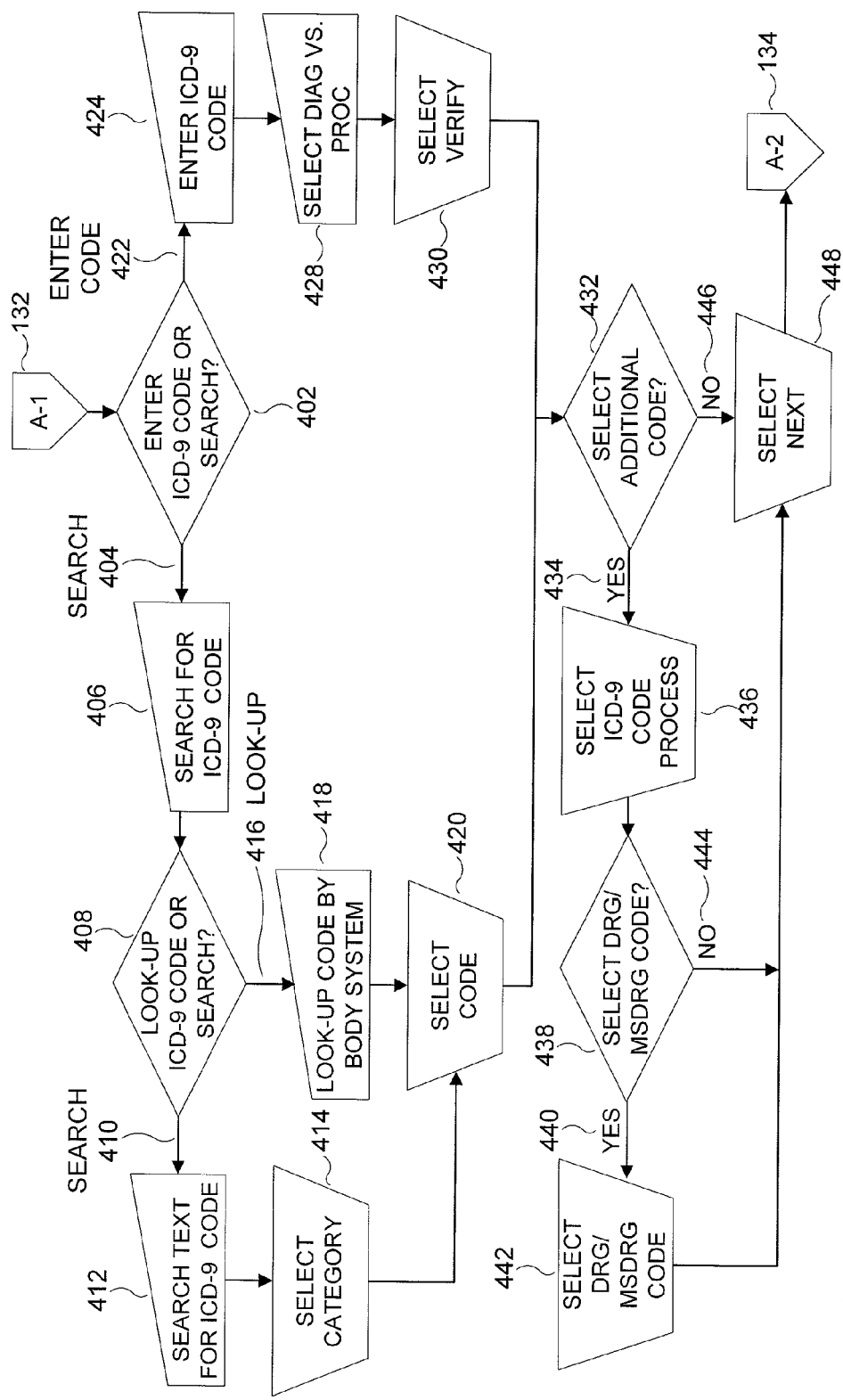
FIG. 4 is a low level flow chart of the operation of estimation step number two (selecting a procedure/entering treatment information) of the estimation path of one embodiment of the overall insurance estimation system.

FIG. 4 is a low level flow chart 400 of the operation of estimation step number two (204) (selecting a procedure/ entering treatment information) of the estimation path 112 of one embodiment of the overall insurance estimation system 100. Continuing from off page connector A-1 (132), the user is prompted to enter at least one International Classification of Diseases (ICD) code or search for the appropriate ICD code(s) at step 402. In other embodiments, the selection of the ICD code(s) may be a selection of any available health care codes. Examples of other health care codes include, but are not limited to: Diagnostic Related Groups (DRG) codes, Medical Severity Diagnostic Related Groups (MSDRG) codes, Current Procedural Terminology (CPT®) codes, Healthcare Common Procedure Coding System (HCPCS) codes, health care facility specific codes, doctor specific codes, and proprietary health care codes. CPT is a registered trademark of the American Medical Association. Further, the ICD codes may include ICD codes from a particular revision of the ICD codes or from multiple ICD code revisions. For instance, the ICD codes shown in FIG. 4 are from revision 9 of the ICD codes, commonly referred to as ICD-9. The ICD codes may also be broken down into many sub-classes and only certain important sub-classes may be included in the available list of health care codes. Two important sub-classes of the ICD-9 codes are the diagnosis (Diag) and procedure (Proc) sub-classes. In some cases codes from multiple systems may be used together. For instance, an embodiment may utilize ICD codes as a top-level description for a health care product/service, but provide a limited list of more detailed DRG/MSDRG codes based on the selected ICD codes. Relationships between different health care codes may be created using historical information collected for past procedures that relate a health care code, such as an ICD-9 code, to a limited number of potentially more detailed codes, such as one or more DRG/MSDRG codes. The specific relationship between two health care code systems, such as ICD-9 and DRG/MSDRG, may be further enhanced by using weighted averages of the occurrence of one code occurring when an upper level code is named. By using a weighted average, the probability of lower level codes occurring may be compared to other lower level codes such that the list of lower level codes is limited to lower level codes above a preset weighted average and/or probable lower level codes may be put in the order of most likely occurrence.

Estimated costs for various procedures may also be based on the historical costs for a facility and/or health care provider for particular procedures coded with a particular health care code. Factors that may be included in determining the estimated cost for a particular health care procedure include, but are not limited to: average price, median price, average length of stay, median length of stay, average implant/material cost, and median implant/material cost. Cost estimates may also be enhanced by weighted averages. If different procedures or products are provided under the same health care code, the estimated cost for the health care code may take into account each of the potential health care procedures or products provided under the health code weighted for the percentage of the total history attributable to each potential health care procedure or product provided under the selected health care code. The estimated costs may also be based in part on the geographic practice cost index (GPCI) or the specialty/proprietary coding systems. Performing estimates based on the health care codes permits data entry personnel without extensive medical training to enter the health care codes based on the notes from the physician, nurse, or other health care professional. Thus, estimates may be created quickly and easily by a relatively inexpensive data entry employee rather than requiring the time from a high cost health care professional employee.

For the embodiment described in FIGS. 3 and 4, if the user selects the search option 404 at step 402, the user is then shown a user interface for different search options at step 406. At step 408 the user is prompted to select to either look-up the ICD-9 health care code or to perform a search of the ICD-9 code text. If the user selects to search the text 410, then a display for searching by text is shown to the user at step 412. At step 414 the user selects the text category to search. The potential text categories to search may include, but are not limited to: code numbers, code name, and/or code description. Searching by the code numbers may also permit the user to select a range of code numbers to view. The ICD codes may also be narrowed by the selected sub-class, such as by diagnosis or procedure codes, or by both sets of sub-class codes together. After step 414, the user is presented a list of ICD-9 health care codes that satisfy the search criteria. At step 420 the user selects an ICD-9 health care code from the list of ICD-9 health care codes produced by steps 412 and 414.

If the user opts to look-up 416 the ICD-9 health care code at step 408, the user is then prompted to select a body system group to narrow the search for the ICD-9 code at step 418. After narrowing the list of potential ICD-9 codes to those codes that are pertinent for a particular body system, the user then selects an ICD-9 health care code from the list of ICD-9 codes produced in step 418.

If the user selects to enter the ICD-9 health care code 422 at step 402, then the user is shown a data entry screen to enter the ICD-9 code at step 424. After entering the ICD-9 code, the user is asked to select whether the entered code is a diagnosis sub-class code or a procedure sub-class code at step 428. At step 430, the user selects to verify the health care code and the system verifies that the code entered is a valid ICD-9 health care code.

Depending on the user selections, either step 420 or step 430 leads to step 432. At step 432 the user is asked whether the user wishes to select an additional code. If the user wants to select an additional ICD-9 code 434, the user selects another ICD-9 code at step 436 using the process to search or enter an ICD-9 code described above in steps 402 to 430. At step 438 the user is prompted to decide whether to select a DRG/MSDRG code to narrow the description of the health care product/service more than the selected ICD-9 codes permits. If the user decides to select a DRG/MSDRG code 440, the user is asked to select at least one DRG/MSDRG code from the list of DRG/MSDRG codes related to the selected ICD-9 codes at step 442. After selecting the DRG/MSDRG code(s), the user proceeds to step 448. Likewise, if the user had decided not to enter a DRG/MSDRG code 444 or the user had decided not to select an additional ICD-9 code, the user would also proceed to step 448 with out any intervening steps. At step 448, the user is prompted to select "Next" to move on to the next step in the estimation process. The next step in the estimation process is linked to using off page connector A-2 (134) to move to estimation step three (206), described in more detail with respect to FIG. 5. Note that the number of additional ICD-9 codes permitted for other embodiments may range from one additional code to any number of additional codes desired by the system developer. Similarly, the number of DRG/MSDRG codes selected may range from a single DRG/MSDRG code to as many DRG/MSDRG codes as desired by the system developer. Other data may also be used to narrow the list of potential health care codes available for selection. For instance, pertinent patient information may be used to narrow the potential health care codes to codes that are appropriate for the health care patient. The patient's gender may be used to eliminate health care codes that only apply to the opposite sex of the health care patient. The patient's age may be used to limit the health care codes to health care codes that are appropriate for the age of the patient. The patient's age and gender may be combined to eliminate even more health care codes. A patient's medical history may also be used to highlight or eliminate certain health care codes as well.

Embodiments may handle different patient types using differing health care code systems and different methodologies. For instance, the health care code system and methodologies for handling a pre-inpatient, pre-inpatient obstetric, and outpatient patient type for certain embodiments are described below with respect to FIGS. 28, 29, and 30, respectively.

FIG. 5 is a low level flow chart 500 of the operation of estimation step number two (204, 1604) (selecting a procedure/entering treatment information) of the estimation 112 and quick estimation 114 paths of an additional embodiment of the overall insurance estimation system 100. At step 502, the system evaluates the patient type. If the patient type is inpatient 504, then the system moves to step 506 and evaluates whether the health care procedure is for a baby. If the health care procedure is for a baby 508, then the system runs the logic for a baby 510. An embodiment of the logic 510 for a baby is given below in the disclosure with respect to FIG. 6. At the conclusion of the baby logic 510, the system asks the user to select next 512 to move on to the next step via off page connector A-2 (134) for the estimation logic path 112, or the system performs quick estimate calculations with the given information for the quick estimate path 114 and ends the process 134.

If, at step 506, the health care procedure is not for a baby 540, then, at step 542, the system asks the user whether the user wants to enter an ICD-9 code or search for a code. If the user chooses to enter an ICD-9 code 544, then, at step 546, the user enters the ICD-9 code. At step 548, the user enters whether the ICD-9 code is a diagnosis code or a procedure code. At step 550, the user verifies the entered ICD-9 code and moves to step 552 to decide whether or not to enter an additional code. If, at step 542, the user chooses to search 568 for a code, then the system performs logic to search for the ICD-9 code 570. An embodiment of the logic 570 for searching for an ICD-9 code is given below in the disclosure with respect to FIG. 8. At the conclusion of the ICD-9 code search logic 570, the system moves step 552 to determine if the user would like to enter additional codes. If, at step 552, the user desires to enter additional codes 554, then the user may select an additional ICD-9 code at step 556. Step 556 may perform the same type of operations as performed at step 542 and beyond to select an ICD-9 code. From step 556, the user is again asked if it is desired to select more codes at step 558. If, at step 558, the user chooses to select more codes 560, then the user may select an additional ICD-9 code at step 562. As with step 556, step 562 may perform the same type of operations as performed from step 542 and beyond to select an ICD-9 code. In the embodiment shown in FIG. 5, the user is only asked to add additional ICD-9 codes twice. Other embodiments may vary the number of times to ask a user to add additional codes. Some embodiments may recursively continue asking for additional codes until the user affirmatively chooses to not add any more additional codes. If, at steps 552 and/or step 558, the user selects to not add any additional codes 564, 566, then the system moves to step 512. After entering additional codes at step 562, the system also moves to step 512. At step 512, the system asks the user to select next to move on to the next step via off page connector A-2 (134) for the estimation logic path 112, or the system performs quick estimate calculations with the given information for the quick estimate path 114 and ends the process 134.

If, at step 502, the patient type is outpatient 514, then the system asks the user whether to enter a CPT code or search for codes at step 516. If, at step 516, the user chooses to search 518, then the user is asked whether to search for a CPT code or an ICD-9 code at step 520. If, at step 520, the user chooses to search for an ICD-9 code 522, then the system would perform logic to search for the ICD-9 code 524. An embodiment of the logic 524 for searching for an ICD-9 code is given below in the disclosure with respect to FIG. 8. At the conclusion of the ICD-9 code search logic 524, the system moves to step 526 to determine if the user would like to enter additional codes. If, at step 520, the user chooses to search CPT codes 530, then the system would perform logic to search for the CPT code 532. An embodiment of the logic 532 for searching for CPT code is given below in the disclosure with respect to FIG. 9. At the conclusion of the CPT code search logic 532, the system moves step to 526 to determine if the user would like to enter additional codes. If, at step 516, the user chooses to enter the CPT code 534, then the user would enter the CPT code at step 536. After entering the CPT code 536, the system moves to step 526 to determine if the user would like to enter additional codes. If, at step 526, the user chooses to enter additional codes, then the system returns to step 516 and repeats the process described above with respect to step 516 and the following processes. If, at step 526, the user chooses not to enter additional codes 538, then the system moves to step 512. At step 512, the system asks the user to select next to move on to the next step via off page connector A-2 (134) for the estimation logic path 112, or the system performs quick estimate calculations with the given information for the quick estimate path 114 and ends the process 134.

FIG. 6 is a low level flow chart 600 of the operation of the baby logic 510 for estimation step number two (204, 1604) of the estimation 112 and quick estimation 114 paths of the additional embodiment shown in FIG. 5. At step 602, the system asks whether the delivery method for the baby will be normal 604 or c-section 606. For both normal 604 and c-section 606, the delivery method is recorded and the user enters the number of babies at step 608. At step 610, the system asks whether the baby(s) is covered by two insurance policies. If, at step 610, the baby is covered by two insurance policies 612, then the user inputs the mother's birthday at step 614 and the father's birthday at step 616. Steps 614 and 616 feed data to step 618 that evaluates whether the father's birthday is before the mother's birthday. If the father's birthday is not before the mother's birthday 620, then the mother's insurance information from estimation step one (202) is used and the system moves to step 622 where the user selects next to move on to the next step in the estimation process 206 reached via off page connector A-2 (134) to FIG. 11. If, at step 618, the father's birthday is before the mother's birthday 624, then the system moves to step 626 to select which insurance to use. At step 628, the appropriate account and insurance information is entered into the system and the system moves to step 622 where the user selects next to move on to the next step in the estimation process 206 reached via off page connector A-2 (134) to FIG. 11. If at step 610, the baby is not covered by two insurance policies 630, the system moves to step 632 to determine if the insurance policy for the baby is the same as for the mother. If, at step 632, the insurance policy for the baby is not the same as the insurance policy for the mother, then the system moves to step 626 to select which insurance to use. At step 628, the appropriate account and insurance information is entered into the system and the system moves to step 622 where the user selects next to move on to the next step in the estimation process 206 reached via off page connector A-2 (134) to FIG. 11. If, at step 632, the baby's insurance is the same as the mother, then the mother's insurance information from estimation step one (202) is used and the system moves to step 622 where the user selects next to move on to the next step in the estimation process 206 reached via off page connector A-2 (134) to FIG. 11. Note that for a quick estimate 114, step 622 calculates the quick estimate and ends the quick estimation process 114 at off page connector A-2 (134).

FIG. 7 is a low level flow chart 700 of the operation of the Current Procedural Terminology (CPT®) code search logic 532 for estimation step number two (204, 1604) of the estimation 112 and quick estimation 114 paths of the additional embodiment shown in FIG. 5. At 702, ICD-9 Diagnosis codes are stored for use by the overall estimation system 100. The ICD-9 Diagnosis codes data store 702 supplies data to inputs for the patient age 708 and the active codes at the facility 716. At 704, ICD-9 Procedure codes are stored for use by the overall estimation system 100. The ICD-9 Procedure codes data store 704 supplies data to inputs for patient age 708, patient gender 710, health care facility 712, and active codes at the health care facility 714. The patient age 708, patient gender 710, health care facility 712, and the active codes at the health care facility 714 information are combined together 716 for use as filters to search results of the ICD-9 Diagnosis and Procedure codes.

At step 718, the user enters the CPT text that the user wishes to search. At step 720, the user may select optional criteria of the CPT code type. At step 722, the user searches for the CPT code. The search logic 722 obtains data from the combination filter 716 to help filter codes and locate potential CPT codes related to the user entered search text 718.

FIG. 8 is a low level flow chart 800 of the operation of the International Classification of Diseases (ICD) code search logic 524, 570 for estimation step number two (204, 1604) of the estimation 112 and quick estimation 114 paths of the additional embodiment shown in FIG. 5. At 802, ICD-9 Diagnosis codes are stored for use by the overall estimation system 100. The ICD-9 Diagnosis codes data store 802 supplies data to inputs for the patient age 808 and the active codes at the facility 816. At 804, ICD-9 Procedure codes are stored for use by the overall estimation system 100. The ICD-9 Procedure codes data store 804 supplies data to inputs for patient age 808, patient gender 810, health care facility 812, and active codes at the health care facility 814. The patient age 808, patient gender 810, health care facility 812, and the active codes at the health care facility 814 information are combined together 816 for use as filters to search results of the ICD-9 Diagnosis and Procedure codes.

At step 818, the user enters the ICD-9 code or text that the user wishes to search. At step 820, the user selects whether the searched code is a diagnosis code or a procedure code. At step 822, the user may select optional criteria of the ICD-9 code type. At step 824, the user searches for the ICD-9 code. The search logic 824 obtains data from the combination filter 716 to help filter codes and locate potential ICD-9 codes related to the user entered search text 818.

FIG. 9 is a Venn diagram 900 of the relationship between Diagnostic Related Groups (DRG)/Medical Severity Diagnostic Related Groups (MSDRG), ICD Diagnosis, and ICD Procedure codes of FIG. 8. For the Venn diagram 900 of FIG. 9, there are three potential knowledge areas, ICD-9 Diagnosis codes 902, ICD-9 Procedure codes 904, and DRG and MS-DRG codes 906. Using historical patient encounter data for a facility, group of facilities, and/or over all potential facilities, relationships of ICD-9 Diagnosis codes 902, ICD-9 Procedure codes 904, and DRG/MSDRG codes are found so that the relationship may be utilized as part of the search filter 816 described in the disclosure with respect to FIG. 8. The D-P area 908 describes an overlapping relationship between ICD-9 Diagnosis 902 and Procedure 904 codes. The D-DRG area 910 describes an overlapping relationship between ICD-9 Diagnosis codes 902 and DRG/MSDRG codes 906. The P-DRG area 912 describes an overlapping relationship between ICD-9 Procedure codes 904 and DRG/MSDRG codes 906.

FIG. 10 is a Venn diagram 1000 of the relationship between CPT/Healthcare Common Procedure Coding System (HCPCS), ICD Diagnosis, and ICD Procedure codes of FIG. 7. For the Venn diagram 1000 of FIG. 10, there are three potential knowledge areas, ICD-9 Diagnosis codes 1002, ICD-9 Procedure codes 1004, and CPT/HCPCS codes 1006. Using historical patient encounter data for a facility, group of facilities, and/or over all potential facilities, relationships of ICD-9 Diagnosis codes 1002, ICD-9 Procedure codes 1004, and CPT/HCPCS 1006 codes may be found so that the relationship may be utilized as part of the search filter 716 described in the disclosure with respect to FIG. 7. The D-P area 1008 describes an overlapping relationship between ICD-9 Diagnosis 1002 and Procedure 1004 codes. The D-CPT area 1010 describes an overlapping relationship between ICD-9 Diagnosis codes 1002 and CPT/HCPCS codes 1006. The P-CPT area 1012 describes an overlapping relationship between ICD-9 Procedure codes 1004 and CPT/HCPCS codes 1006.

Figure 11:
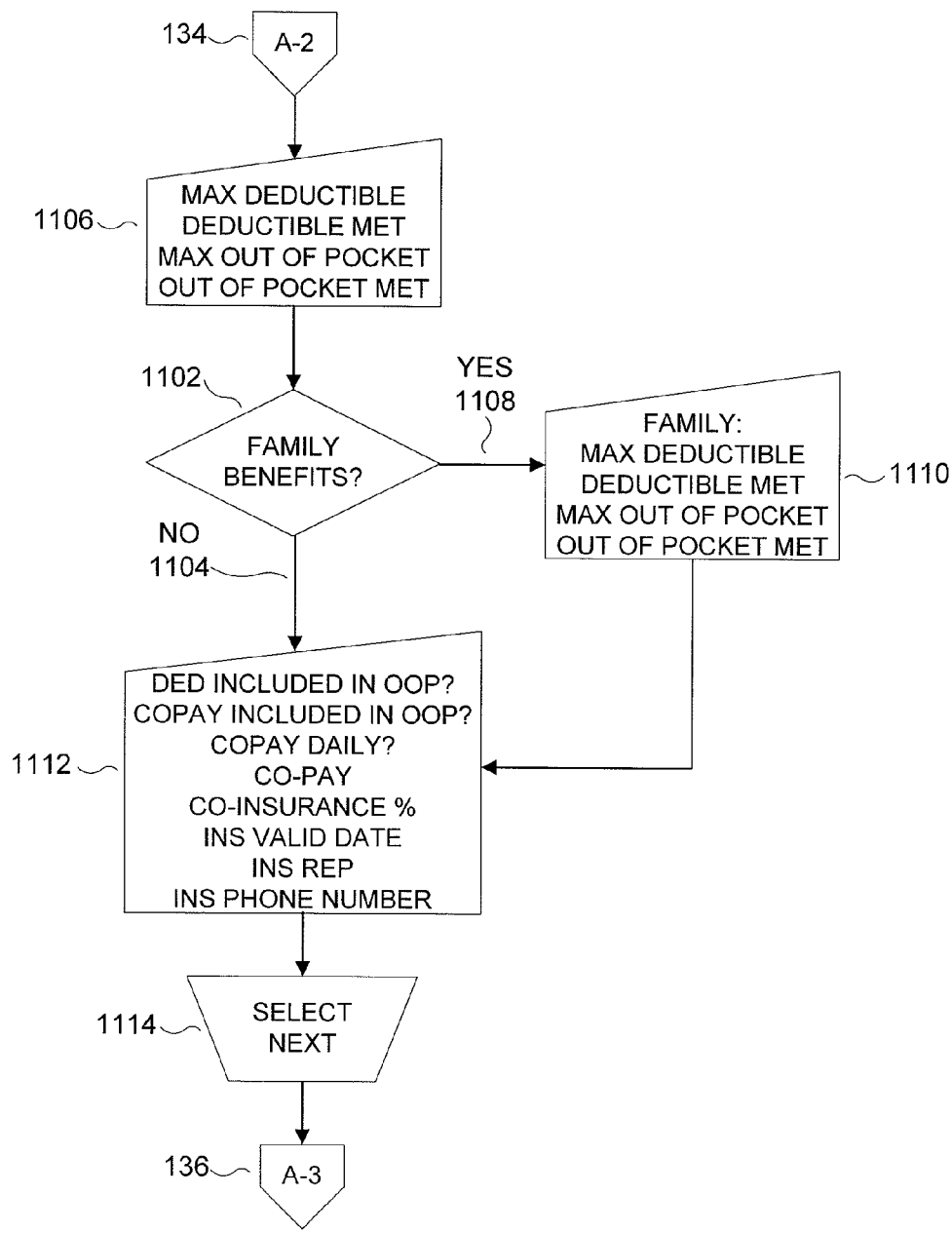
FIG. 11 is a low level flow chart of the operation of estimation step number three (gathering and entering insurance benefits information) of the estimation path of an embodiment of the overall insurance estimation system.

FIG. 11 is a low level flow chart 1100 of the operation of estimation step number three (206) (gathering and entering insurance benefits information) of the estimation path 112 of an embodiment of the overall insurance estimation system 100. Continuing from off page connector A-2 (134), the user is prompted to enter insurance benefits (coverage/status) information for the health care patient at step 1106. At step 1102, the system asks whether there are family benefits for the insurance for the health care patient. If, at step 1102, there are family benefits 1108, then at step 1110, the user is prompted to enter insurance benefits (coverage/status) information for the family benefits portion of the health care patient's insurance coverage. From step 1110, the system proceeds to step 1112. If, at step 1102, there are no family benefits 1104, then the system proceeds directly to step 1112. For both individual 1106 and family benefits 1110, the user may enter insurance benefits information including, but not limited to: maximum deductible, deductible met, out of pocket max, and/or out of pocket met. Both steps 1108 and 1110 move to step 1112 where the user may enter additional insurance benefits information including, but not limited to: an is deductible included in the out of pocket (OOP) amounts indicator, an is co-pay included in the out of pocket (OOP) amounts indicator, an is co-pay charged daily indicator, a co-pay amount, a co-insurance percentage value, an insurance valid until date, an insurance representative name, and a phone number for the insurance company. Once insurance benefits/status information is entered in steps 1102-1112, the user may accept the entered information by selecting "Next" at step 1114. From step 1114 the flow chart 1100 progresses to off page connector A-3 (136) which links to FIG. 12.

The insurance benefits information may be gathered by calling the insurance company with the insurance policy information and obtaining the current values of the insurance benefits (coverage/status) information. If available, the insurance estimation system 100 may access the information through an electronic data connection that provides the insurance benefits information and is made available by the insurance company. The electronic data connection may be made available using Internet technology, other networking technologies, and/or any other electronic communication technologies designated by the insurance company.

Figure 12:
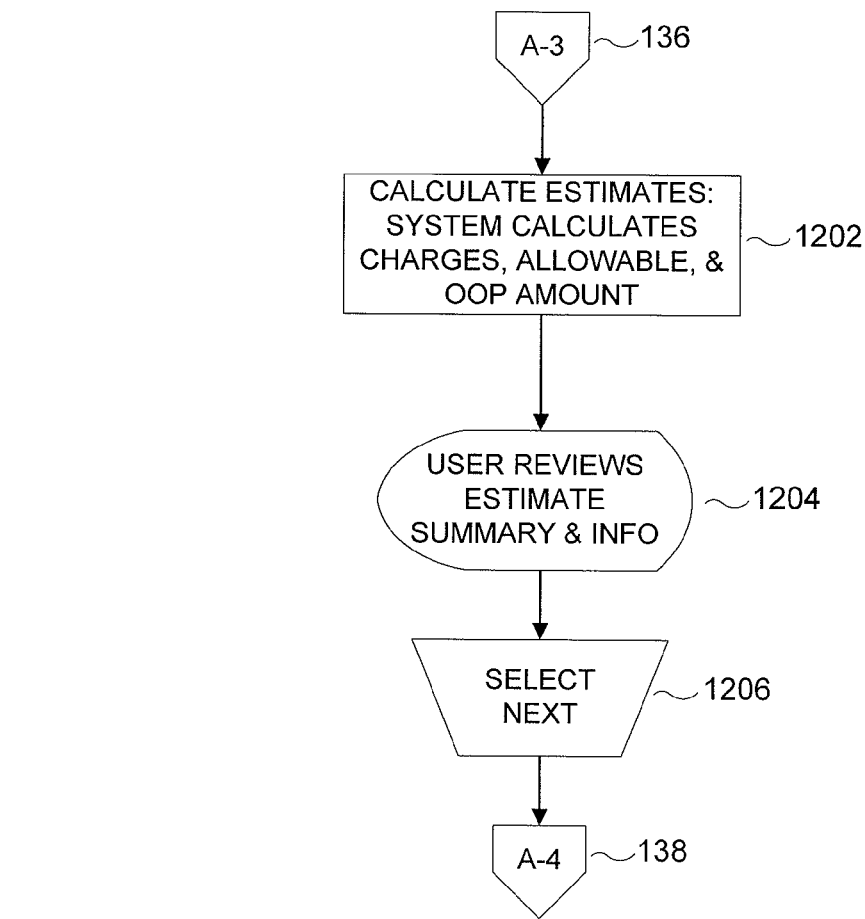
FIG. 12 is a low level flow chart of the operation of estimation step number four (estimate summary, review, and confirmation) of the estimation path of an embodiment of the overall insurance estimation system.

FIG. 12 is a low level flow chart 1200 of the operation of estimation step number four (208) (estimate summary, review and confirm) of the estimation path 112 of an embodiment of the overall insurance estimation system 100. Continuing from off page connector A-3 (136), at step 1202 the system calculates the estimates, including estimates for total charges, allowable amounts, and out-of-pocket amounts. At step 1204, the user reviews a summary of the estimate of the treatment related amounts and the information utilized to obtain the treatment cost estimate. Estimated treatment related amounts may include, but are not limited to: estimated treatment costs, an estimated allowable amount, and/or an estimated patient payable amount. At step 1206 the user selects "Next" to move to the next step. From step 1206 the flow chart 1200 progresses to off page connector A-4 (138) which links to FIG. 13.

Figure 13:
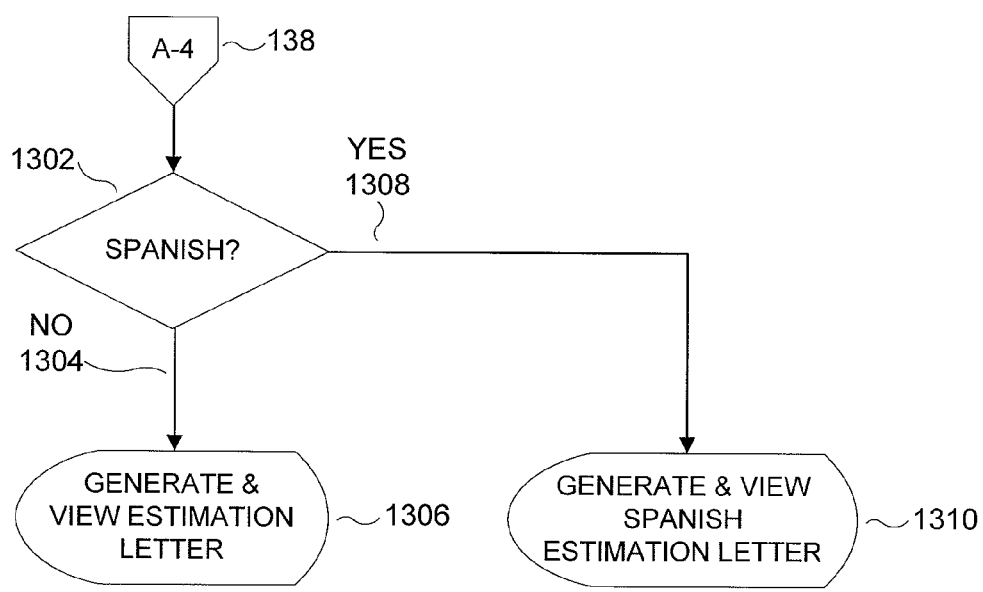
FIG. 13 is a low level flow chart of the operation of estimation step number five (estimate letter) of the estimation path of an embodiment of the overall insurance estimation system.

FIG. 13 is a low level flow chart 1300 of the operation of estimation step number five (210) (estimate letter) of the estimation path 112 of an embodiment of the overall insurance estimation system 100. Continuing from off page connector A-4 (138), at 1302, the system asks if the report is to be in Spanish. Other embodiments may include options for other languages. If, at step 1302, a Spanish language report is not desired 1304, then the system proceeds to step 1306. At step 1306 an English (or other default language) estimate letter is generated and viewed. If, at step 1302, a Spanish language report is desired 1308, then the system proceeds to step 1310. At step 1310 a Spanish language estimate letter is generated and viewed. The estimate letter may be viewed by any interested party, including, but not limited to: the health care provider, the facility, the insurance company, and/or the health care patient.

Figure 14:
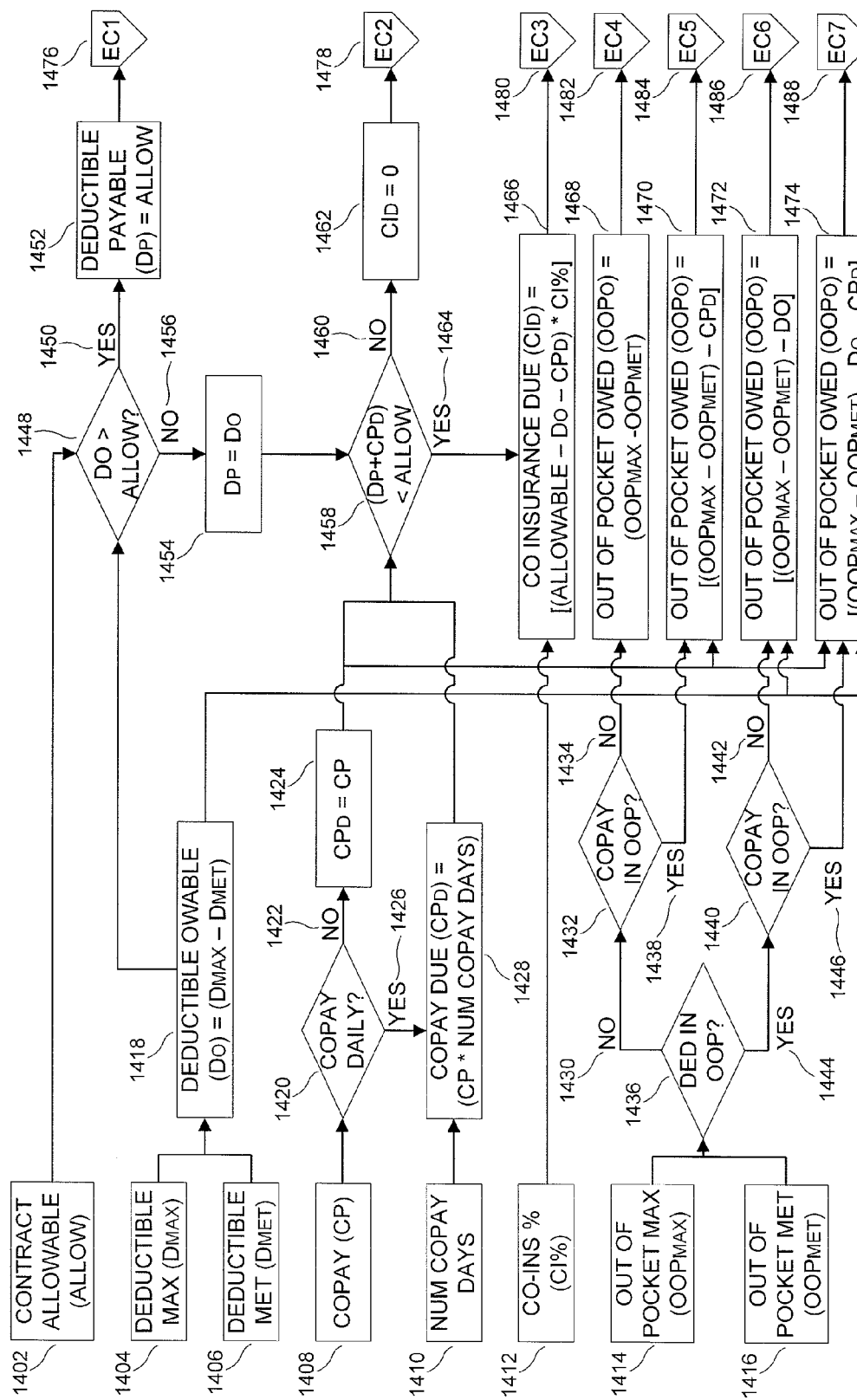
FIG. 14 is page one of a low level flow chart of an estimation calculation for the estimation path of an embodiment of the overall insurance estimation system.

FIG. 14 is page one 1400 of a low level flow chart of an estimation calculation for the estimation path 112 of an embodiment of the overall insurance estimation system 100. Inputs to the estimation calculation may include: a contract allowable amount 1402, a maximum deductible amount (Dmax) 1404, a deductible met amount (Dmet) 1406, a co-pay amount (CP) 1408, a number of co-pay days value 1410, a co-insurance percentage value (CI %) 1412, a maximum out of pocket amount (OOPmax) 1414, and an out of pocket met amount (OOPmet) 1416. Depending on the circumstances of the health care patient's insurance benefits information, the maximum deductible amount (Dmax) 1404, the deductible met amount (Dmet) 1406, the maximum out of pocket amount (OOPmax) 1414, and the out of pocket met amount (OOPmet) 1416 may be obtained from either the individual benefit amounts or the family benefit amounts, as appropriate for the patient and the circumstances. Other inputs include an is co-pay charged daily indicator 1420, an is deductible amount included in the co-pay amounts indicator 1436, and an is co-pay amount included in the out of pocket amounts indicator 1432, 1440. An estimation of the total cost of the health care product/service may be obtained from the historical relationship of the historical costs associated with the designated health care code. If different health care products/services have historically been provided for a health care code, weighted averages of the costs may be used to adjust the estimated cost such that the cost of the most frequent historical health care procedure/service rendered for the health care code carries the greatest weight in the estimate calculation. The contract allowable for a particular health care product/service also plays an important role. The contract allowable for a health care product/service limits the cost that the health care provider or facility may charge for the health care product/service. Therefore, the estimated amount for a health care product/service may be directly linked to the contract allowable for the health care product/service contained in the contract between the insurance company and the health care provider or facility. The number of co-pay days value 1410 may be based on the historical relationship between the selected health care code(s) and the number of days or visits required to treat the patient.

At step 1418 a deductible owable amount (Do) is calculated by subtracting the deductible met amount (Dmet) 1406 from the maximum deductible amount (Dmax) 1404. At step 1420, the is co-pay charged daily indicator is interrogated. If the is co-pay charged daily indicator is false 1422, then, at step 1424, a co-pay due amount (CPd) is set equal to the co-pay amount (CP) 1408. If the is co-pay charged daily indicator is true 1426, then, at step 1428 the co-pay due amount (CPd) is set equal to the co-pay amount (CP) 1408 multiplied times the number of co-pay days value 1410. At step 1466 a co-insurance due amount (CId) is calculated by first subtracting the calculated co-pay due amount (CPd) 1424, 1428 and the calculated deductible owable amount (Do) 1418 from the contract allowable amount 1402. The result of the subtraction calculation is then multiplied times the co-insurance percentage value (CI %) 1412.

At steps 1468, 1470, 1472, and 1474, an out of pocket owed amount (OOPo) is calculated. One of the calculations from steps 1468, 1470, 1472, and 1474 is selected based on the states of the is deductible amount included in the co-pay amounts indicator 1436 and the is co-pay amount included in the out of pocket amounts indicator 1432, 1440. At step 1436 the is deductible amount included in the out of pocket amounts indicator is interrogated. If the is deductible amount included in the out of pocket amounts indicator is false 1430 at step 1436, then the is co-pay included in the out of pocket amounts indicator is interrogated at step 1432. If the is co-pay included in the out of pocket amounts indicator is false 1434 at step 1432, then the calculation for the out of pocket owed amount (OOPo) is obtained from step 1468. If the is co-pay included in the out of pocket amounts indicator is true 1438 at step 1432, then the calculation for the out of pocket owed amount (OOPo) is obtained from step 1470. If the is deductible amount included in the out of pocket amounts indicator is true 1444 at step 1436, then the is co-pay included in the out of pocket amounts indicator is interrogated at step 1440. If the is co-pay included in the out of pocket amounts indicator is false 1442 at step 1440, then the calculation for the out of pocket owed amount (OOPo) is obtained from step 1472. If the is co-pay included in the out of pocket amounts indicator is true 1446 at step 1440, then the calculation for the out of pocket owed amount (OOPo) is obtained from step 1474. Further operations for the out of pocket owed amount calculated by one of steps 1468, 1470, 1472, or 1474 are directed to off page connectors EC4 (1482), EC5 (1484), EC6 (1486), or EC7 (1488), respectively, that link the first page 1400 of the calculation flow chart of FIG. 14 to the second page 1500 of the calculation flow chart of FIG. 15.

At step 1448 the calculated deductible owable amount (Do) 1418 is compared to the contract allowable amount 1402. If the deductible owable amount (Do) 1418 is more than the contract allowable amount 1402, then path 1450 is selected and a deductible payable amount (Dp) is calculated at step 1452 by setting the deductible payable amount (Dp) equal to the contract allowable amount 1402. The continuation of the 1450 logic path through step 1452 is linked to the second page 1500 of the estimation calculation of FIG. 15 via off page connector EC1 (1476).

If the calculated deductible owable amount (Do) 1418 is not greater than the contract allowable amount 1402, then path 1456 is selected and the deductible payable amount (Dp) is calculated at step 1454 by setting the deductible payable amount (Dp) equal to the calculated deductible owable amount (Do) 1418. At step 1458 the deductible payable amount (Dp) calculated in step 1454 plus the co-pay due amount (CPd) 1424, 1428 is compared to the contract allowable amount 1402. If the deductible payable amount (Dp) 1454 plus the co-pay due amount (CPd) 1424, 1428 is less than the contract allowable amount 1402, then path 1464 is chosen and the co-insurance due amount (CId) calculated in step 1466, described above, is applicable. The co-insurance due amount (CId) calculated in step 1466 is continued on page two 1500 of the estimation calculation disclosed in FIG. 15 via off page connector EC3 (1480).

If the deductible payable amount (Dp) 1454 plus the co-pay due amount (CPd) 1424, 1428 is not less than the contract allowable amount 1402, then path 1460 is chosen and the co-insurance due amount (CId) calculated in step 1466 is overridden by step 1462. At step 1462 the co-insurance due amount (CId) is set equal to zero. The co-insurance due amount (CId) of step 1462 is continued on page two 1500 of the estimation calculation disclosed in FIG. 15 via off page connector EC2 (1478).

Figure 15:
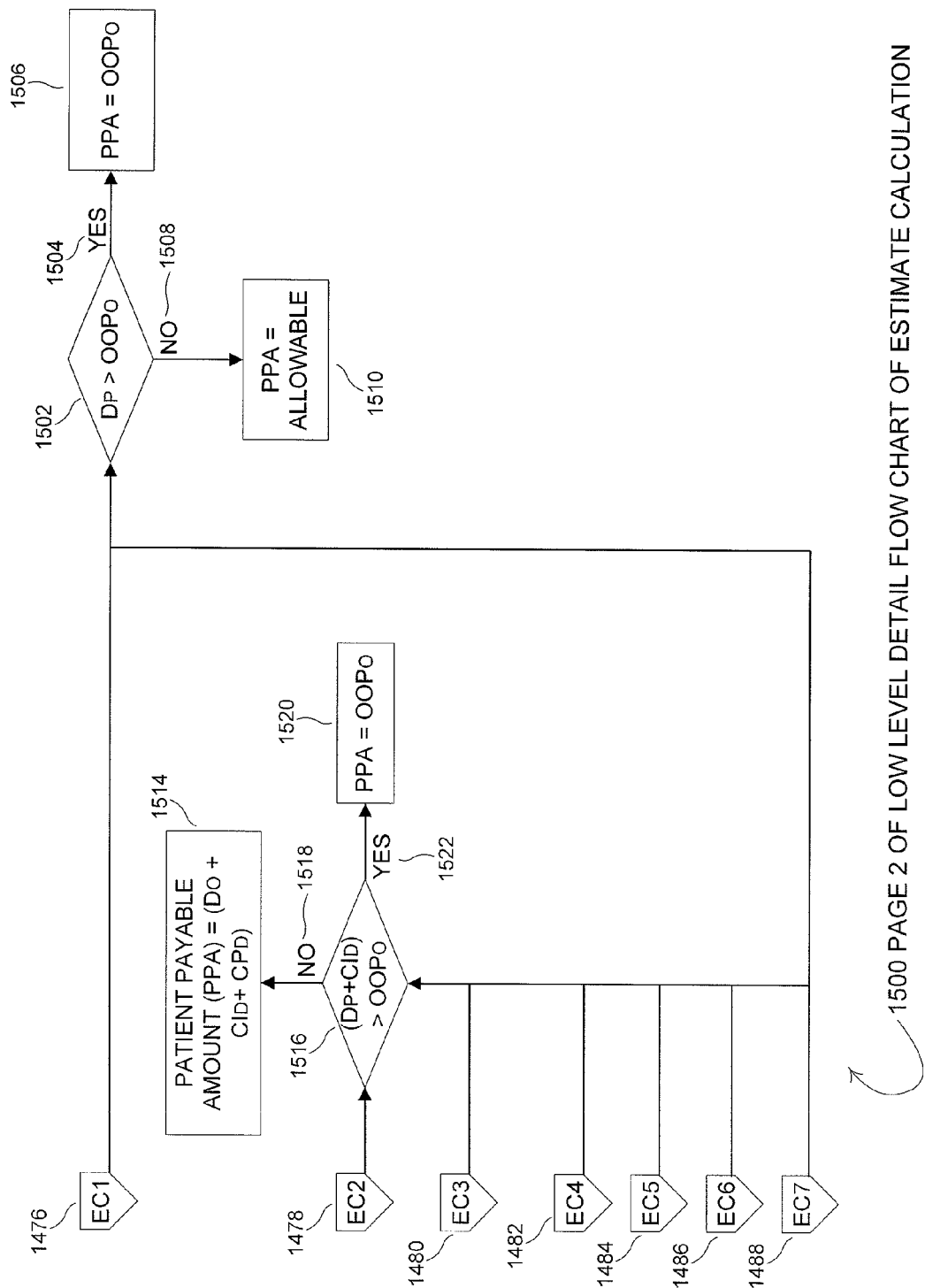
FIG. 15 is page two of the low level flow chart of the estimation calculation for the estimation path of an embodiment of the overall insurance estimation system.

FIG. 15 is page two (1500) of the low level flow chart of the estimation calculation for the estimation path 112 of an embodiment of the overall insurance estimation system 100. Step 1502 continues from the calculation of the deductible payable (Dp) amount of step 1452 via off page connector EC1 (1476). Step 1502 also utilizes the out of pocket owed amount calculated by one of steps 1468, 1470, 872, or 1474 via off page connectors EC4 (1482), EC5 (1484), EC6 (1486), or EC7 (1488), respectively. At step 1502, the deductible payable (Dp) of step 1452 is compared to the out of pocket owed (OOPo) calculated by one of steps 1468, 1470, 1472, or 1474. If the deductible payable (Dp) 1452 is greater than the out of pocket owed (OOPo) 1468, 1470, 1472, 1474 at step 1502, then path 1504 is selected and the patient payable amount (PPA) for the health care patient is calculated in step 1506. At step 1506, the patient payable amount (PPA) for the health care patient is set equal to the out of pocket owed amount (OOPo) 1468, 1470, 1472, 1474. If the deductible payable (Dp) 1452 is not greater than the out of pocket owed (OOPo) 1468, 1470, 1472, 1474 at step 1502, then path 1508 is selected and the patient payable amount (PPA) for the health care patient is calculated in step 1510. At step 1510, the patient payable amount (PPA) is set equal to the contract allowable amount 1402.

Step 1516 continues from the co-insurance due amount (CId) calculated in step 1462 or step 1466, depending on the result of step 1458, via off page connectors EC2 (1478) or EC3 (1480), respectively. Step 1516 also utilizes the out of pocket owed amount (OOPo) calculated in one of steps 1468, 1470, 1472, or 1474 delivered to step 1516 via off page connector EC4 (1482), EC5 (1484), EC6 (1486), or EC7 (1488), respectively. At step 1516, the addition of deductible payable (Dp) 1454 plus the co-insurance due amount (CId) 1462, 1466 is compared to the out pocket owed amount (OOPo) 1468, 1470, 1472, 1474. If the deductible payable amount (Dp) 1454 plus the co-insurance due amount (CId) 1462, 1466 is greater than the out of pocket owed amount (OOPo) 1468, 1470, 1472, 1474 at step 1516, then path 1522 is selected to go to step 1520. At step 1520, the patient payable amount (PPA) due from the patient is calculated by setting the patient payable amount (PPA) equal to the out of pocket owed amount (OOPo) 1468, 1470, 1472, 1474. If the deductible payable amount (Dp) 1454 plus the co-insurance due amount (CId) 1462, 1466 is not greater than the out of pocket owed amount (OOPo) 1468, 1470, 872, 1474 at step 1516, then path 1518 is selected to go to step 1514. At step 1514, the patient payable amount (PPA) due from the patient is calculated by setting the patient payable amount (PPA) equal to the deductible owable amount (Do) 1418 plus the co-insurance due amount (CId) 1462, 1466 plus the co-pay due amount (CPd) 1424, 1428.

The patient payable amount (PPA) 1506, 1510, 1514, 1520 for the health care patient may be used in an estimation letter to inform the patient, health care provider, facility, insurance company, or other interested party of the estimated amount owed by the health care patient. The estimate calculation described in FIGS. 14 and 15 represent the estimate calculations for one embodiment. Other embodiments may perform calculations in a different order or arrive at the patient payable amount using different calculations that may occur in different sequences, but obtain similar patient payable amounts for the health care patient. Additional calculations may also be desired. For instance, subtracting the patient payable amount (PPA) 1506, 1510, 1514, 1520 from the out of pocket owed amount (OOPo) 1468, 1470, 872, 1474 provides the amount of the out of pocket owed amount (OOPo) 1468, 1470, 1472, 1474 not paid by the health care patient and due from the insurance company. Further, subtracting the patient payable amount (PPA) 1506, 1510, 1514, 1520 from the contract allowable amount 1402 gives the entire amount due from the insurance company, including any of the out of pocket owed (OOPo) 1468, 1470, 1472, 1474 that was not included in the patient payable amount (PPA) 1506, 1510, 1514, 1520 of the patient.

Figure 16:
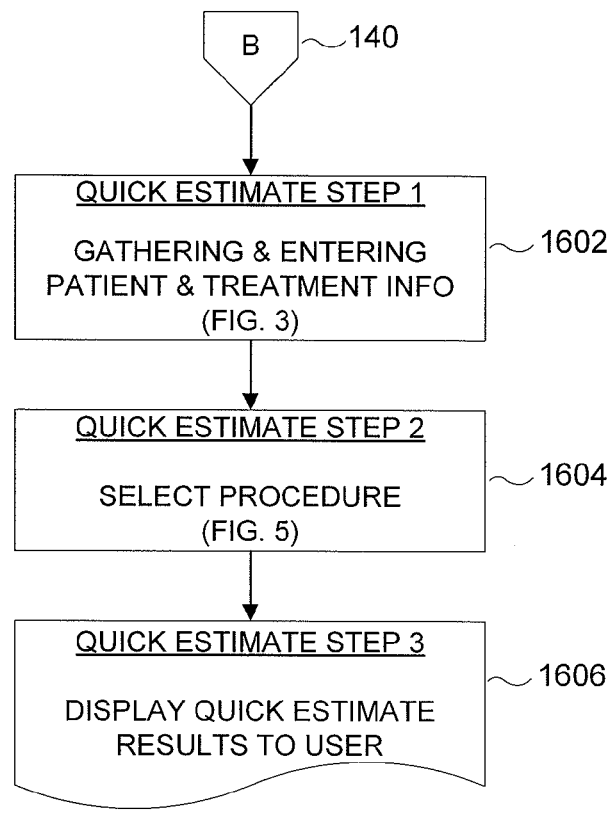
FIG. 16 is a middle level flow chart of the operation of the quick estimate path of an embodiment of the overall insurance estimation system.

FIG. 16 is a middle level flow chart 1600 of the operation of the quick estimate path 114 of an embodiment of the overall insurance estimation system 100. Access to the steps (1602, 1604, 1606) of the quick estimate path 114 may be restricted via role based security. After the user has selected the process for a quick estimate 114, the quick estimation process 114 moves to the first quick estimation step 1602 via off page connector B 140. At quick estimation step number one (1602), the user collects and enters information about the health care patient. At quick estimation step number two (1604), the user selects a healthcare procedure and enters treatment information for the health care patient. For the embodiment shown, quick estimation steps one (1602) and two (1604) use substantially similar processes as are used for full estimation steps one (202) and two (204), see FIGS. 3 and 5, respectively. The quick estimate path 114 skips steps three (206), four (208), and five (210) of the full estimation path 112. Instead of creating a full estimate letter, the quick estimate path 114 displays the results of the quick estimate calculations to the user on the screen at quick estimate step 3 (1606).

Figure 17:
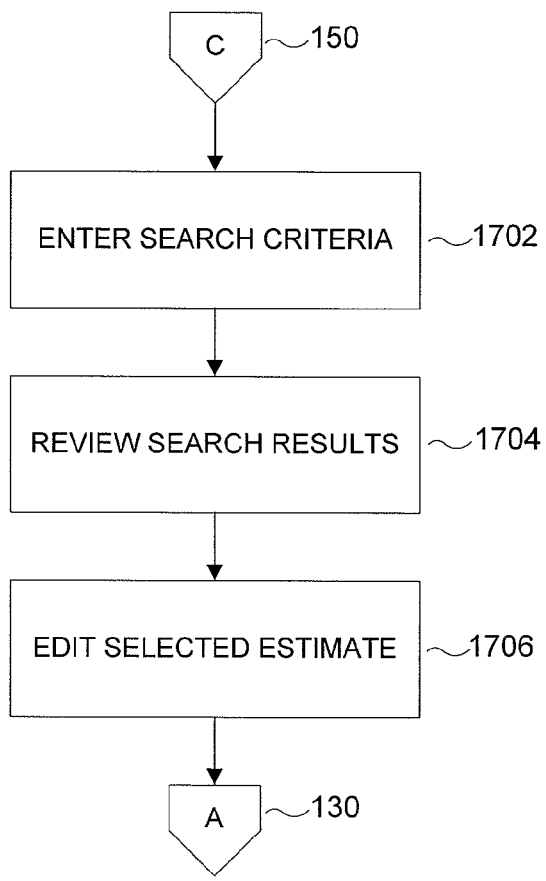
FIG. 17 is a low level flow chart for the estimation history path of an embodiment of the overall insurance estimation system.

FIG. 17 is a low level flow chart 1700 for the estimation history path 116 of an embodiment of the overall insurance estimation system 100. Access to the steps (1702, 1704, 1706) of the estimation history path 116 may be restricted via role based security. After the user has selected the process of accessing the estimation history 116, the estimation history process 116 moves to step 1702 via off page connector C 150. At step 1702, the user enters the search criteria. Some potential search criteria for searching the estimation history include, but are not limited to: facility, insurance company (contract), patient account number, patient name, patient last name, patient first name, estimate date, and/or a range of estimate dates. Access to specific search criteria may be individual restricted using role based security. For instance, a user may be restricted to a single pre-selected facility unless the user has permissions to change the selected facility value. Each of the search criteria may be searched individually or in combination with other search criteria. For instance, the account number may be searched across a range of dates, but the facility and insurance company may be left unselected. At step 1704, the user reviews the results of the search 1702. The results of the search 1702 may be shown in a list or other user readable form. The list may be summarized with short descriptive data in a table, including, but not limited to: facility name, patient name, contract/insurance company name, account number, and estimate date. To gain access to the details of a particular estimate, a "View" button may be associated with each individual result such that when a user clicks on the "View" button the user is taken to a detailed display of the selected historical estimate. At step 1706, the user may edit the selected historical estimate. If the user edits the historical estimate at step 1706, the user may move to the estimation path 112 via off page connector A 130, which links to FIG. 2 and/or FIG. 3, in order to handle the intricacies of editing the historical estimate.

Figure 18:
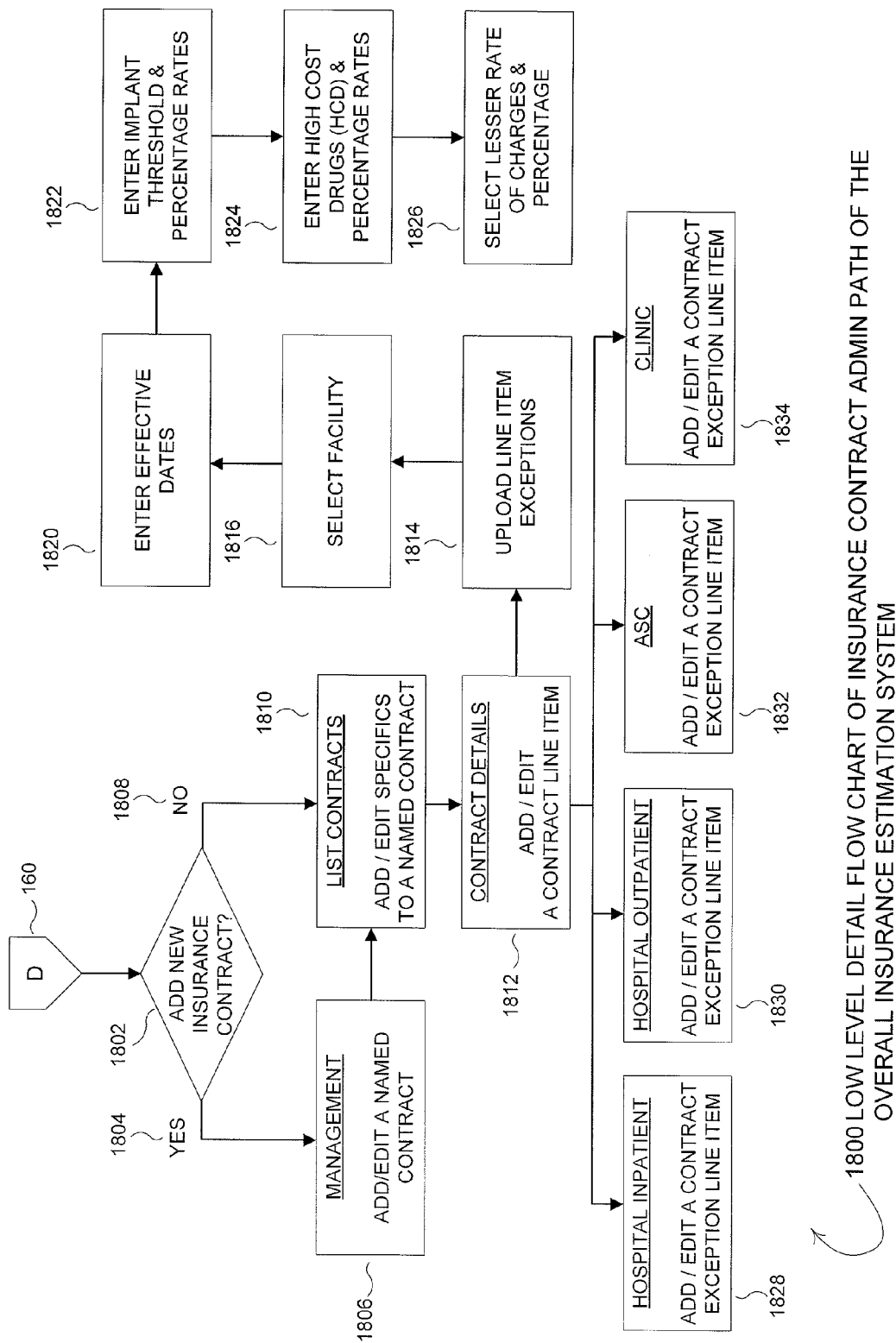
FIG. 18 is a low level flow chart for the insurance contract administration path of an embodiment of the overall insurance estimation system.

FIG. 18 is a low level flow chart 1800 for the insurance contract administration path 118 of an embodiment of the overall insurance estimation system 100. Access to the insurance contract administration portion 1800 of the insurance estimation system 100 may be restricted using a role based security model. For instance, only properly qualified user accounts may view, edit, or add insurance contracts. Further, viewing, editing, and adding insurance contract privileges may each be individually assignable such that one user may view the insurance contracts, but not be allowed to add or edit insurance contracts. After the user has selected the insurance contracts administration process 118, the insurance contracts administration process 118 moves to step 1802 via off page connector D 160. At step 1802, the user is asked whether the user desires to create a new insurance company contract. If the user desires to create a new insurance company contract 1804, then the user proceeds to management step 1806 and creates a new insurance company contract. From the management step 1806, the user proceeds to the list of contracts step 1810 where the user may select the newly created insurance company contract and edit the specific details of the newly created insurance company contract. If desired, the user may also select a different insurance company contract to edit from the list of insurance company contracts at step 1810. If the user chooses not to create a new insurance company contract 1808 at step 1802, the user proceeds to the list contracts step 1810 and selects a contract to edit. At step 1810, the user may add or edit specifics of the selected insurance company contract. At contract details step 1812, the user may add or edit specific line items of the selected insurance company contract. From the contract details step 1812, the user may proceed to contract line item steps individualized for a hospital inpatient 1828 (see FIG. 19), a hospital outpatient 1830 (see FIG. 20), an ASC 1832 (see FIG. 21), and a physician clinic 1834 (see FIG. 22). At steps 1828-32, the user may add or edit contract exceptions to a contract line item. From step 1812, the user may upload line item exceptions at step 1814. At step 1816, the user may select a facility for which to edit contracts. At step 1820, the user may enter the effective dates of the contract. At step 1822, the user may enter implant threshold and percentage rates. At step 1824, the user may enter High Cost Drugs (HCD) and percentage rates. At step 1826, the user may select a lesser rate of charges and/or percentage.

An insurance company contract is a reflection of the contract between a health care provider and/or facility and an insurance company. The insurance company contract may contain information regarding allowable amounts that may be charged for different health care products and/or services. Additional information for an insurance company contract may include the effective start and end dates of the contract. When the insurance estimation system 100 lists insurance companies for selection, the list may be a reflection of the list of contracts managed using the flow chart 1800. Further, the list of insurance company contracts may be limited to only insurance companies whose contracts are currently active such that a date of service that does not fall within the effective dates of an insurance company contract will cause the insurance company contract in question to not appear in a list of insurance companies for the health care product or service to be provided on the date of service in question. By limiting the available contracts to active contracts, it assists the data entry personnel to correctly select an insurance company contract. Limiting access to only active contracts to assist the data entry personnel reduces the sophistication and knowledge needed by the data entry personnel such that less knowledgeable and less expensive employees may be utilized to perform data entry tasks.

Contract administration 118 is where payer-provider contracts are modeled, thus, allowing the system to calculate the contractual allowable amount for patient estimates. Modeling the payer-provider contracts is a unique characteristic of the system that further differentiates the system from other estimation systems. Modeling the contracts creates a more credible and defendable estimate result. Historical claims information alone does not consider the complexities contained in the payer contracts, such as implant reimbursement carve-outs, high cost drug carve-outs, multiple procedure discounts, etc.

To model a payer-provider contract, the system captures all the complex logic contained in a contract by entering the reimbursement terms into the system. There are four common types of reimbursement calculation methodologies: hospital inpatient 1828, hospital outpatient 1830, Ambulatory Surgical Centers (ASC) 1832, and physician clinics 1834. The system allows for all four methodologies 1828-34 to be combined for a single payer contract to allow for combined professional and technical estimates (facility and physician).

Contracts have common terms that apply to multiple variations of contracts, including, but not limited to: name, aliases, effective dates, default implant and high cost drug (HCD) carve-outs, lesser rate of charges, stoploss, and facilities assignment. To begin modeling, all contracts are assigned a name and common aliasing (other naming conventions used by either the provider or patients). Effective dates are entered. If no termination date is defined, the end date is left blank thereby designating the contract as a perpetual or "evergreen contract."

Implants and HCD carve outs are important to define as they can drastically impact the credibility of the estimate. The implant and HCD carve outs are defined by first entering the threshold. The threshold is the charge amount that must be met before the carve-out percent of charge is applied. For example, if the threshold is $5,000 with a 50% percentage, the implant or HCD charges exceeding the threshold are the only amounts added to the allowable at the defined percentage. If the median charge for implants was $20,000, then ($20,000-$5,000)*50%, or $7,500, would be added to the allowable as a carve-out allowable.

Stoploss thresholds are values negotiated for extreme cases where the typical reimbursement would not adequately represent complicated cases when the patient has excessive charges. Stoploss thresholds are values that, once reached, the allowable calculation changes the reimbursement from one method to another. The charges up to the threshold are calculated using one methodology, and the charges over the threshold are calculated using a different methodology. In some cases, the entire calculation may be redone if the "first-dollar stoploss" is checked. Instead of the charge below the threshold being calculated using one methodology and the amount over the threshold calculated with another, the entire charge is calculated using the stoploss different methodology.

Another important characteristic of the contract is the assigned facilities. Some providers have centralized contracts that apply to any and all facilities. Others negotiate separate contracts unique to each facility. By assigning a contract to applicable facilities, the system is able to model any combination of contracts and facilities.

For hospital inpatient contracts, there are five predominant contract types that may be used alone or in conjunction with other contract types to model reimbursement terms: DRG/MSDRG, per diem, percent of charge (POC), case rates, and outlier.

DRG/MSDRG contracts use the Medicare payment methodology to define the reimbursable allowable. These contract types use the product of a weight and factor. Payers and providers negotiate a weight that is multiplied by factors designated by Medicare each year for each DRG/MSDRG. Instead of using Medicare factors, payers may use their own custom factors, which must be loaded into the contract to override the use of Medicare factors.

Per diem contracts use a rate that is negotiated for each revenue code type (medical, surgical, ICU, telemetry, obstetrics, spinal, cardiac, etc.). The per diem rate uses a flat rate per day. The allowable may be calculated by multiplying the appropriate per diem rate times the median length of stay for the procedure. The median length of stay is calculated by evaluating twelve to eighteen months of historical patient encounter data to determine the median. The median value is used as a better statistical representation of a typical charge over the average.

Percent of charge (POC) contracts use a percentage value that may be multiplied times the median charge. Like the length of stay, the median charge is calculated by evaluating twelve to eighteen months of historical patient encounter data. The total median charge is calculated and any median implant and/or median HCD charges are subtracted from the charge leaving only the facility charges.

Case rate contracts are the most simple contract type as each procedure is reimbursed by a predetermined value. Implant or HCD carve-outs may still apply, but the base allowable is a simple value.

Outlier contracts use a complex calculation evaluating minimum and maximum values as outliers and calculating the allowable differently depending on where the median charge falls relative to the thresholds. These contracts tend to be the most complex because 100% of the charge may be compared against the thresholds to obtain a percentage of the median charge to be compared. Once the thresholds have been determined, the allowable is calculated by applying the outlier percentage to the median charge.

For median charges falling under the initial threshold, the allowable may be calculated by finding the product of the initial percentage times the median charge. For median charges falling between the outlier thresholds, the allowable may be calculated by finding the product of a different percentage times the median charge. And for median charges exceeding the outlier thresholds, the allowable may be calculated by finding the product of yet a third percentage times the median charge.

For hospital outpatient, ASC, and clinical contracts, there are four primary calculation methodologies: percent of charges, case rates, percent of Medicare, or conversion factors.

Percent of charge (POC) contracts for outpatient contracts are like inpatient contracts and use a percentage value that is multiplied times the median charge. Like the length of stay, the median charge is calculated by evaluating twelve to eighteen months of historical patient encounter data. The total median charge may be calculated and any median implant and/or median HCD charges may be subtracted from the charge leaving only the facility charges.

Case rate contracts for outpatient contracts are like inpatient contracts. Case rate contracts are more simple than most contracts as each procedure is reimbursed by a predetermined value. Implant or HCD carve-outs may still apply, but the base allowable is a simple value.

Percent of Medicare (POM) contracts use the value of the procedure as defined by Medicare (for any given year) and multiply that value times a percentage.

Conversion factor contracts are similar to POM contracts in that they are both defined by values determined by Medicare. Instead of using the Medicare reimbursement values like in a POM, the conversion factor methodology uses a ratio between the Medicare conversion factor and a number negotiated between the payer and provider. The effective result is a different way of defining a percent of Medicare.

Figure 19:
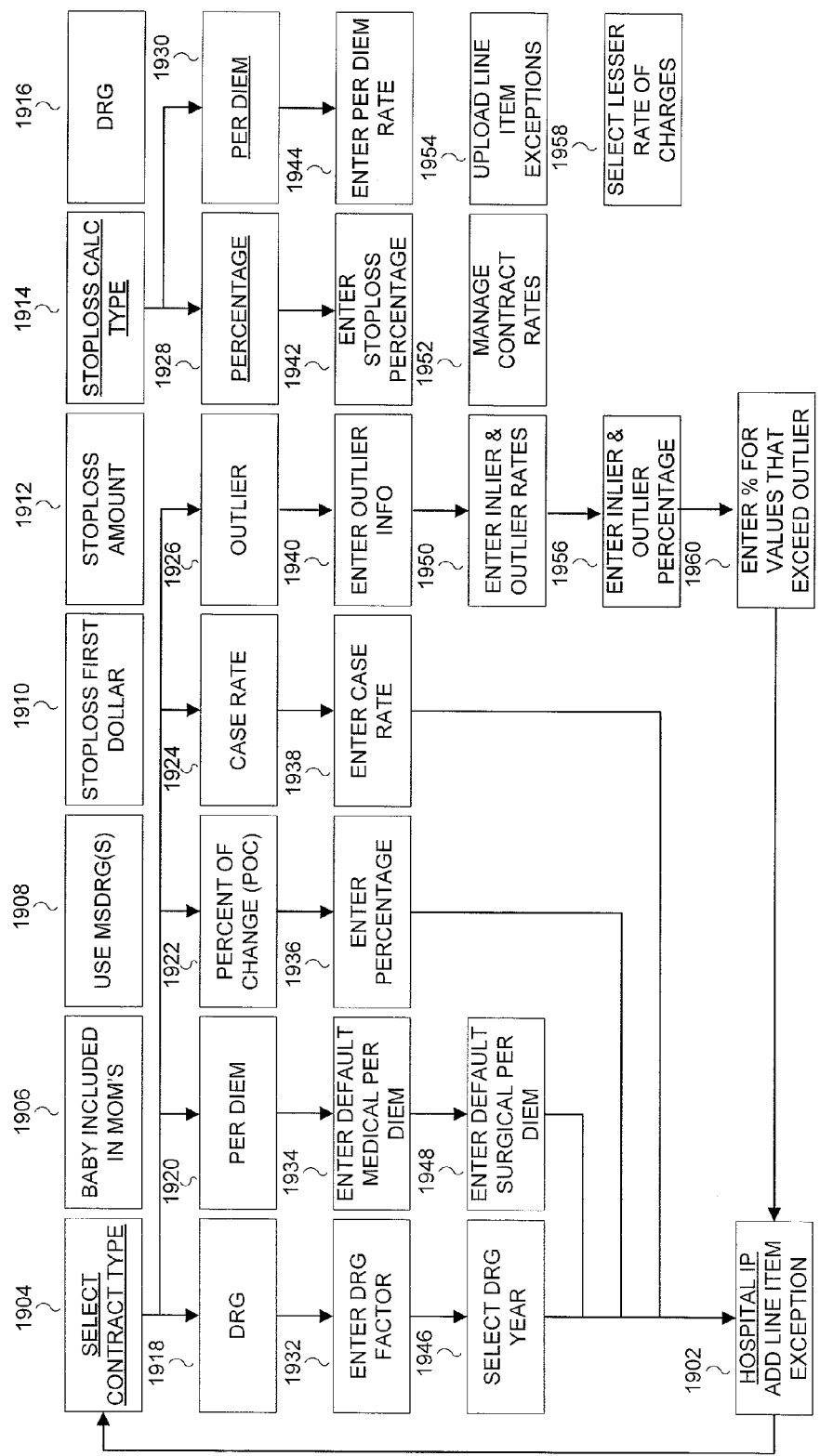
FIG. 19 is a low level flow chart of the operation of hospital inpatient logic for the insurance contract administration path of the embodiment shown in FIG. 18.

FIG. 19 is a low level flow chart 1900 of the operation of hospital inpatient logic 1828 for the insurance contract administration path 118 of the embodiment shown in FIG. 18.

At step 1902, the user is requested to add a line item exception. At step 1904, the user selects a contract type. From step 1904, the user may progress to the following types of contracts: DRG 1918, Per Diem 1920, Percent of Charge (POC) 1922, Case Rate 1924, or Outlier 1926. From the DRG contract 1918, the user may then enter the DRG factor at step 1932 and then select the DRG year at step 1946. From the Per Diem contract 1920, the user may then enter the default medical per diem at step 1934 and then enter the default surgical per diem at step 1948. From the Percent Of Charge (POC) contract 1922, the user may then enter a percentage at step 1936. From the Outlier contract 1922, the user may then enter miscellaneous outlier information at step 1940, then enter inlier and outlier rates at step 1950, then enter inlier and outlier percentages at step 1956, and enter the percentage for values exceeding the outlier at step 1960. From steps 1946, 1948, 1936, 1938, and 1960 (i.e., the five contract types) the user may return to step 1902 and enter additional line item exceptions. Other information that may be entered includes, but is not limited to: is the baby included on the mother's insurance 1906, use MSDRGs 1908, stoploss first dollar amount 1910, stoploss amount 1912, stoploss calculation type 1914, and use DRG 1916. For the stoploss calculation type 1914, the user may select a percentage type 1928 or a per diem type 1930. From the stoploss percentage type 1928, the user may enter the stoploss percentage at step 1942. From the stoploss per diem type 1930, the user may enter the per diem rate at step 1944. Other available functions include, but are not limited to: manage contract rates 1952, upload line item exceptions 1954, and select a lesser rate of charges 1958.

Figure 20:
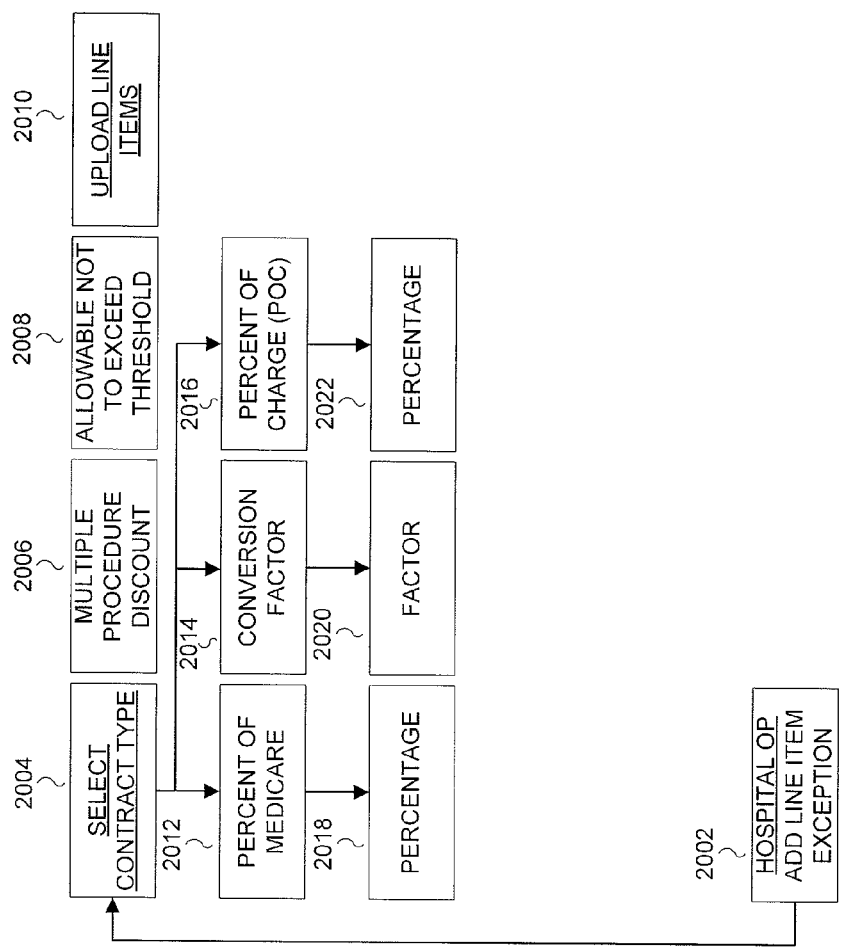
FIG. 20 is a low level flow chart of the operation of hospital outpatient logic for the insurance contract administration path of the embodiment shown in FIG. 18.

FIG. 20 is a low level flow chart 2000 of the operation of hospital outpatient logic 1830 for the insurance contract administration path 118 of the embodiment shown in FIG. 18. At step 2002, the user is requested to add a line item exception. At step 2004, the user selects a contract type. From step 2004, the user may progress to the following types of contracts: Percent of Medicare (POM) 2012, Conversion Factor 2014, or Percent of Charge (POC) 2016. From the Percent of Medicare contract 2012, the user may then enter a percentage at step 2018. From the Conversion Factor contract 2014, the user may then enter a factor at step 2020. From the Percent Of Charge (POC) contract 2016, the user may then enter a percentage at step 2022. Other information that may be entered includes, but is not limited to: is there a multiple procedure discount 2006 and is the allowable amount not to exceed the threshold amount 2008. Other available functions include, but are not limited to: uploading line item exceptions 2010.

Figure 21:
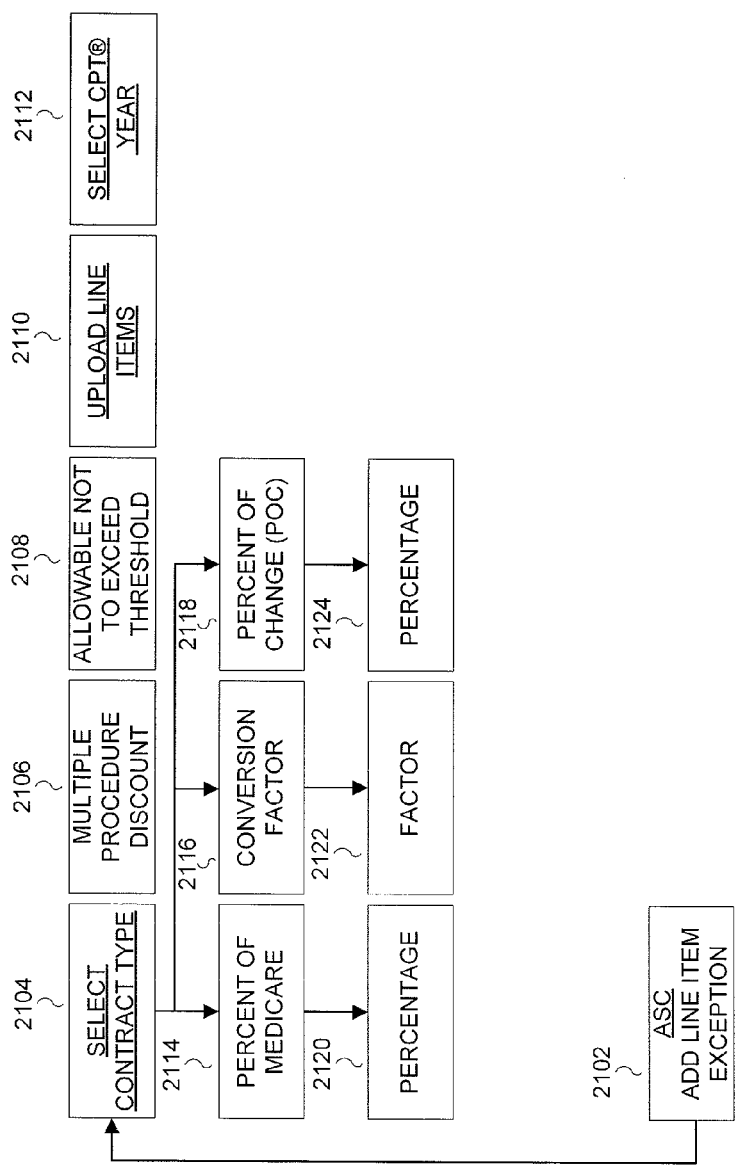
FIG. 21 is a low level flow chart of the operation of Ambulatory Surgical Center (ASC) logic for the insurance contract administration path of the embodiment shown in FIG. 18.

FIG. 21 is a low level flow chart 2100 of the operation of Ambulatory Surgical Center (ASC) logic 1832 for the insurance contract administration path 118 of the embodiment shown in FIG. 18. At step 2102, the user is requested to add a line item exception. At step 2104, the user selects a contract type. From step 2104, the user may progress to the following types of contracts: Percent of Medicare (POM) 2014, Conversion Factor 2116, or Percent of Charge (POC) 2118. From the Percent of Medicare contract 2114, the user may then enter a percentage at step 2120. From the Conversion Factor contract 2116, the user may then enter a factor at step 2122. From the Percent Of Charge (POC) contract 2118, the user may then enter a percentage at step 2124. Other information that may be entered includes, but is not limited to: is there a multiple procedure discount 2106 and is the allowable amount not to exceed the threshold amount 2108. Other available functions include, but are not limited to: uploading line item exceptions 2110 and selecting a CPT year 2112.

Figure 22:
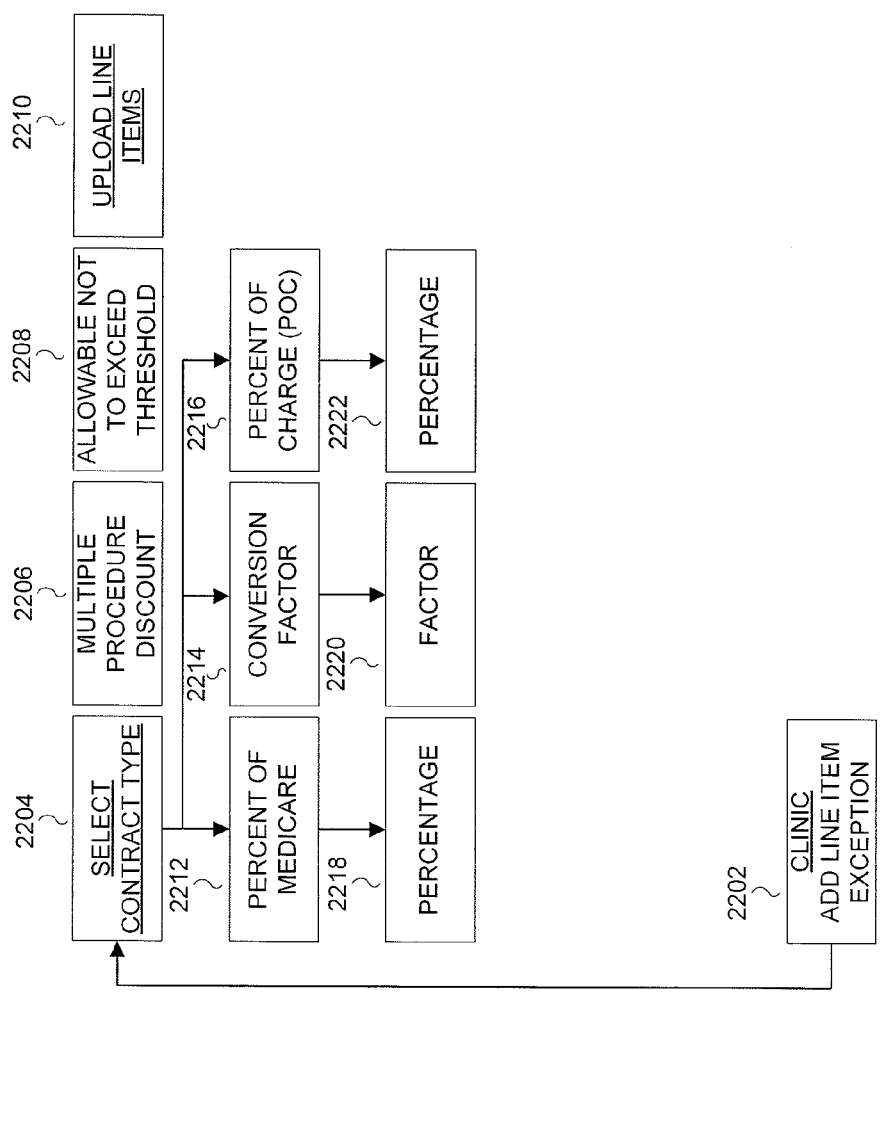
FIG. 22 is a low level flow chart of the operation of clinic logic for the insurance contract administration path of the embodiment shown in FIG. 18.

FIG. 22 is a low level flow chart 2200 of the operation of physician clinic logic 1834 for the insurance contract administration path 118 of the embodiment shown in FIG. 18. At step 2202, the user is requested to add a line item exception. At step 2204, the user selects a contract type. From step 2204, the user may progress to the following types of contracts: Percent of Medicare (POM) 2212, Conversion Factor 2214, or Percent of Charge (POC) 2216. From the Percent of Medicare contract 2212, the user may then enter a percentage at step 2218. From the Conversion Factor contract 2214, the user may then enter a factor at step 2220. From the Percent Of Charge (POC) contract 2216, the user may then enter a percentage at step 2222. Other information that may be entered includes, but is not limited to: is there a multiple procedure discount 2206 and is the allowable amount not to exceed the threshold amount 2208. Other available functions include, but are not limited to: uploading line item exceptions 2210.

The embodiments described with respect to FIGS. 19-22 reflect one embodiment of many different potential embodiments. A person skilled in the art may vary some of the specific content and/or order of steps of FIGS. 19-22 while still practicing the invention.

Figure 23:
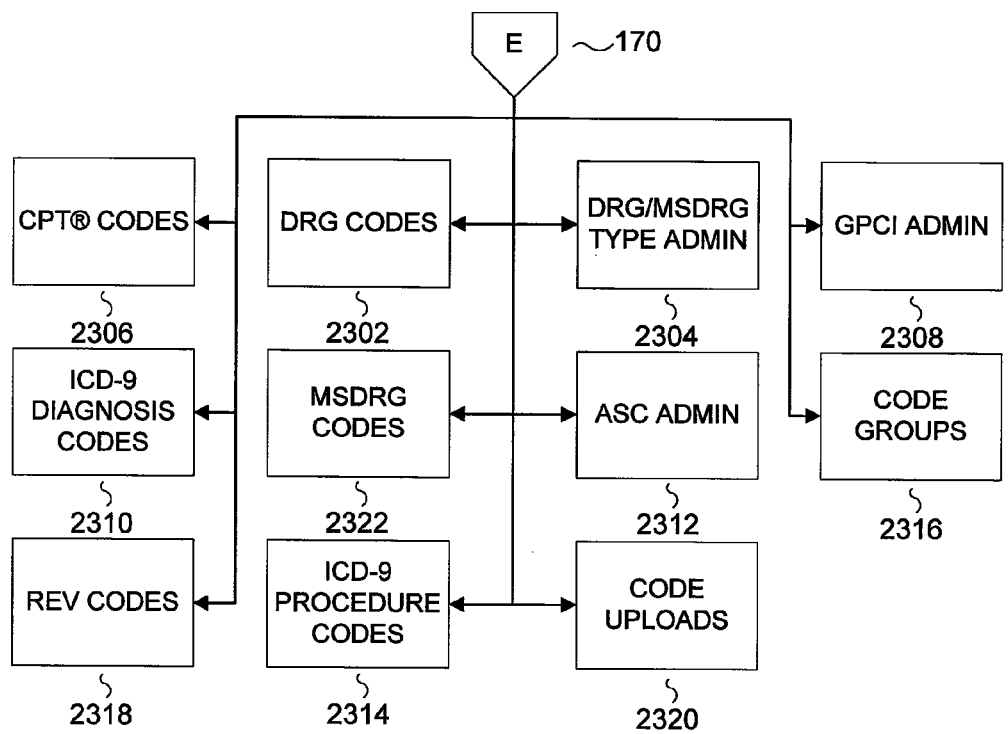
FIG. 23 is a low level flow chart for the health care code administration path of an embodiment of the overall insurance estimation system.

FIG. 23 is a low level flow chart 2300 for the health care code administration path 120 of an embodiment of the overall insurance estimation system 100. Access to the health care code administration portion 2300 of the insurance estimation system 100 may be restricted using a role based security model. After the user has selected the health care code administration process 120, the health care code administration process 120 accesses the health care code administration flow chart 2300 via off page connector E 170. At 2302, the user may manage the Diagnostic Related Groups (DRG) codes. At 2322, the user may mange the Medical Severity Diagnostic Related Groups (MSDRG) codes. At 2304, the user may perform DRG/MSDRG type administration functions. At 2306, the user may manage Current Procedural Terminology (CPT) codes. At 2308, the user may perform administration functions on Geographic Practice Cost Index (GPCI) information. At 2310, the user may manage International Classification of Diseases (ICD) codes within the diagnosis subclass. In the embodiment shown in FIG. 23, the ICD codes are from revision 9, referred to as ICD-9, but other revisions may be used instead of or in addition to revision 9 ICD codes. At 2312, the user may perform administration functions on Ambulatory Surgical Center (ASC) information, which may include specialized and/or proprietary health care code information. At 2314, the user may manage ICD-9 codes within the procedure sub-class. At 2316, the user may manage the different code groups and relationships between different health care codes. At 2318, the user may mange revenue codes. At 2320, the user may access code uploads for the computer system. Management of the health care codes 2300 permits the user to create and inter-relate a variety of health care codes and code systems. Health care code administration may also include assigning potential costs for procedures described by health care codes as well as performing historical analysis of the costs associated with specific health care codes.

Figure 24:
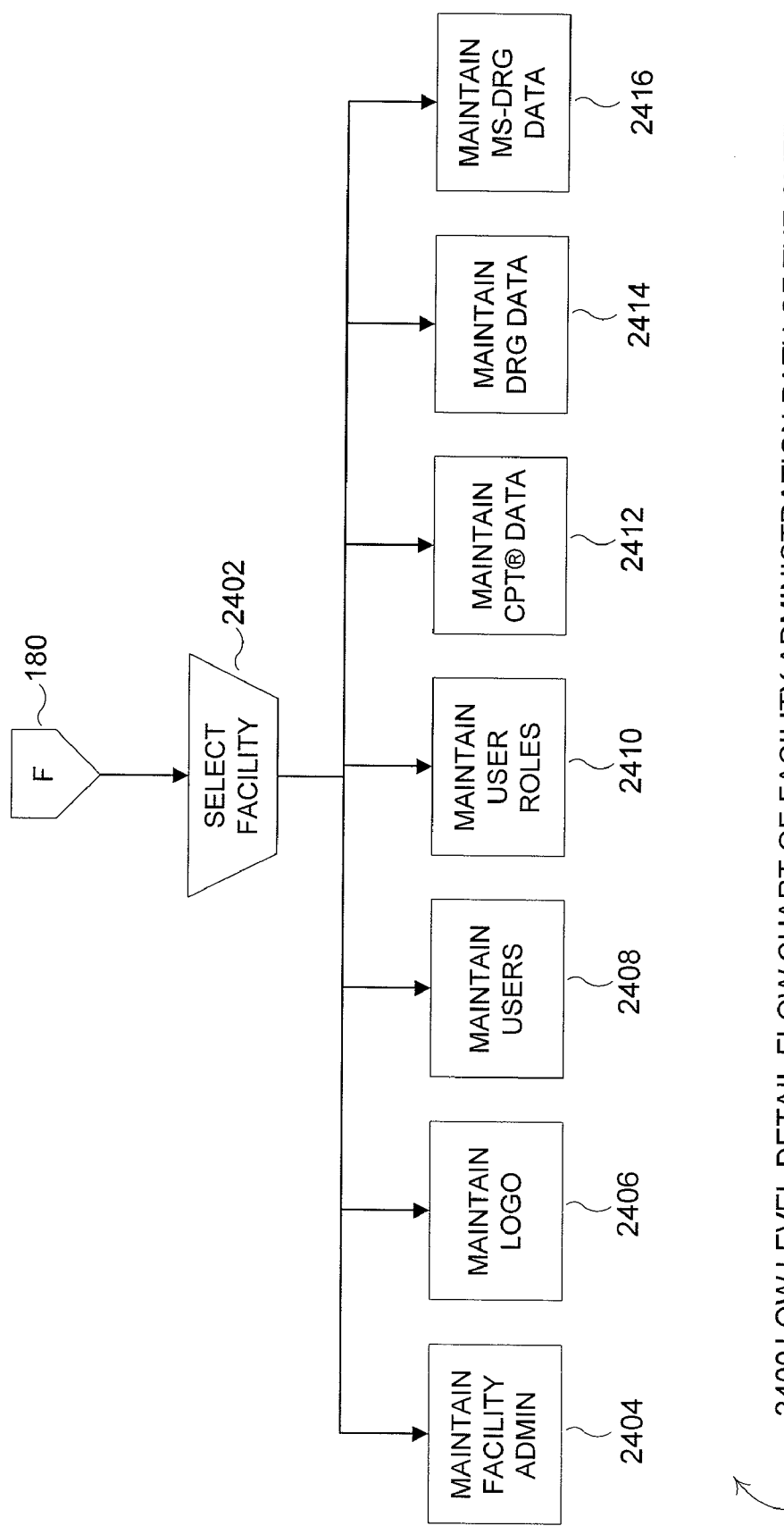
FIG. 24 is a low level flow chart for the facility administration path of an embodiment of the overall insurance estimation system.

FIG. 24 is a low level flow chart 2400 for the facility administration path 122 of an embodiment of the overall insurance estimation system 100. Access to the facility administration portion 2400 of the insurance estimation system 100 may be restricted using a role based security model. After the user has selected the facility code administration process 122, the facility administration process 122 accesses the facility administration flow chart 2400 via off page connector F 180. At step 2402 the user selects the facility on which the user desires to perform administrative tasks. At 2404, the user maintains facility administration, including creating new facilities and other administrative types of tasks. At 2406, the user maintains the logo associated with the selected facility. At 2408, the user maintains the list of users that have access to the insurance estimation system 100 for the selected facility. At 2410, the user maintains the specific role based security features for the list of users that have access to the insurance estimation system 100 for the selected facility. At 2412, the user maintains the Current Procedural Terminology (CPT) codes data for the selected facility. At 2414, the user maintains the Diagnostic Related Groups (DRG) data for the selected facility. At 2416, the user maintains the Medical Severity Diagnostic Related Groups (MS-DRG) data for the selected facility. Treatment costs and availability may be specifically tracked for specific facilities, thus, maintaining the CPT and DRG/MSDRG data for a selected facility may permit a user to keep track of historically, or otherwise estimated, costs for different health care codes available from the selected facility. Other embodiments may include maintenance of costs associated with other health care codes systems such as the ICD code system and/or a proprietary health care code system.

Figure 25:
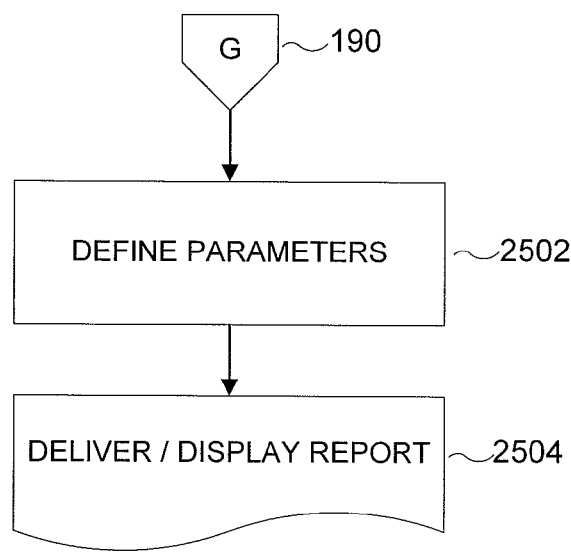
FIG. 25 is a low level flow chart for the reporting path of an embodiment of the overall insurance estimation system.

FIG. 25 is a low level flow chart 2500 for the reporting path 124 of an embodiment of the overall insurance estimation system 100. Access to the reporting portion 2500 of the insurance estimation system 100 may be restricted using a role based security model. After the user has selected the reporting process 124, the reporting process 124 accesses the reporting flow chart 2500 via off page connector G 190. At step 2502, the user defines the parameters of the desired report. At step 2504, the reporting process 124 delivers and/or displays the report as defined by the user in step 2502. Potential reports may include, but are not limited to: estimation worksheets, estimation letters, summary reports of a group of estimation worksheets, reports on health care codes, reports on system users, reports on system usage, and other various administration and data summary reports.

Figure 26:
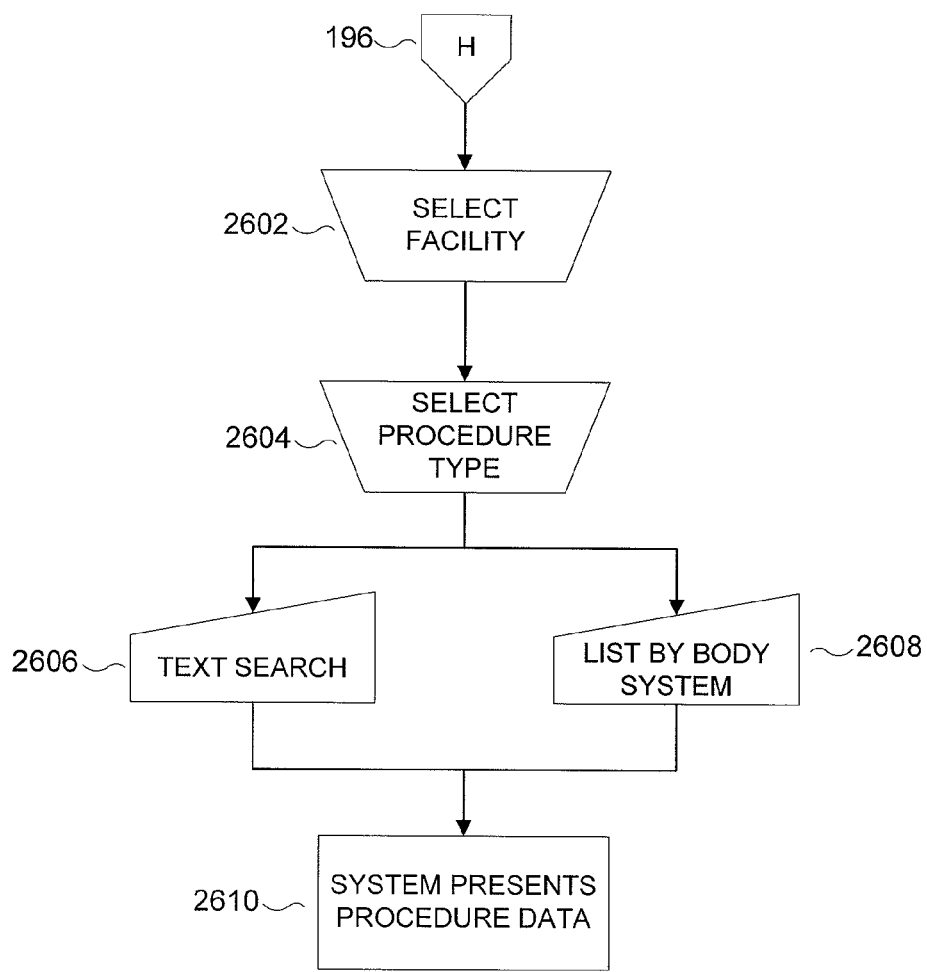
FIG. 26 is a low level flow chart for the transparency path of an embodiment of the overall insurance estimation system.

FIG. 26 is a low level flow chart 2600 for the transparency path 126 of an embodiment of the overall insurance estimation system 100. Access to the transparency portion 2600 of the insurance estimation system 100 may be restricted using a role based security model. After the user has selected the transparency process 126, the transparency process 126 accesses the transparency flow chart 2600 via off page connector H 196. At step 2602, the user selects a facility. At step 2604, the user selects a procedure type. From step 2604, the user may look for procedure data via a text search 2606 or via browsing a list of procedures by body part 2608. At 2610, the system presents the procedure data for display.

One skilled in the art may recognize that the various embodiments described with respect to FIGS. 1-26 may be modified while still providing substantially similar end results. The various embodiments shown in and described with respect to FIGS. 1-26 may be rearranged and reordered while still achieving a substantially similar system. The details disclosed with respect to FIG. 1-26 describe particular instantiations of various embodiments, but are not meant to describe all embodiments. As there may be a wide variety of small variations between various embodiments, attempting to describe each embodiment in detail would be unduly burdensome. Further, the embodiments described with respect to FIGS. 1-26 utilized revision 9 of the ICD codes, but other embodiments may utilize one or more revisions instead of or, in addition to, revision 9 of the ICD codes.

Figure 27:
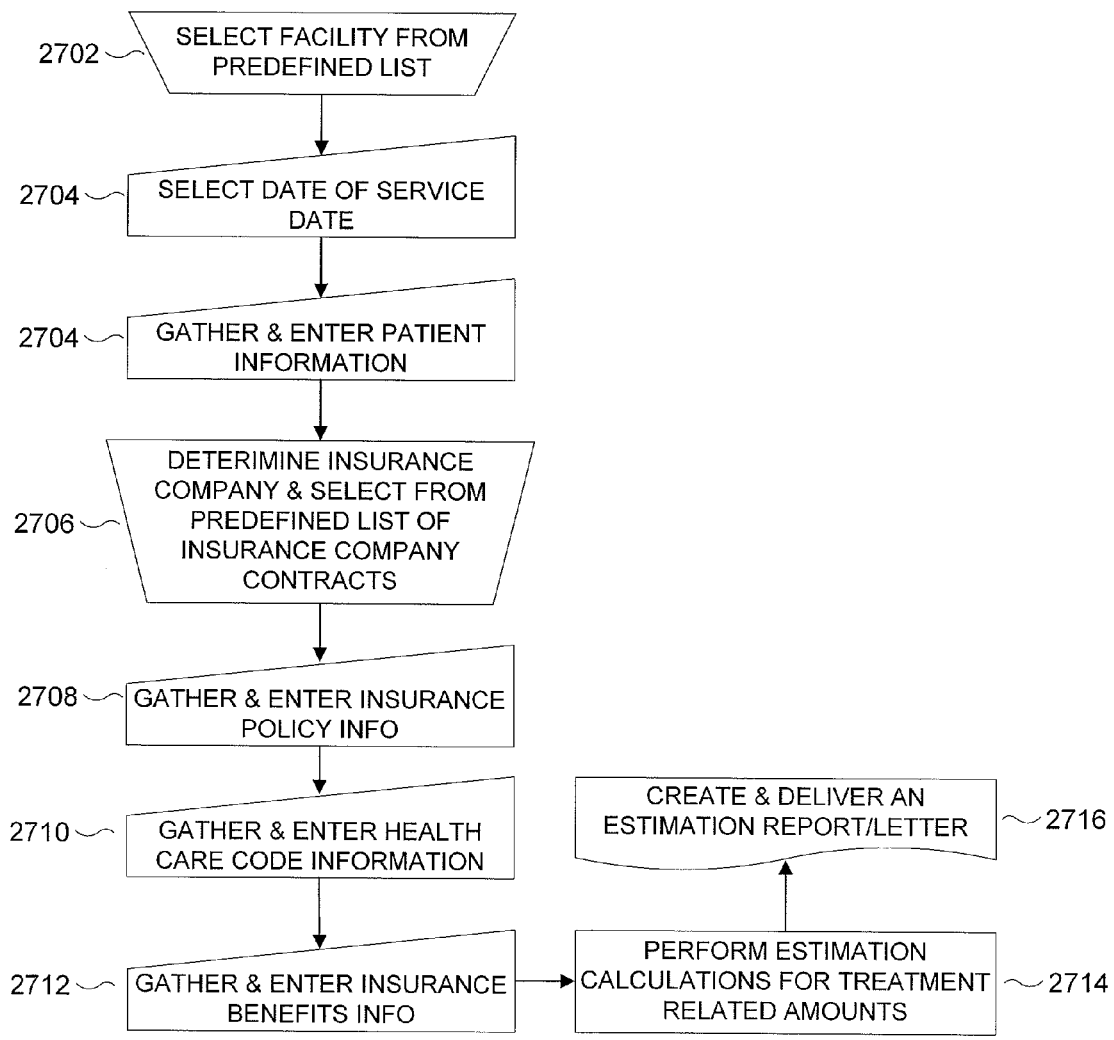
FIG. 27 is a low level flow chart of the general process for an embodiment estimating treatment related amounts for a health care product/service.

FIG. 27 is a low level flow chart 2700 of the general process for an embodiment estimating treatment related amounts for a health care product/service desired by a health care patient. The treatment related amounts may include, but are not limited to: estimated treatment costs, an estimated allowable amount, and an estimated patient payable amount. The processes shown in FIG. 27 may be implemented using a computerized system to carry out the various processes. At step 2702, a facility is selected from a predefined list of facilities. At step 2704, a date of service for when the health care product/service will begin to be provided to the health care patient is entered or selected. At step 2706, patient information is collected and entered into an embodiment of an insurance estimation system. Patient information may include, but is not limited to: date of birth, gender, name, and facility account number. At step 2708, the insurance company for the insurance coverage of the health care patient is determined and the appropriate insurance company is selected from the predefined list of insurance company contracts. The predefined list of insurance company contracts associates the insurance company name with the contractual data entered into the system for the contracts between the insurance company and the health care provider and/or facility. The list of available insurance company contracts may be filtered for the user by only listing active insurance company contracts. At step 2708, the policy information for the health insurance that covers the health care patient is gathered and entered into the insurance estimation system. Insurance policy information may include, but is not limited to: insurance policy number and insurance group number. At step 2712, information about health care codes that describe the health care product/service to be performed is gathered and entered into the insurance estimation system. Health care code information may include, but is not limited to: International Classification of Diseases (ICD) codes, Diagnostic Related Groups (DRG) codes, Medical Severity Diagnostic Related Groups (MS-DRG) codes, Current Procedural Terminology (CPT) codes, health care facility specific codes, doctor specific codes, and proprietary health care codes. At step 2714, insurance benefits information about the current coverage amounts (benefits) and the status of the health care patient's insurance coverage is gathered and entered into the insurance estimation system. The insurance benefits information may be obtained by calling the insurance company with the insurance policy information and/or automatically obtained by connecting to an electronic communication interface provided by the insurance company that permits a computer system to obtain insurance benefits information for a particular insurance policy. Insurance benefits information may include, but is not limited to: maximum deductible amount, deductible met amount, co-pay amount, is co-pay charged daily indicator, co-insurance percentage, maximum out of pocket amount, out of pocket met amount, is deductable included in out of pocket amount indicator, is co-pay included in out of pocket amount indicator, family maximum deductible amount, family deductible met amount, family maximum out of pocket amount, and family out of pocket met amount. At step 2716, calculations are performed to estimate the treatment related amounts. The estimate calculations may be based on the selected facility, selected date of service, the insurance company contract, the health care code information, and/or the insurance benefits information. The estimated treatment related amounts may include, but are not limited to: a patient payable amount owed by the health care patient, an amount owed by the selected insurance company, an allowable amount, and a total of all estimated charges. At step 2718, an estimation report/letter is created and delivered to an interested party. In addition to the estimated treatment related amounts, the estimation report/letter may include any of the information gathered about the patient, health care codes, insurance company, insurance policy, and/or insurance benefits information as supporting or supplemental data for the viewer to evaluate the estimated treatment related amounts.

One skilled in the art may recognize that the steps of the embodiment described by flow chart 2700 may be reordered while still obtaining a similar result as for the order of steps as flow chart 2700. For instance, the order for the data gathering and entry of steps 2702, 2704, 2706, 2708, 2710 and 2712 may be rearranged without affecting the estimate calculations. Further, entry of supplemental data, such as the patient's name, need not be completed prior to performing the estimate calculations at step 2714. In some instances steps may be performed substantially simultaneously. For instance, the step of performing the estimate calculation 2714 and creating the estimate report 2716 may be performed as a single process where estimated results are calculated and inserted into the report at the same time. One skilled in the art may further recognize that steps may also be similarly reordered for other embodiments described by other flowcharts.

Figure 28:
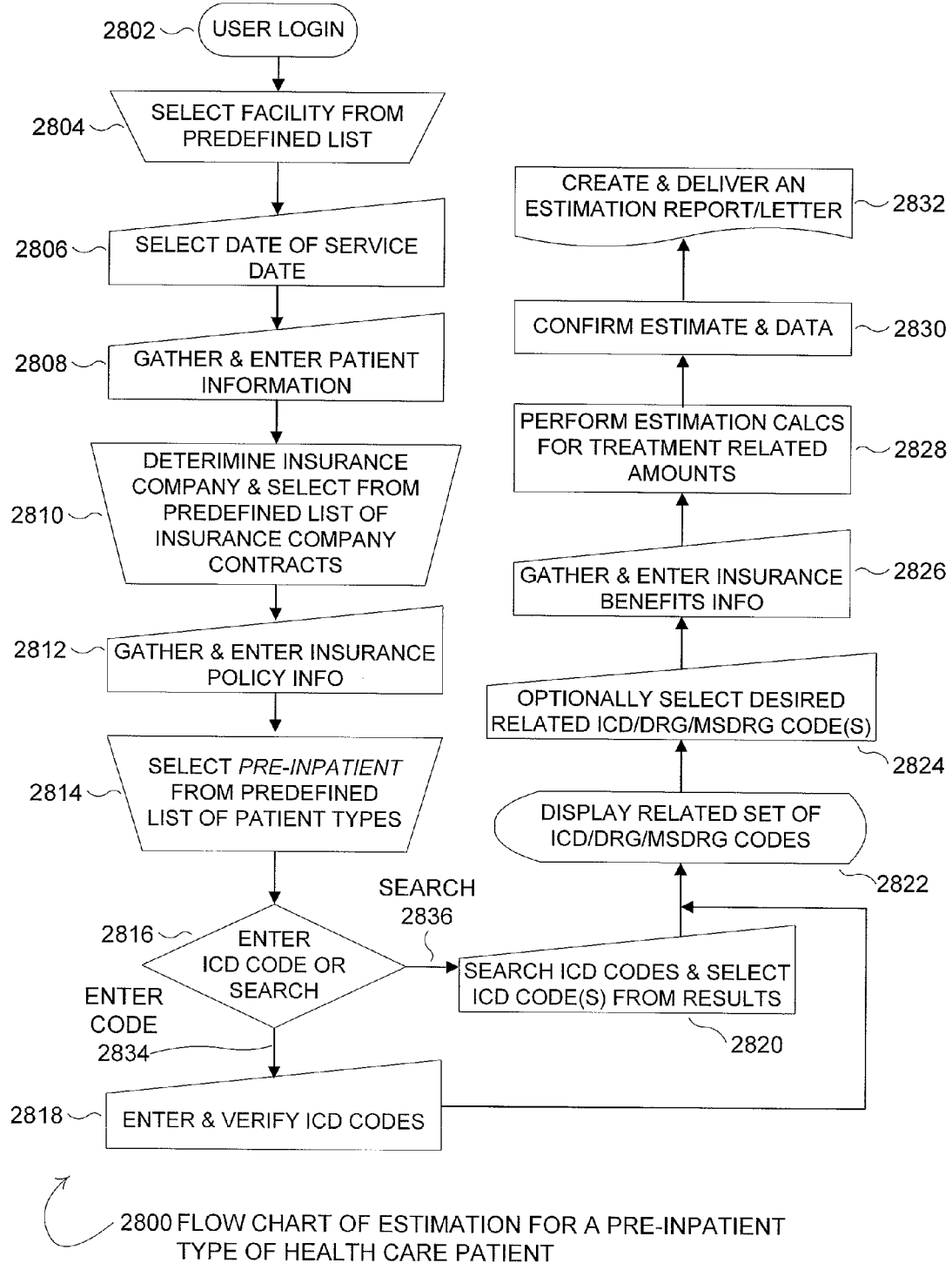
FIG. 28 is a flow chart of the estimation process for an embodiment estimating treatment related amounts for a health care product/service for a pre-inpatient type of health care patient.

FIG. 28 is a flow chart 2800 of the estimation process for an embodiment estimating treatment related amounts for a health care product/service for a pre-inpatient type of health care patient. The treatment related amounts may include, but are not limited to: estimated treatment costs, an estimated allowable amount, and an estimated patient payable amount. At step 2802, a user may log in to an embodiment of an insurance estimation system. Logging in may provide role based access to various parts of the insurance estimation system for different users. Logging in may be accomplished by entering a user name and password and selecting a login button. At step 2804, the user may select a facility from a predefined list of facilities if the user has the proper permissions to select a different facility. At step 2806, the user selects a date of service that indicates when the health care product or service is to start to be provided to the health care patient. The date of service may be selected in a variety of ways, including, but not limited to: entering the date directly or selecting the date using a displayed calendar. At step 2808, the user gathers and enters patient information such as the patient's first, middle, and last names as well as the patient's facility account number. Other patient information may include, but is not limited to: date of birth and gender. At step 2810, the user determines the insurance company name for the insurance that covers the health care patient and selects the insurance company from a list of insurance companies that is representative of insurance company contracts in place for the health care provider and/or facility. At step 2812, the user gathers insurance policy information, such as the insurance policy and group numbers, and enters the insurance policy information into the insurance estimation system. At step 2814, the user selects the pre-inpatient patient type from a pre-defined list of patient types. The pre-defined list of patient types may include, but is not limited to: pre-inpatient, pre-inpatient obstetric, in-house, and outpatient.

At step 2816, the user is prompted to either enter an ICD, or other, health care code, or to search for an ICD code. If the user opts to enter a code 2832 at step 2816, then at step 2818 the user may enter an ICD code. The ICD code may be verified as a valid ICD code by selecting a verify button for the entered ICD code and having the insurance estimation system verify the entered ICD code. If the user opts to search for an ICD code 2836, then at step 2820 the user performs a search within the available ICD codes. One embodiment may search by filtering the potential ICD codes into groups, such as grouping by the involved body system. Groups may also be created from other logical groupings, including displaying ICD codes based on sub-classes such as diagnostic and procedure sub-classes. One embodiment may perform searches based on other criteria such as a range of code numbers and/or text within the name/description of the health care code. Searches may also combine different search criteria to narrow searches even further. For instance, a search may include a text search of the name/description for codes in just the diagnostic sub-class. The results of the search may be presented as a list of potential health care codes that permits the user to select the desired health care code from the search list results. Both steps 2818 and 2820 are followed by step 2822.

At step 2822 a secondary list of ICD and DRG/MSDRG codes related to the previously selected ICD code are displayed to the user. The secondary list of ICD and DRG/MSDRG codes may be obtained by using the historical relationships between a primary ICD code and other related ICD and DRG/MSDRG codes that have been used to describe the same health care product or service in the past. The patient's age and/or gender may also be used to filter the related secondary ICD and DRG/MSDRG codes to those codes appropriate for the age and/or gender of the health care patient. The type/time of the estimate may also play a role in filtering the list of secondary ICD and/or DRG/MSDRG codes. For instance, if the estimate is done prior to providing the health care product or service, health care codes that include complications may be excluded. At step 2824, the user may optionally select ICD and/or DRG/MSDRG codes from the secondary list of health care codes. Selecting an ICD and or DRG/MSDRG from the secondary list of health care codes narrows the breadth of possible procedures included in the estimate calculation making the estimate more accurate. If a DRG/MSDRG code is not selected from the secondary list of health care codes, all of the potential DRG/MSDRG codes for the primary ICD code may be averaged together using a weighted average to obtain an estimated treatment cost for the health care product/service.

At step 2826, the user gathers insurance benefits information and enters the insurance benefits information into the insurance estimation system. The insurance benefits information describes the benefits available to the health care patient from the health care patient's insurance policy. Insurance benefits information may include, but is not limited to: a deductible amount (the patient's annual deductible), a deductible met amount (the patient's deductible met year-to-date), a maximum out of pocket amount (the patient's maximum annual out of pocket expense), an out of pocket met amount (the patient's out of pocket amount met year-to-date), a yes/no deductible included in out of pocket indicator (an indicator as to whether the patient's benefits include the deductible paid in the out of pocket amount), a yes/no co-pay included in out of pocket indicator (an indicator as to whether the patient's benefits include the co-pay amount in the out of pocket amount), a co-pay amount (the co-payment amount for the type of health care product/service being provided), and a co-insurance percentage (the patient portion of the co-insurance defining the percentage of costs after the deductible is met that is paid by the patient). Other embodiments may include different items such as defining the co-insurance as the amount due from the insurance company rather than the health care patient. An embodiment may also ask if there are individual and family benefits. If family benefits are available, the family deductible, family deductible met, family maximum out of pocket amount, and family out of pocket met may also be gathered and entered for the health care patient. If the insurance company was contacted, an insurance validation date, an insurance representative contacted name, and an insurance phone number may also be entered to complete additional data that may be presented to the health care patient in an estimate letter. The insurance benefits information may be obtained from the insurance company that covers the health care patient via online eligibility vendors, payer (insurance company) websites, calling payers, etc.

At step 2828 the estimate calculation is performed based on the selected facility, the selected date of service, patient information, selected insurance company contract, insurance policy information, health care code information, and insurance benefits information. At step 2830, a summary of the estimated treatment related amounts and a subset of the supporting facility, patient, health care code, and insurance information may be shown to the user to confirm the validity of the estimate and information. The subset of supporting information may include, but is not limited to all information gathered, selected, and/or entered for the health care patient. After confirming the estimate and supporting information, the user may save the estimate. An embodiment may permit a user to edit the supporting data and update the estimation calculation at the confirmation display without going through the estimate history process. At step 2832 the estimate letter/report is created and delivered to an interested party. The final estimate report/letter may be displayed on a computer screen, printed as hard copy, and/or sent as an e-mail. Other embodiments may include other delivery/display methods for the estimate report/letter.

Figure 29:
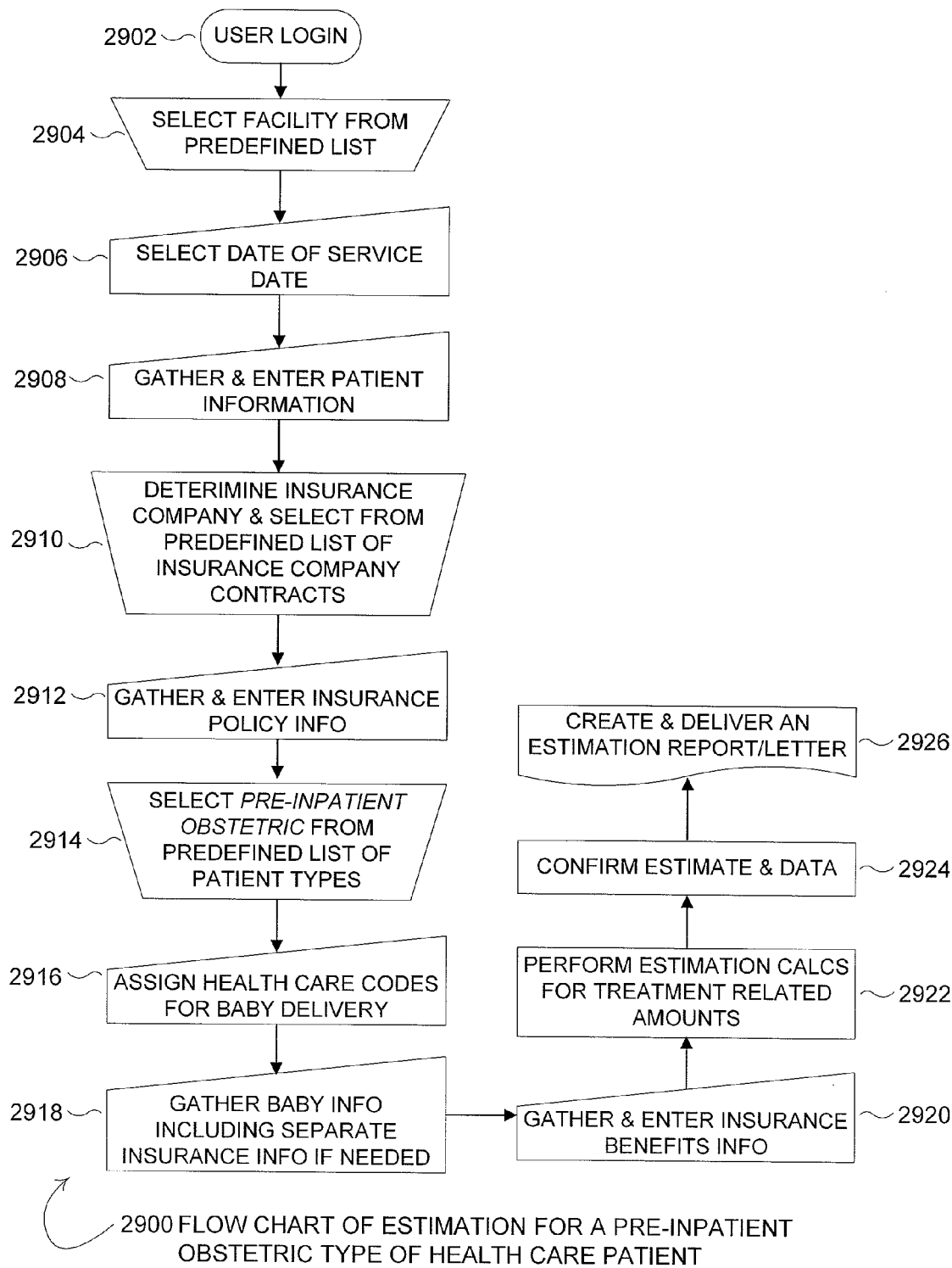
FIG. 29 is a flow chart of the estimation process for an embodiment estimating treatment related amounts for a health care product/service for a pre-inpatient obstetric type of health care patient.

FIG. 29 is a flow chart 2900 of the estimation process for an embodiment estimating treatment related amounts for a health care product/service for a pre-inpatient-obstetric type of health care patient. The treatment related amounts may include, but are not limited to: estimated treatment costs, an estimated allowable amount, and an estimated patient payable amount. At step 2902, a user may log in to an embodiment of an insurance estimation system. At step 2904, the user may select a facility from a predefined list of facilities if the user has the proper permissions to select a different facility. At step 2906, the user selects a date of service that indicates when the health care product or service is to start to be provided to the health care patient. At step 2908, the user gathers and enters patient information such as the patient's name, account number, date of birth and gender. At step 2910, the user determines the insurance company name for the insurance that covers the health care patient and selects the insurance company from a list of insurance companies. The list of insurance companies is representative of predefined insurance company contracts stored in the insurance estimation system for the health care provider and/or facility. At step 2912, the user gathers insurance policy information, such as the insurance policy and group numbers, and enters the insurance policy information into the insurance estimation system. At step 2914, the user selects the pre-inpatient-obstetric patient type from a predefined list of patient types. In one embodiment, to select a pre-inpatient-obstetric patient type may require more than one action. For instance, additional selections may be dependent on patient information such as gender. If the patient is female, the insurance estimation system may ask if the estimate is for a baby delivery. If the estimate is for a baby delivery, the insurance system may default the health care codes to health care codes applicable to child birth. Other questions may also be asked, such as vaginal or c-section birth, how many babies, and whether the baby is covered by one or two insurance policies. The baby may have separate insurance coverage from each of the mother and the father. If there are separate insurance policies, both the mother's and father's birthdates may need to be entered into the insurance estimation system.

At step 2916, the insurance estimation system assigns the health care codes to indicate that the health care product/ service is for baby delivery for the pre-inpatient-obstetric patient type. At step 2918, the user may gather additional information for the baby. The information for the baby may include separate insurance information for the baby, which may involve information for two separate policies covering the child. Additional baby information may also include separate patient information such as name, account number, or other information.

At step 2920, the user gathers insurance benefits information and enters the insurance benefits information into the insurance estimation system. The insurance benefits information describes the benefits available to the health care patient from the health care patient's insurance policy. For the case of child birth, the user may need to gather and enter separate insurance benefits information for the baby in addition to the information for the mother. In one embodiment, a separate section of the insurance estimation system may be dedicated to the data entry for the insurance benefits information for the mother with another section dedicated to the baby. Insurance benefits information may include, but is not limited to: a deductible amount, a deductible met amount, a maximum out of pocket amount, an out of pocket met amount, a yes/no deductible included in out of pocket indicator, a yes/no co-pay included in out of pocket indicator, a co-pay amount, and a co-insurance percentage. If family benefits are available, the family deductible, family deductible met, family maximum out of pocket amount, and family out of pocket met may also be gathered and entered for the health care patient and/or baby.

At step 2922 the estimate calculation is performed based on the selected facility, the selected date of service, patient information, selected insurance company contract(s), insurance policy information, health care code information, and insurance benefits information. At step 2924, a summary of the estimated treatment related amounts and a subset of the supporting facility, patient, health care code, and insurance information may be shown to the user to confirm the validity of the estimate and information. In one embodiment, the estimated costs and supporting information for the mother may appear on one half of the display while the estimated costs and supporting information for the baby may appear on the other half of the display. The subset of supporting information may include all information gathered, selected, and/or entered for the health care patient and/or the baby. After confirming the estimate and supporting information, the user may save the estimate. At step 2926 the estimate letter/report is created and delivered to an interested party. The final estimate report/letter may be displayed on a computer screen, printed as hard copy, and/or sent as an e-mail. Other embodiments may include other delivery/display methods for the estimate report/letter.

Figure 30:
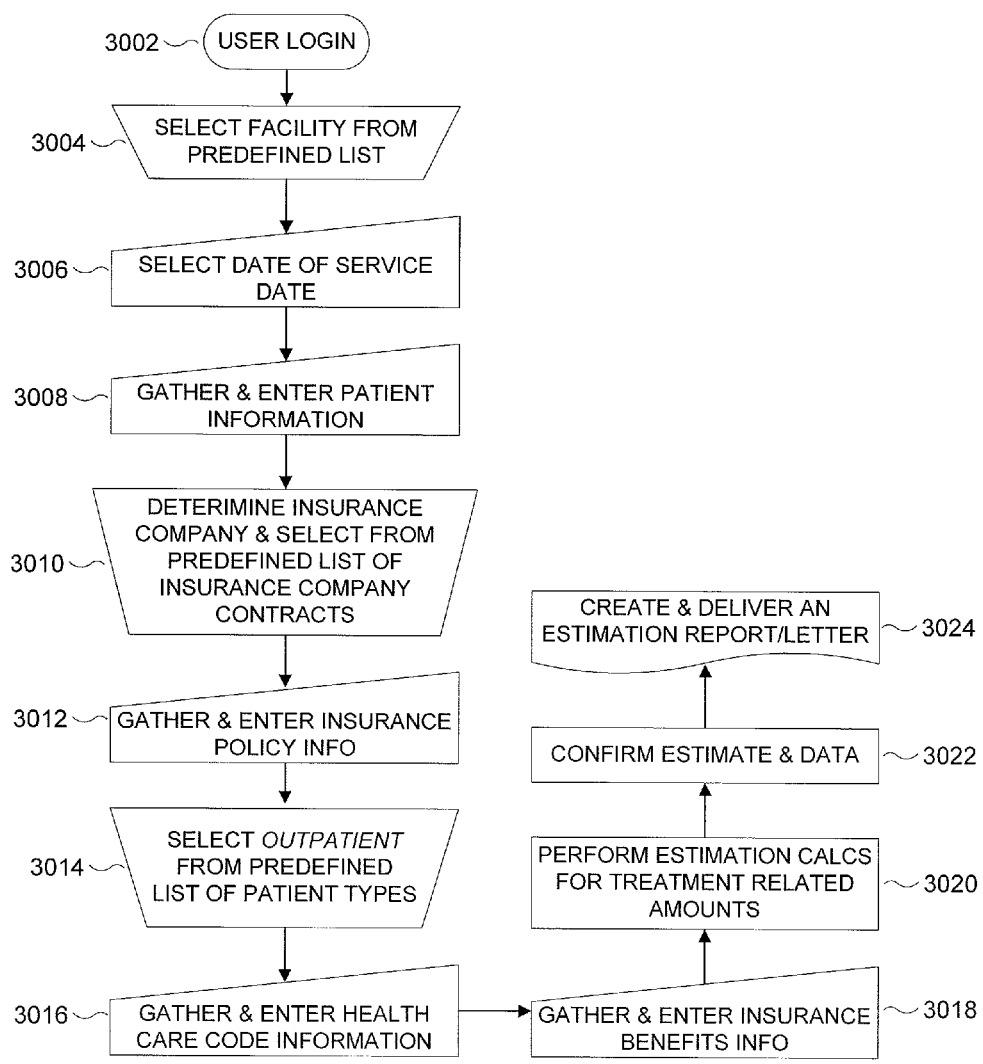
FIG. 30 is a flow chart of the estimation process for an embodiment estimating treatment related amounts for a health care product/service for an outpatient type of health care patient.

FIG. 30 is a flow chart 3000 of the estimation process for an embodiment estimating treatment related amounts for a health care product/service for an outpatient type of health care patient. The treatment related amounts may include, but are not limited to: estimated treatment costs, an estimated allowable amount, and an estimated patient payable amount. At step 3002, a user may log in to an embodiment of an insurance estimation system. At step 3004, the user may select a facility from a predefined list of facilities if the user has the proper permissions to select a different facility. At step 3006, the user selects a date of service that indicates when the health care product or service is to start to be provided to the health care patient. At step 3008, the user gathers and enters patient information such as the patient's first, middle, and last names as well as the patient's facility account number. Other patient information may include, but is not limited to: date of birth and gender. At step 3010, the user determines the insurance company name for the insurance that covers the health care patient and selects the insurance company from a pre-defined list of insurance companies that is representative of insurance company contracts in place with the health care provider and/or facility. At step 3012, the user gathers insurance policy information, such as the insurance policy and group numbers, and enters the insurance policy information into the insurance estimation system. At step 3014, the user selects the outpatient patient type from a pre-defined list of patient types.

At step 3016, the user may enter one or more health care codes. In some cases, Current Procedural Terminology (CPT) codes may be applicable to an outpatient patient type as the health care product/service may have already been provided to the health care patient at the time the estimate is performed. In one embodiment, each health care code may be verified by the insurance estimation system by selecting a verify button for the health care code. When the health care code is verified, the insurance estimation system may also fill in the name/description field for the health care code.

At step 3018, the user gathers insurance benefits information and enters the insurance benefits information into the insurance estimation system. The insurance benefits information describes the benefits available to the health care patient from the health care patient's insurance policy. At step 3020 the estimate calculation is performed based on the selected facility, the selected date of service, patient information, selected insurance company contract, insurance policy information, health care code information, and insurance benefits information. At step 3022, a summary of the estimated treatment related amounts and a subset of the supporting facility, patient, health care code, and insurance information may be shown to the user to confirm the validity of the estimate and information. The subset of supporting information may include all information gathered, selected, and/or entered for the health care patient. After confirming the estimate and supporting information, the user may save the estimate. An embodiment may permit a user to edit the supporting data and update the estimation calculation at the confirmation display. At step 3024 the estimate letter/report is created and delivered to an interested party. The final estimate report/letter may be displayed on a computer screen, printed as hard copy, and/or sent as an e-mail. Other embodiments may include other delivery/display methods for the estimate report/letter.

FIG. 31 is an example estimation worksheet 3100 for an embodiment of a pre-inpatient type of health care patient. The estimate worksheet 3100 may show both the final estimated treatment related amounts 3110 as well as other information that supports or supplements the estimated treatment related amounts 3110. For instance, in the embodiment shown, the patient name and service date 3102 may be included. Health care code information 3104 may also be included. Further, the patient's account number and the patient's insurance company name as well as insurance policy and group numbers 3108 may be included. The details of the patient's insurance benefits, including the out of pocket max, out of pocket met, deductible, deductible met, co-pay, and co-insurance percentage 3106 may also be included. The estimated treatment related amounts 3110 may include, but are not limited to: estimated treatment costs, an estimated allowable amount, and an estimated patient payable amount.

Embodiments of the insurance estimation system permit the health care provider and/or facility to supply the health care patient a copy of the estimate letter/report containing an estimated patient payable amount prior to receiving the final calculations from the insurance company. Since it often takes the insurance company 30-90 days to supply the final calculations to the health care provider and/or facility, an embodiment of the insurance estimation system might permit the health care provider and/or facility to start the process of collecting payment either prior to providing the health care product/service to the patient or immediately following the time the health care product/service is provided to the patient. Thus, the health care provider and/or facility may quicken the pace of the payments and overall cash flow. Further, if the patient does not receive a bill until 30-90 days after the patient has been treated, the patient has many times made the assumption that all of the bills are paid and is surprised by the new bill. When the bill comes significantly after the patient was treated, the patient may be more likely to protest valid bills, thus, delaying payment even longer while the patient goes through the process of protesting the bill. In some instances, the late bills may make the patient more likely to default on the bill as well. By supplying an estimate and creating an expectation of what the charges to the patient are expected to be early in the process, the patient may be less likely to protest valid bills, thus, reducing the time to final payment as well as reducing the expense in handling protested bills. Further, the health care provider and/or facility may include contractual terms for payment prior to or at the time service is provided such that the health care provider and/or facility has a stronger contractual standing for collection of bad debts than if the patient was billed significantly after the patient received treatment.

FIG. 32 is an example estimation worksheet 3200 for an embodiment of a pre-inpatient obstetric type of health care patient. The estimate worksheet 3200 may show both the final estimated treatment related amounts 3210, 3218, 3220 as well as other information that supports or supplements the estimated treatment related amounts 3210, 3218, 3220. Final estimated treatment related amounts may be separated into a section for the mother 3210, the baby 3218, and a total of the mother's and baby's treatment related amounts 3220. Supporting and supplemental information may include information for the mother 3202, 3204, 3206, 3208 and information for the baby 3212, 3214, 3216. In the embodiment shown, the mother's supplemental and supporting information may include patient name and service date 3202. Health care code information for the mother 3204 may also be included. Further, the mother's patient account number and the mother's insurance company name as well as insurance policy and group numbers 3208 may also be included. The details of the mother's insurance benefits, including the out of pocket max, out of pocket met, deductible, deductible met, co-pay, and co-insurance percentage 3206 may be shown to help clarify the final estimated treatment related amounts. Similar supplemental and supporting information may also be shown for the baby. For the embodiment shown, the baby's diagnosis 3212, insurance company name 3216, and insurance benefits information 3214 is shown. The estimated treatment related amounts 3210, 3218, 3220 may include, but are not limited to: estimated treatment costs, an estimated allowable amount, and an estimated patient payable amount.

FIG. 33 is an example estimation worksheet 3300 for an embodiment of an outpatient type of health care patient. The estimate worksheet 3300 may show both the final estimated treatment related amounts 3310 as well as other information that supports or supplements the estimated treatment related amounts 3310. For instance, in the embodiment shown, the patient name and service date 3302 may be included. Health care code information 3304, such as CPT codes, may also be included. Further, the patient's account number and the patient's insurance company name as well as insurance policy and group numbers 3308 may be included. The details of the patient's insurance benefits, including out of pocket max, out of pocket met, deductible, deductible met, co-pay, and co-insurance percentage 3306 may also be included. The treatment related amounts 3310 may include, but are not limited to: estimated treatment costs, an estimated allowable amount, and an estimated patient payable amount.

FIG. 34 is an example financial responsibility section 3400 for an embodiment of an estimation worksheet/letter. The estimation worksheet/letter may include a portion to establish the financial responsibility of the patient portion of the payment costs. In the embodiment shown, the patient is asked to pay for the health care product/service and is given several payment options such as check, money order, or credit card. The patient is also asked to sign the form to create a contractual relationship for payment of the estimated patient's payable portion of the treatment costs/allowable amount.

Figure 35:
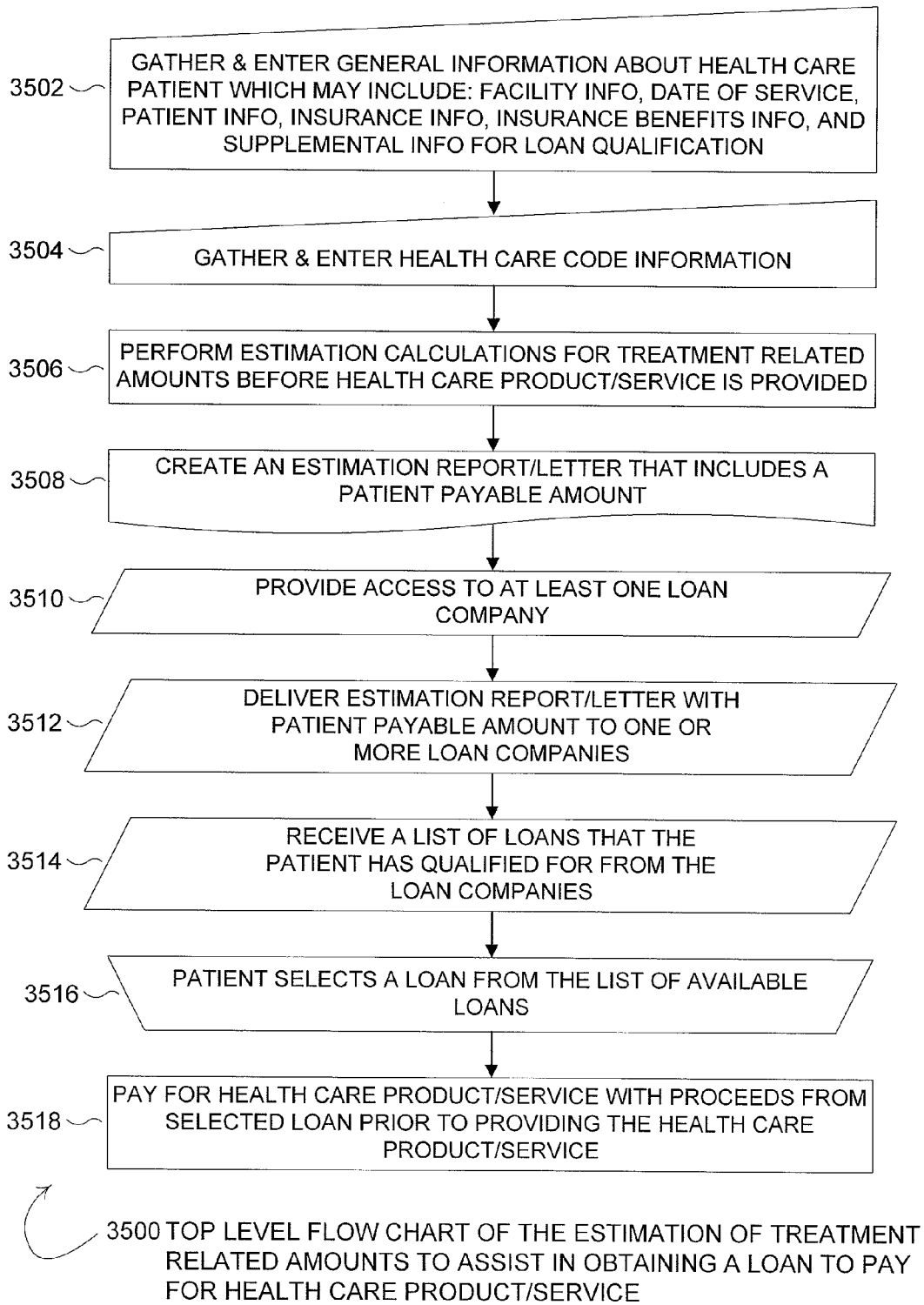
FIG. 35 is a top level flow chart of the estimation of treatment related amounts in order to assist a health care patient in obtaining a loan to pay the estimated patient payable amount for the health care product/service.

FIG. 35 is a top level flow chart 3500 of the estimation of treatment related amounts in order to assist a health care patient in obtaining a loan to pay the estimated patient payable amount for the health care product/service. The estimated treatment related amounts may include, but are not limited to: estimated treatment costs, an estimated allowable amount, and an estimated patient payable amount. At step 3502, general information about the health care patient and the insurance coverage of the patient is gathered and entered into the insurance estimation system. General information may include, but is not limited to: facility information, date of service for the start of the health care product/service, patient information, insurance information, insurance benefits information, and supplemental information for loan qualification. The facility information, date of service, patient information, insurance (including company and policy information, and insurance benefits information may be described in further detail as similar information has been described in descriptions for other figures in this application. The supplemental information for loan qualification may include information that is only needed to qualify for a loan such as information related to the health care patient's financial background. At step 3504, information about the health care code information is gathered and entered into the insurance estimation system. The health care code information is information that defines the health care codes that describe the health care product/service that is to be provided to the health care patient is gathered and entered into the insurance estimation system. At step 3506, the estimation calculations to obtain treatment related amounts for the health care product/service are performed by the insurance estimation system based on the health care code information entered in step 3504 and the general information entered in step 3502. The estimation calculations are performed prior to providing the health care product/service in order to permit the health care provider to obtain payment of the estimated patient payable amount before any time or expense is incurred to supply the health care product/service. Other embodiments may perform these calculations at a time prior to the insurance company delivering the final cost amounts and still permit the health care provider to bill and/or inform the health care patient of the estimated costs at an earlier time than would be available if the health care provider were to wait for the final calculations from the insurance company. At step 3508, the insurance estimation system creates an estimation report that includes an estimated patient payable amount that estimates the portion of the total cost for the health care product/service that will be the health care patient's financial responsibility. At step 3510, access is provided to at least one loan company. Access to the loan companies may be provided via electronic means using electronic communications between the health care provider's computers and the loan companies' computers. Access to the loan companies may be provided in a format referred to as a loan tree such that multiple loan companies are contacted and a tree or list of loans is returned to the loan applicant so the loan applicant may select a desired loan from the tree or list. At step 3512, the insurance estimation system delivers the estimation report/letter to the loan companies. The loan companies may set the principal of the loan to be equal to or in excess of the estimated patient payable amount. If the patient is going to pay a portion of the patient payable amount up front, the loan principal may also be lower than the patient payable amount. The patient payable amount may also be lower if the loan company is willing to loan some, but not all of the patient payable amount. When the full amount of the estimated patient payable amount is not available in a loan, the health care provider may seek the remainder of the patient payable amount from the health care patient directly or the patient may pursue a second loan. Information in the estimate report/letter may also include the supplemental information for loan qualification entered in step 3502. At step 3514, the insurance estimation system receives the list or tree of available loans that the health care patient has qualified for. At step 3516, the health care patient selects the desired loan from the list of available loans. At step 3518, the health care provider collects payment for the estimated patient payable amount for the health care product/service from the proceeds of the selected loan prior to supplying the health care product/service to the patient. Other embodiments may collect payment for the estimated patient payable amount at any time prior to when the insurance company provides the final calculations and still obtain payment earlier than waiting for the insurance company to provide the final calculations.

Interaction with the loan companies may be automated. For instance, all communications for delivering the estimation report/letter and receiving the list of available loans may be performed using electronic communications between the insurance company and health care provider computer systems. The electronic communications may be Internet connections, virtual private network (VPN) connections, proprietary network connections, or other electronic communication connections. The loan company may also automate the loan qualification process so that loan approval may happen quickly. Thus, the health care patient may know about available loans within a few seconds of completing the estimation report/letter. Further, payment may also be received electronically. For loan companies and/or health care providers that cannot handle electronic payments, loan payments may be made via a check or other acceptable payment mechanism.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A computerized method for estimating treatment related amounts, including treatment costs, contract allowable amounts, and patient payable amounts, of a health care provider for a health care patient to receive a health care product/service comprising:

supplying a computer system that runs computer software, said computer software performing said computerized method for estimating said treatment related amounts of said health care provider for said health care patient to receive said health care product/service, said computer system having computer readable storage media for storing said computer software as well as data entry information, said estimated treatment related amounts including estimated treatment costs, an estimated allowable amount, and an estimated patient payable amount;

entering facility information for a facility that is to provide said health care product/service to said health care patient into said computer software;

entering patient information about said health care patient into said computer software;

entering insurance information about health insurance provided by an insurance company that covers said health care patient into said computer software;

entering health care code information about said health care product/service that is to be provided to said health care patient into said computer software;

entering insurance benefits information for said health insurance that covers said health care patient into said computer software;

performing estimation calculations in said computer software prior to said health care patient being discharged from said facility and prior to final costs for said health care product/service being available from said insurance company such that said estimated treatment related amounts to receive said health care product/service are calculated by taking into account said facility information, said patient information, said insurance information, said insurance benefits information, and said health care code information, said process of performing estimation calculations comprising:

receiving inputs of a contract allowable amount, a maximum deductible amount, a deductible met amount, a co-pay amount, a co-pay-charged-daily-indicator indicating whether said co-pay amount is charged daily, a number of co-pays days value, a co-insurance percentage, a maximum out of pocket, an out of pocket met amount, a deductible-included-in-out-of-pocket-amount-indicator indicating whether a deductible owable amount is included in an out of pocket owed amount, and a co-pay-included-in-out-of-pocket-amount-indicator indicating whether a co-pay due amount is included in said out of pocket owed amount;

calculating said deductible owable amount by subtracting said deductible met amount from said maximum deductible amount;

calculating said co-pay due amount by interrogating said co-pay-charged-daily-indicator and if said co-pay-charged-daily-indicator is true, then:

calculating said co-pay due amount by multiplying said co-pay amount by said number of co-pay days value, otherwise:

calculating said co-pay due amount by setting said co-pay due amount equal to said co-pay amount;

calculating a co-insurance due amount by subtracting said deductible owable amount and said co-pay due amount from said contract allowable amount to obtain an interim co-insurance due result, and multiplying said interim co-insurance due result by said co-insurance percentage;

calculating said out of pocket owed amount by first interrogating said deductible-included-in-out-of-pocket-amount-indicator and if said deductible-included-in-out-of-pocket-amount-indicator is false, then:

interrogating said co-pay-included-in-out-of-pocket-amount-indicator and if said co-pay-included-in-out-of-pocket-amount-indicator is false, then:

setting said out of pocket owed amount to said maximum out of pocket amount minus said out of pocket met amount, if said co-pay-included-in-out-of-pocket-amount-indicator is true, then:

setting said out of pocket owed amount to said maximum out of pocket amount minus said out of pocket met amount and minus said co-pay due amount, if said deductible-included-in-out-of-pocket-amount-indicator is true, then:

interrogating said co-pay-included-in-out-of-pocket-amount-indicator and if said co-pay-included-in-out-of-pocket-amount-indicator is false, then:

setting said out of pocket owed amount to said maximum out of pocket amount minus said out of pocket met amount and minus said deductible owable amount, if said co-pay-included-in-out-of-pocket-amount-indicator is true, then:

setting said out of pocket owed amount to said maximum out of pocket amount minus said out of pocket met amount and minus said deductible owable amount and minus said co-pay due amount;

comparing said deductible owable amount to said contract allowable amount;

performing a first subset of processes if said deductible owable amount is greater than said contract allowable amount, said first subset of processes comprising:

calculating a deductible payable amount by setting said deductible payable amount equal to said contract allowable amount; and calculating a payable amount for said health care patient by first comparing said deductible payable amount to said out of pocket owed amount and if said deductible payable amount is greater than said out of pocket owed amount, then:

setting said payable amount equal to said out of pocket owed amount, otherwise:

calculating said payable amount by setting said payable amount equal to said contract allowable amount; and performing a second subset of processes if said deductible owable amount is not greater than said contract allowable amount, said second subset of processes comprising:

calculating said deductible payable amount by setting said deductible payable amount equal to said deductible owable amount;

comparing said deductible payable amount plus said co-pay due amount to said contract allowable amount and if said deductible payable amount plus said co-pay due amount is greater than said contract allowable amount, then:

setting said co-insurance due amount to zero, otherwise:

keeping said co-insurance due amount as calculated;

calculating a payable amount for said health care patient by first comparing said deductible payable amount plus said co-insurance due amount to said out of pocket owed amount and if said deductible payable amount plus said co-insurance due amount is greater than said out of pocket owed amount, then:

setting said payable amount equal to said out of pocket owed amount, otherwise:

calculating said payable amount by setting said payable amount equal to said deductible owed amount plus said co-insurance due amount plus said co-pay due amount;

creating an estimation report in said computer software that shows said estimation calculations; and delivering said estimation report to an interested party.

2. The computerized method of claim 1:

wherein entering said facility information further comprises selecting a facility from a predefined list of facilities where said health care product/service is to be provided, said predefined list of facilities being stored on said computer readable media that is part of said computer system;

wherein entering insurance information further comprises selecting the insurance company from a predefined list of insurance companies based on said insurance company information, said predefined list of insurance companies being stored on said computer readable storage media of said computer system, and each entry in said predefined list of insurance companies being associated with a predefined contract such that by selecting the insurance company permits said computer software access to contract details for said selected insurance company;

wherein entering insurance information also further comprises entering insurance policy information into said computer software; and wherein said entering health care code information further comprises selecting at least one health care code from a pre-defined list of health care codes such that said selected at least one health care code is indicative of said health care product/service to be provided to said health care patient.

3. The computerized method of claim 2 wherein said process of gathering health care code information further comprises:

selecting at least one International Classification of Diseases (ICD) code that provides an upper level description for said at least one health care product/service;

relating said at least one ICD code to at least one Diagnostic Related Groups (DRG)/Medical Severity Diagnostic Related Groups (MSDRG) code such that said selected at least one DRG/MSDRG code provides a low level description for said at least one health care product/service.

4. The computerized method of claim 3 further comprising: creating said relationship between said at least one International Classification of Disease (ICD) code and said at least one Diagnostic Related Groups (DRG)/Medical Severity Diagnostic Related Groups (MSDRG) code by analyzing historical medical records to determine a historic relationship between said at least one ICD code and said at least one DRG/MSDRG code.

5. The computerized method of claim 2:
wherein said patient information includes at least one of the group comprising: date of birth, gender, name, and facility account number;
wherein said insurance policy information includes at least one of the group comprising: insurance policy number and insurance group number;
wherein said health care code information includes health care codes selected from at least one of the group comprising: International Classification of Diseases (ICD) codes, Diagnostic Related Groups (DRG) codes, Medical Severity Diagnostic Related Groups (MSDRG) codes, Current Procedural Terminology (CPT) codes, Healthcare Common Procedure Coding System (HCPCS) codes, health care facility specific codes, doctor specific codes, and proprietary health care codes;
wherein said insurance benefits information includes at least one of the group comprising: family maximum deductible amount, family deductible met amount, family maximum out of pocket amount, and family out of pocket met amount; and
wherein said interested party includes at least one of the group comprising: said health care provider, said facility, the insurance company as specified in said insurance information, and said health care patient.

6. The computerized method of claim 2 wherein said contract details define said contract allowable amount for said health care product/service.

7. The computerized method of claim 2 further comprising:
gathering facility information on available facilities;
entering said facility information into said computer software;
creating said predefined list of facilities by said computer software based on said facility information; and
maintaining and updating said facility information using said computer software.

8. The computerized method of claim 1 further comprising:
entering a date of service that defines when said health care product/service is to start for said health patient into said computer software; and
including said date of service in said estimation calculation.

9. The computerized method of claim 2 further comprising:
gathering insurance company contract information on available insurance company contracts;
entering said insurance company contract information into said computer software;
creating said predefined list of insurance company contracts by said computer software based on said insurance company contract information; and
maintaining and updating said insurance company contract information using said computer software.

10. The computerized method of claim 1 further comprising delivering said estimation report prior to providing said health care product/service to said health care patient.

11. The computerized method of claim 10 further comprising: collecting payment from said health care patient for said estimated patient payable amount owed by said health care patient prior to providing said health care product/service to said health care patient.

12. The computerized method of claim 1 wherein said estimated treatment costs of said estimated treatment related amounts are further based on historical costs for said health care product/service of said health care provider.

13. The computerized method of claim 12 wherein said historical costs include at least one of the group comprising: average price, median price, average length of stay, median length of stay, average implant/material cost, and median implant/material cost.

14. The computerized method of claim 1 wherein said process of performing estimation calculations in said computer software and said process for creating said estimation report are performed prior to said health care product/service being rendered to said health care patient.

15. The computerized method of claim 1 further comprising collecting payment from said health care patient for said estimated patient payable amount owed by said health care patient prior to discharging said patient from said selected facility, said estimated patient payable amount being a part of said estimated treatment related amounts.

16. The computerized method of claim 1 further comprising:
providing access to at least one loan company to said health care patient;
delivering said estimation report containing said estimated patient payable amount owed by said health care patient to said at least one loan company such that said health care patient is able to qualify for a loan from said at least one loan company; and
collecting payment from proceeds of a loan provided by said at least one loan company prior to said health care patient being discharged from said selected facility.

17. The computerized method of claim 1 further comprising:
qualifying said health care patient for a loan in an amount equal to said estimated patient payable amount owed by said health care patient prior to said health care patient being discharged from said selected facility;
providing said health care patient said loan for said estimated patient payable amount for said health care product/service if said health care patient qualifies for said loan; and
paying said estimated patient payable amount for said health care product/service with proceeds of said loan in said amount equal to said estimated patient payable amount prior to said health care patient being discharged from said selected facility.

18. The computerized method of claim 1 further comprising selecting said health care provider from a predefined list of health care providers, said predefined list of health care providers being stored on said computer readable media that is part of said computer system.

* * * * *